United States Patent
Huang et al.

(10) Patent No.: US 12,195,552 B2
(45) Date of Patent: Jan. 14, 2025

(54) LINKER FOR ANTIBODY-DRUG CONJUGATES AND ITS USE

(71) Applicant: RemeGen Co., Ltd., Yantai (CN)

(72) Inventors: Changjiang Huang, Yantai (CN); Hui Ye, Yantai (CN); Hu Chen, Yantai (CN); Xiuzhi Zhan, Yantai (CN); Nan Shen, Yantai (CN); Wenting Luo, Yantai (CN); Qiaohua Hou, Yantai (CN); Jianmin Fang, Yantai (CN)

(73) Assignee: RemeGen Co., Ltd., Yantai (CN)

( * ) Notice: Subject to any disclaimer, the term of this patent is extended or adjusted under 35 U.S.C. 154(b) by 1037 days.

(21) Appl. No.: 17/260,901

(22) PCT Filed: Dec. 13, 2019

(86) PCT No.: PCT/CN2019/124982
§ 371 (c)(1),
(2) Date: Jan. 15, 2021

(87) PCT Pub. No.: WO2020/125546
PCT Pub. Date: Jun. 25, 2020

(65) Prior Publication Data
US 2022/0072137 A1 Mar. 10, 2022

(30) Foreign Application Priority Data
Dec. 17, 2018 (CN) ............................ 201811541356

(51) Int. Cl.
*A61K 47/54* (2017.01)
*A61K 45/06* (2006.01)
(Continued)

(52) U.S. Cl.
CPC .............. *C07K 16/32* (2013.01); *A61K 45/06* (2013.01); *A61K 47/545* (2017.08);
(Continued)

(58) Field of Classification Search
None
See application file for complete search history.

(56) References Cited

U.S. PATENT DOCUMENTS

| 2012/0190579 A1 | 7/2012 | Smith et al. |
| 2013/0197059 A1 | 8/2013 | Goodnow, Jr. et al. |

(Continued)

FOREIGN PATENT DOCUMENTS

| CN | 103933575 A | 7/2014 |
| CN | 105592859 A | 5/2016 |

(Continued)

OTHER PUBLICATIONS

Li et al., Tetrahedron Letters. 2016: 57: 2660-3 (Year: 2016).*
(Continued)

*Primary Examiner* — Karl J Puttlitz
(74) *Attorney, Agent, or Firm* — Wolf, Greenfield & Sacks, P.C.

(57) ABSTRACT

The present invention provides a linker for preparing antibody-drug conjugates and antibody-drug conjugates prepared by the linker, as well as use of the antibody-drug conjugates in a medicament for treating tumor. The linker is capable of coupling simultaneously with the thiol group or amino group on the antibody or functional fragment of the antibody, especially it is capable of coupling with 2, 3 or 4 thiol groups on the antibody or functional fragment of the antibody. A coupled product is uniform and structurally stable.

1 Claim, 9 Drawing Sheets

(51) Int. Cl.
*A61K 47/68* (2017.01)
*C07K 16/32* (2006.01)
(52) U.S. Cl.
CPC .. *A61K 47/68031* (2023.08); *A61K 47/68033* (2023.08); *A61K 47/6849* (2017.08); *A61K 47/6851* (2017.08)

(56) References Cited

U.S. PATENT DOCUMENTS

| | | | | |
|---|---|---|---|---|
| 2013/0224228 | A1* | 8/2013 | Jackson | A61P 35/00 530/331 |
| 2016/0015832 | A1* | 1/2016 | An | C07D 207/452 530/391.9 |

FOREIGN PATENT DOCUMENTS

| | | |
|---|---|---|
| CN | 106267225 A | 1/2017 |
| CN | 107400072 A | 11/2017 |
| CN | 107652219 A | 2/2018 |
| CN | 107921030 A | 4/2018 |
| JP | S52-93765 A | 8/1977 |
| JP | H09-506650 A | 6/1997 |
| JP | 2013-501764 A | 1/2013 |
| JP | 2016-531094 A | 10/2016 |
| JP | 2018-515610 A | 6/2018 |
| JP | 2018-529646 A | 10/2018 |
| RU | 2 624 732 C2 | 7/2017 |
| SU | 520040 A3 | 6/1976 |
| TW | 201718025 A | 6/2017 |
| WO | WO 9516738 A1 | 6/1995 |
| WO | WO 2008/034124 A2 | 3/2008 |
| WO | WO 2008/034124 A3 | 3/2008 |
| WO | WO 2013/085925 A1 | 6/2013 |
| WO | WO 2013/121175 A1 | 8/2013 |
| WO | WO 2014/114207 A1 | 7/2014 |
| WO | WO 2014/197871 A2 | 12/2014 |
| WO | WO 2015/004400 A1 | 1/2015 |
| WO | WO 2015/151081 A2 | 10/2015 |
| WO | WO 2015/151081 A3 | 10/2015 |
| WO | WO 2016/004048 A2 | 1/2016 |
| WO | WO 2016/004048 A3 | 1/2016 |
| WO | WO-2016064749 A2 * | 4/2016 ............. A61K 38/07 |
| WO | WO 2016/192528 A1 | 12/2016 |
| WO | WO 2017/031034 A2 | 2/2017 |
| WO | WO 2017/046658 A1 | 3/2017 |
| WO | WO 2018/185131 A2 | 10/2018 |
| WO | WO 2018/185131 A3 | 10/2018 |
| WO | WO 2019/033773 A1 | 2/2019 |

OTHER PUBLICATIONS

Carey, FA. Organic Chemistry 6th Ed. McGraw Hill. 2006, chapter 1, p. 9 (Year: 2006).*
Japanese Office Action for Application No. 2021-517698, mailed Jan. 31, 2023.
Schumacher et al., In situ maleimide bridging of disulfides and a new approach to protein PEGylation. Bioconjug Chem. Feb. 16, 2011;22(2):132-6. doi: 10.1021/bc1004685. Epub Jan. 27, 2011.
Schumacher et al., Next generation maleimides enable the controlled assembly of antibody-drug conjugates via native disulfide bond bridging. Org Biomol Chem. Oct. 7, 2014;12(37):7261-9. doi: 10.1039/c4ob01550a.
Office Action for Taiwanese Application No. TW108146262, mailed Jan. 8, 2021.
International Search Report and Written Opinion for PCT/CN2019/124982, mailed Mar. 12, 2020.
Extended European Search Report for Application No. 19900942.4, mailed May 13, 2022.
Japanese Office Action for Application No. 2021-517698, mailed Jun. 21, 2022.
Li et al., A mild and selective protecting and reversed modification of thiols. Tetrahedron Letters. 2016; 57: 2660-3.
Ramesh et al., 6-(Bromomaleimido)hexanoic acid as a connector for the construction of multiple branched peptide platforms. Org Lett. Feb. 6, 2015;17(3):464-7. doi: 10.1021/01503463u. Epub Jan. 12, 2015.
Shen et al., Conjugation site modulates the in vivo stability and therapeutic activity of antibody-drug conjugates. Nat Biotechnol. Jan. 22, 2012;30(2):184-9. doi: 10.1038/nbt.2108.
International Preliminary Report on Patentability for PCT/CN2019/124982, mailed Jul. 1, 2021.

* cited by examiner

1:Her2-A'-7-Val-Cit-PAB-MMAE
2:Her2-575DZ-Val-Cit-PAB-MMAE
3:Her2-A'-10-Val-Cit-PAB-MMAE

LINKER FOR ANTIBODY-DRUG CONJUGATES AND ITS USE

RELATED APPLICATIONS

This application is a national stage filing under 35 U.S.C. § 371 of International PCT Application PCT/CN2019/124982, filed Dec. 13, 2019, which claims priority to Chinese Patent Application No. 201811541356.0, filed Dec. 17, 2018, the entire contents of each of which is incorporated herein by reference.

TECHNICAL FIELD

The present invention relates to a linker for antibody-drug conjugates and antibody-drug conjugates prepred by the linker, as well as use of the antibody-drug conjugates in treating tumor and other diseases.

BACKGROUND ART

Antibody-drug conjugates (ADCs) are a class of targeted therapeutic drugs, which are mainly used for treating cancer, autoimmune diseases and the like. Their structures usually consist of three moieties: antibody or antibody-like ligand, drug moiety, and linker that couples the antibody or antibody-like ligand and the drug.

Traditional ADC drug is obtained by coupling a drug to lysine residue of antibody or cysteine residue produced by the reduction of interchain disulfide bond of antibody through a linker. When lysine residue is used as the coupling site, since an antibody contains about 40 or more lysine residues, and the coupling reaction is non-selective, the coupling number and site have great uncertainty, and the product uniformity is very poor. When cysteine residue is used as the coupling site, although the antibody (IgG1) has only 4 pairs of interchain disulfide bonds, and the DAR (drug to antibody ratio) value of the ADC drug formed by the cysteine residue produced by the reduction of interchain disulfide bond is relatively uniform, this coupling method destroys the disulfide bond of the antibody, affecting the stability of the antibody. And, due to poor selectivity of the existing reducing agents (DTT, TCEP) for interchain disulfide bonds, the uniformity of the final product is also poor. In view of therapeutic effect and drug supervision, the uniformity of product is very important. Therefore, it is necessary to prepare ADC drugs with well-controlled drug to antibody ratio.

In recent years, some researchers have used genetic engineering technology to modify antibodies to achieve targeted coupling of antibodies and drugs, and the ADCs obtained also have very uniform DAR values. However, because genetic recombination technology requires a lot of work and design to look for a suitable site for drug coupling or polyethylene glycol modification, it is very time-consuming and extremely expensive in development.

Considering the above-mentioned defects in the preparation of antibody-drug conjugates in the prior art, there is an urgent need in the art to develop a new linker to achieve targeted coupling of toxic drugs to antibodies, so as to obtain ADC drugs with higher product uniformity and stronger stability.

Contents of the Invention

In order to solve the above-mentioned problems, the present invention provides a linker for preparing antibody-drug conjugates and antibody-drug conjugates prepared by the linker, as well as use of the antibody-drug conjugates in a medicament for treating tumor. The linker is capable of coupling simultaneously with the thiol group(s) or amino group(s) on the antibody or functional fragment of the antibody, especially it is capable of coupling with 2, 3 or 4 thiol groups on the antibody or functional fragment of the antibody. A coupled product is uniform and structurally stable.

In the first aspect, the present invention provides a linker, which has a structure of Formula I:

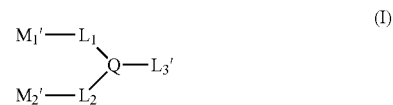

(I)

wherein, $M_1'$, $M_2'$ each are independently selected from

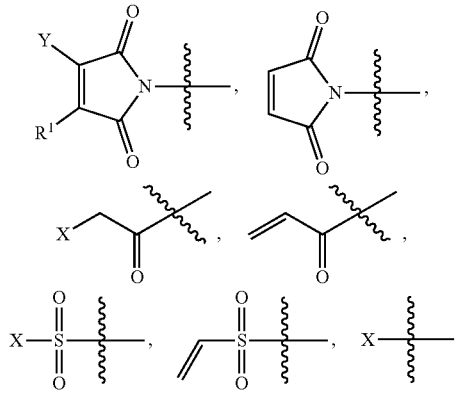

or are absent, $M_1'$, $M_2'$ are the same or different, but are not absent at the same time;

X, Y, $R^1$, $L_1$, $L_2$, $L_3'$, Q are each an arbitrary group.

Furthermore, the above-mentioned X, Y, $R^1$, $L_1$, $L_2$, $L_3'$, Q may be:

$L_1$, $L_2$ each are independently selected from $C_1$-$C_9$ alkyl, $C_2$-$C_9$ alkenyl, $C_2$-$C_9$ alkynyl, aryl, heteroaryl, $C_3$-$C_9$ cycloalkyl, $C_3$-$C_9$ heterocyclyl, polyethylene glycol, O, S,

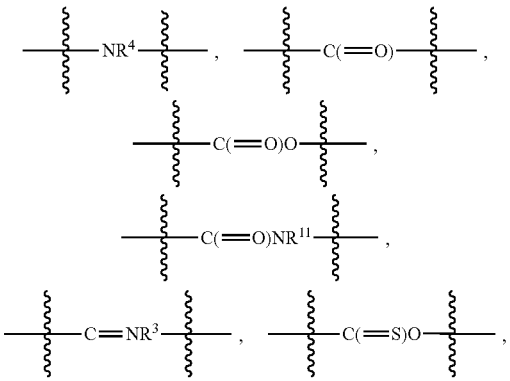

-continued

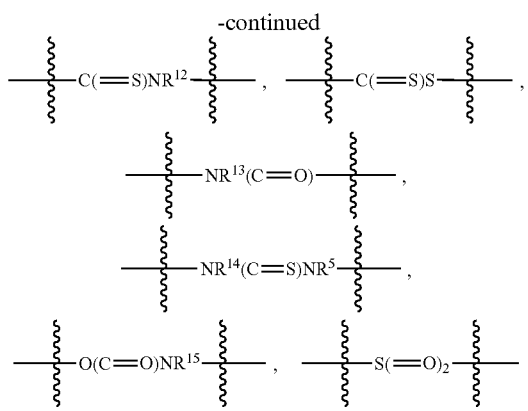

and any combination thereof;
Q is selected from

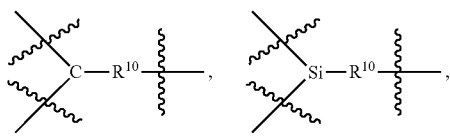

N, B, P, aryl, heteroaryl, cycloalkyl, (heterocyclyl) alkyl;

$L_3'$ is selected from

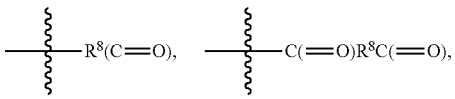

polyethylene glycol,

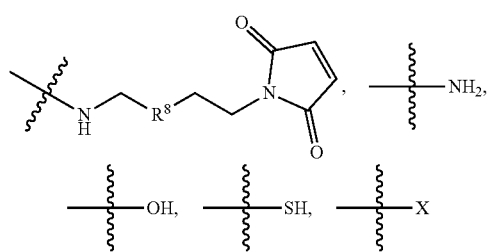

and any combination thereof;
X is selected from F, Cl, Br, I;
Y is

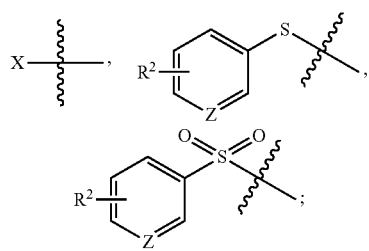

(In the above two structures, the substitution of $R^2$ may occur at any position on the ring.)

Z is selected from C, N;

$R^1, R^2, R^3, R^4, R^5, R^8, R^{10}, R^{11}, R^{12}, R^{13}, R^{14}, R^{15}$ each are independently selected from H, $C_1$-$C_6$ alkyl, $C_2$-$C_6$ alkenyl, $C_2$-$C_6$ alkynyl, aryl, heteroaryl, $C_3$-$C_9$ cycloalkyl, $C_3$-$C_9$ heterocyclyl.

Still furthermore, the above-mentioned X, Y, $R^1$, $L_1$, $L_2$, $L_3'$, Q may be:

$L_1, L_2$ each are independently selected from $C_1$-$C_4$ alkyl, $C_6$-$C_8$ aryl, $C_6$-$C_8$ heteroaryl, $C_5$-$C_6$ cycloalkyl, $C_5$-$C_6$ heterocyclyl, $C_2$-$C_{12}$ polyethylene glycol, O, S,

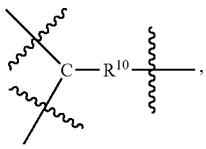

Q is selected from

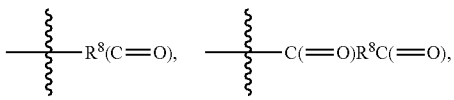

N, $C_6$-$C_8$ aryl, $C_6$-$C_8$ heteroaryl, $C_3$-$C_8$ cycloalkyl, $C_3$-$C_8$ heterocyclyl;

$L_3'$ is selected from

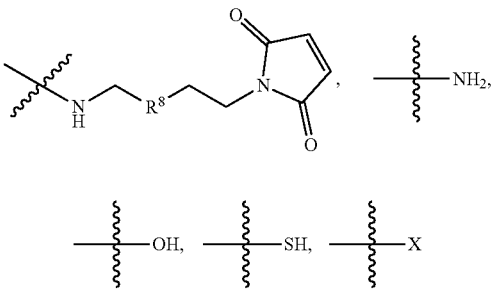

polyethylene glycol, and any combination thereof;
X is Br;
Y is
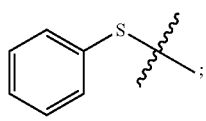 [SMILES: *Sc1ccccc1]
R¹, R², R³, R⁴, R⁵, R⁸, R¹⁰, R¹¹, R¹⁵ each are independently selected from H, $C_1$-$C_4$ alkyl, $C_6$-$C_8$ aryl, $C_6$-$C_8$ heteroaryl, $C_5$-$C_6$ cycloalkyl, $C_5$-$C_6$ heterocyclyl.
Furthermore, the linker has the structure represented by formula:
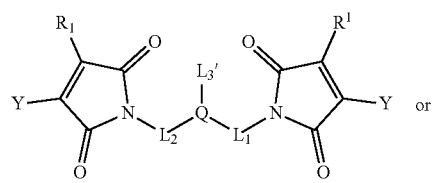 (A'-1')
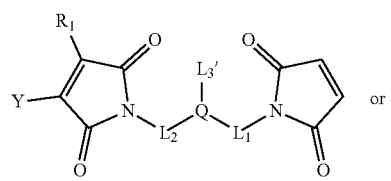 (A'-2')
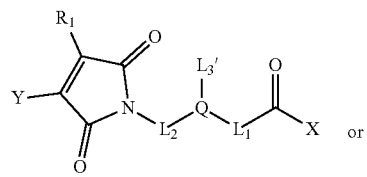 (A'-3')
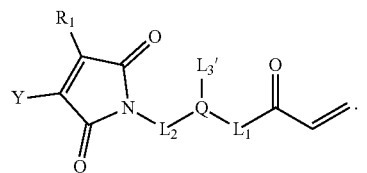 (A'-4')
Preferably, the linker may have the structure:
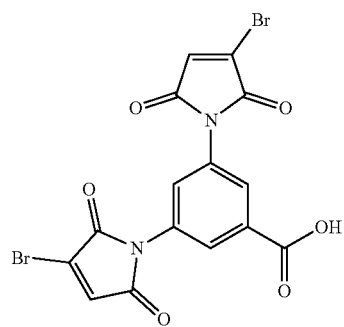 A'-1
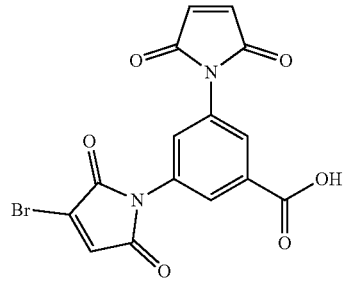 A'-2
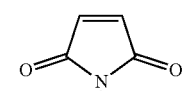 A'-4
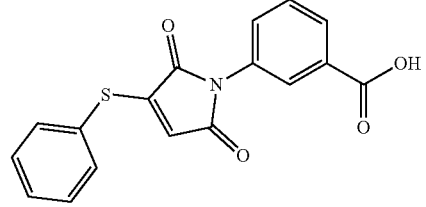
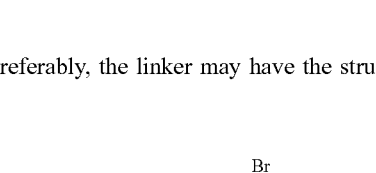 A'-5
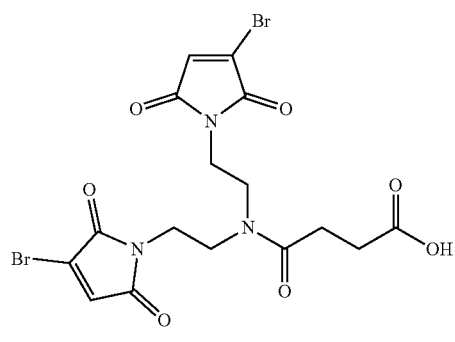 A'-7

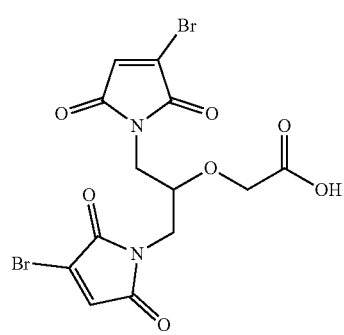
A'-8
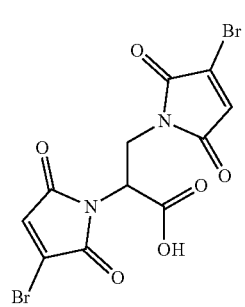
A'-9
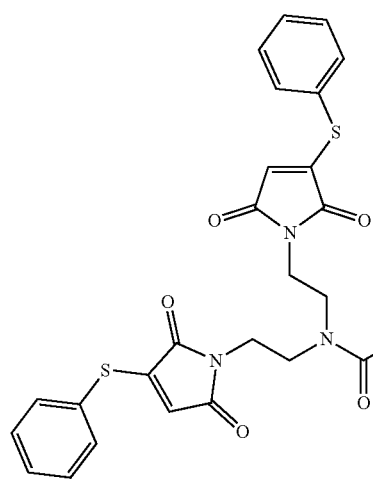
A'-10
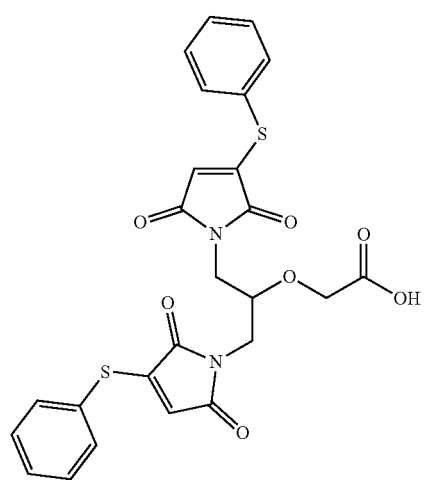
A'-11
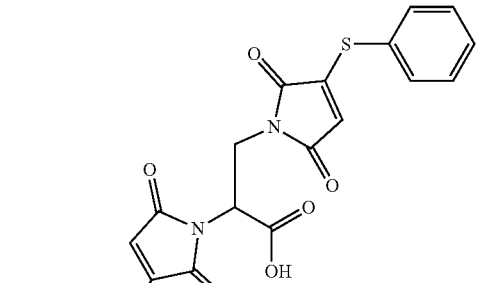
A'-12
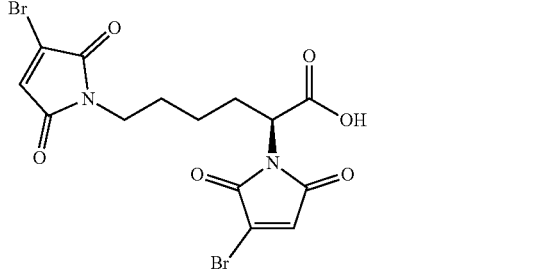
A'-13
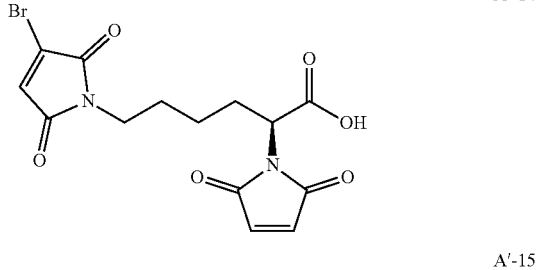
A'-14
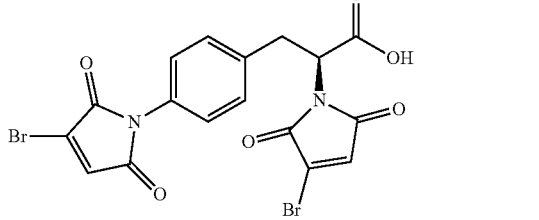
A'-15
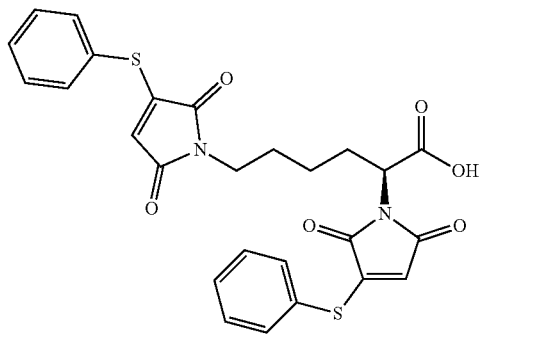
A'-16

A'-19 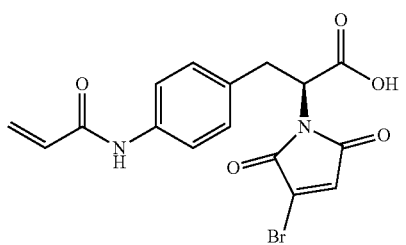
A'-20 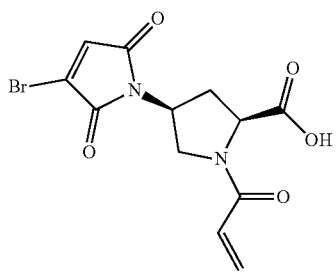
A'-21 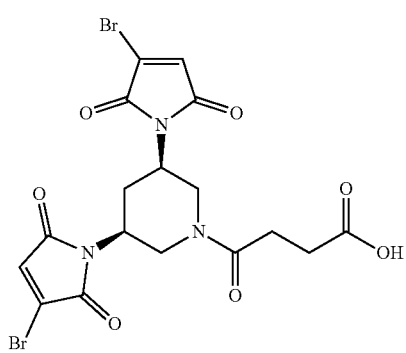
A'-22 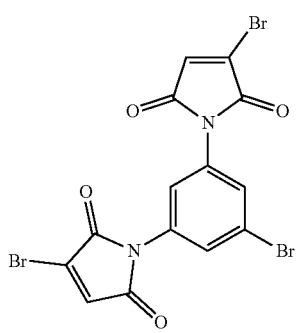
A'-24 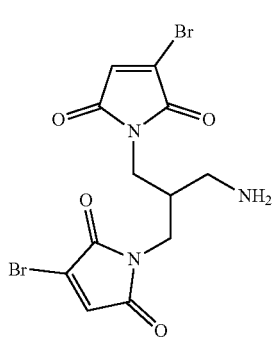
A'-26 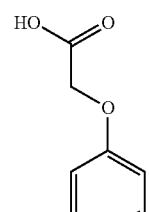
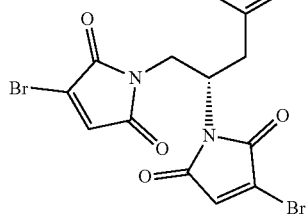
A'-27 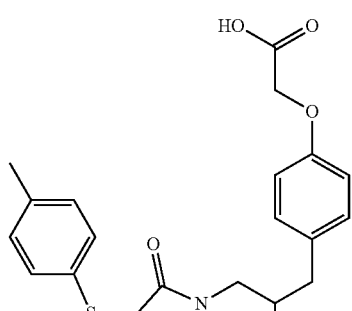
A'-28 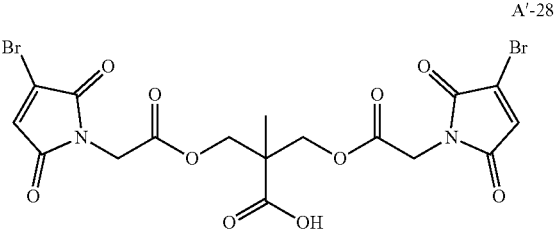
A'-29 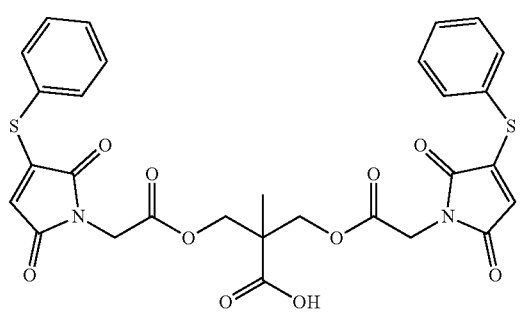

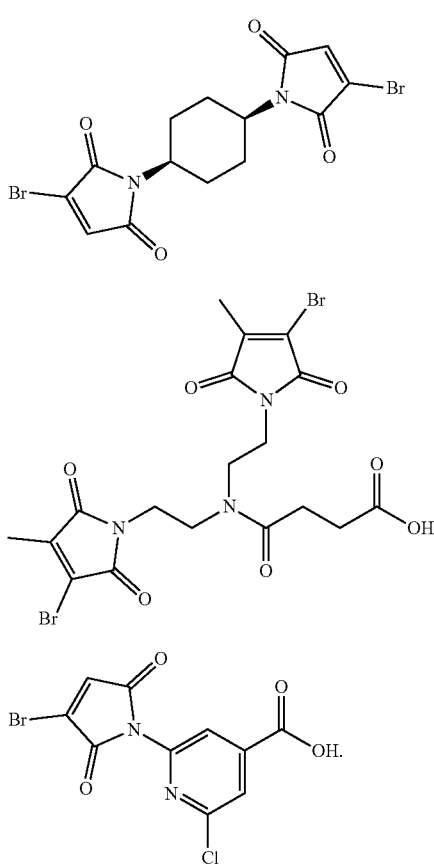

The present invention also provides use of the above-mentioned linker in the preparation of antibody-drug conjugates.

In another aspect, the present invention provides an antibody-drug conjugate, the antibody-drug conjugate having the structure represented by Formula II:

Ab-(A-L-D)n     (II)

wherein,

Ab is any antibody or functional fragment of the antibody. Furthermore, the antibody includes a derivative or an analog of the antibody; "functional" fragment represents an antibody, a fragment, a derivative or an analog thereof that is capable of recognizing the same antigen, and is capable of recognizing fragments, derivatives or analogs derived from the antigen, which includes, for example, but not limited to: F (ab') 2, Fab, Fab', Fv fragments and heavy and light chain dimers of antibodies, or any of their smallest fragments such as Fvs or single-chain antibody (single-chain antibody fragment/single-chain variable fragment, scFv). In addition, the antibody can be a fusion protein of the antibody. The antibody can also include modified or unmodified (that is, covalent linkage through any molecule) analogs and derivatives, as long as such covalent linkage allows the antibody to retain its antigen-binding immunologic specificity. It includes, for example, but not limited to: analogs and derivatives of antibody, including further modifications, such as: glycosylation, acetylation, PEGylation, phosphorylation, amidation, derivatization through known protecting/blocking groups, protease cleavage, connection to cell antibody units or other proteins and the like. Any large number of chemical modifications can be achieved using known techniques, including, but not limited to, specific chemical cleavage, acetylation, formylation, metabolic synthesis in the presence of tunicamycin and the like. In addition, analogs or derivatives may include one or more unnatural amino acids. In some examples, antibodies may have modifications (e.g. substitution, deletion, or addition) in the amino acid residues that interact with Fc receptor. Still furthermore, the antibody is selected from murine antibodies, mammalian antibodies, chimeric antibodies, humanized antibodies, human antibody, multispecific antibodies.

The linker moiety includes a first linker moiety A and a second linker moiety L; the first linker moiety A includes a group covalently linked to the thiol group or amino group in the Ab.

D is the drug moiety, the drug including, but not limited to, cytotoxic drugs, cell differentiation factors, stem cell nutritional factors, steroid drugs, drugs for the treatment of autoimmune diseases, anti-inflammatory drugs or drugs for the treatment of infectious diseases. Furthermore, the drug moiety D includes, but not limited to, tubulin inhibitors or DNA damaging agents. The tubulin inhibitors include, but are not limited to, dolastatin, auristatins, maytansines; the DNA damaging agents include, but not limited to, calicheamicins, duocarmycins, anthramycin derivative PBD (pyrrolobenzodiazepine), camptothecin derivative SN-38, topoisomerase I inhibitors. The auristatin drugs include, but not limited to, monomethyl auristatin E (MMAE), monomethyl auristatin F (MMAF), and auristatin F (AF) or their derivatives. The maytansine drugs include, but not limited to, DM1, DM3, DM4 or their derivatives (Research Progress on Warhead Molecules of antibody-drug conjugate, Hu Xinyue et al., Chinese Medicinal Biotechnology, December 2017, Vol. 12, No. 6) (Research advance of maytansinoid class antibody drug conjugates, Zhou Lei et al., Chinese Journal of New Drugs, 2016, Vol. 25, No. 22, pages 2521-2530). The drug moiety D can also be amanitins, anthracyclines, baccatins, camptothecins, cemadotins, colchicines, colcimids, combretastatins, cryptophycins, discodermolides, docetaxel, doxorubicin, echinomycins, eleutherobins, epothilones, estramustines, lexitropsins, maytansines, methotrexate, netropsins, puromycins, rhizoxins, taxanes, tubulysins, or vinca alkaloids. The drug moiety D may also be vitamin A precursor, folic acid and the like. The drug moiety D is not limited to the above categories, but also includes all drugs that can be used for ADC.

n is 1, 2, 3 or 4;

It is characterized in that, the first linker moiety A has the structure represented by Formula III:

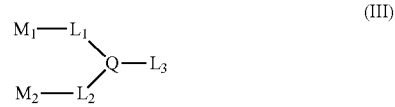

wherein:

$M_1$, $M_2$ are covalently linked to the thiol group or amino group of the antibody or functional fragment moiety of the antibody (that is Ab), which each are independently selected from

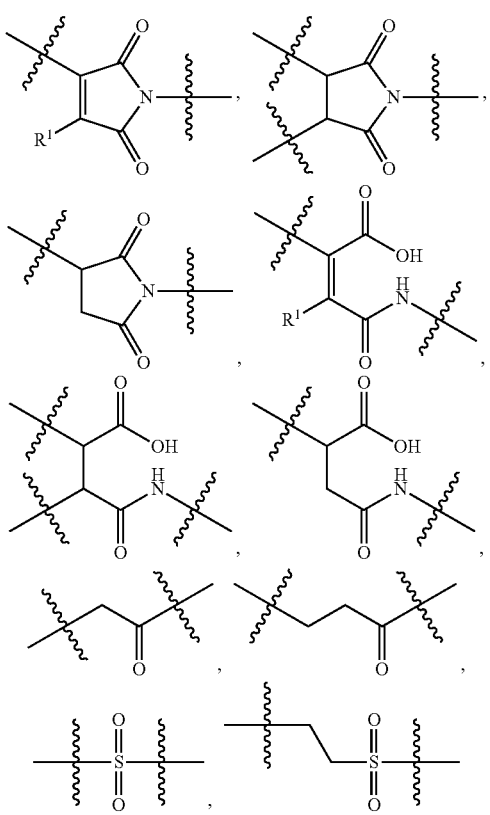

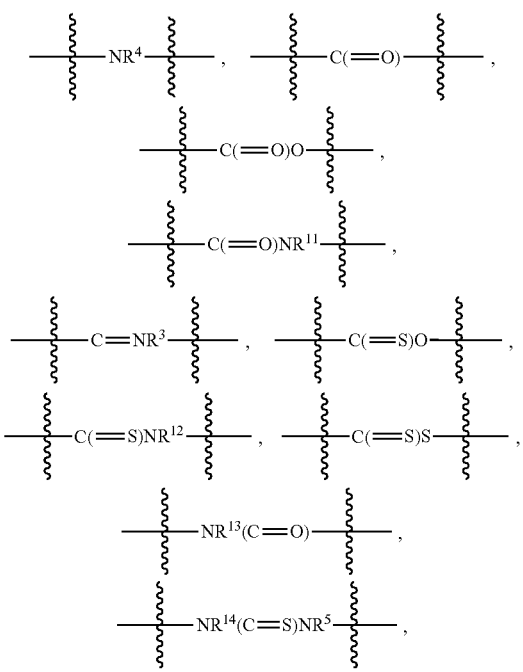

or are absent, $M_1$ and $M_2$ are the same or different, but cannot be absent at the same time;

$L_1$, $L_2$ each are independently selected from $C_1$-$C_9$ alkyl, $C_2$-$C_9$ alkenyl, $C_2$-$C_9$ alkynyl, aryl, heteroaryl, $C_3$-$C_9$ cycloalkyl, $C_3$-$C_9$ heterocyclyl, polyethylene glycol, O, S,

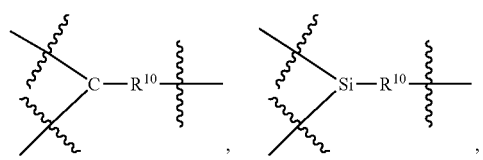

-continued

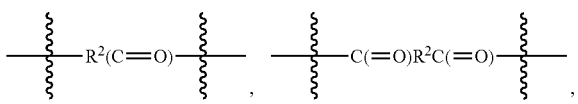

and any combination thereof;
Q is selected from

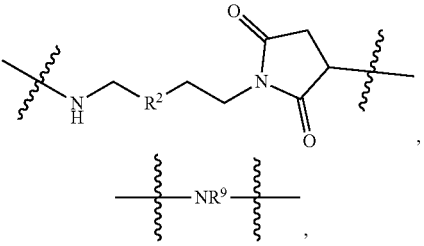

N, B, P, aryl, heteroaryl, cycloalkyl, (heterocyclyl) alkyl;

$L_3$ is covalently linked to the second linker moiety L, which is selected from

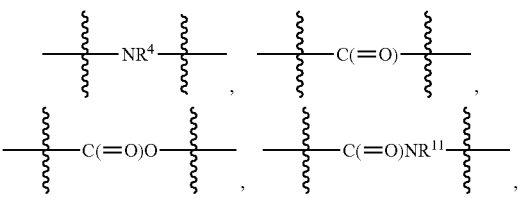

polyethylene glycol,

O, S and any combination thereof or is absent;

$R^1$ is an arbitrary group or is absent, $R^2$, $R^3$, $R^4$, $R^5$, $R^9$, $R^{10}$, $R^{11}$, $R^{12}$, $R^{13}$, $R^{14}$, $R^{15}$ each are independently selected from H, $C_1$-$C_6$ alkyl, $C_2$-$C_6$ alkenyl, $C_2$-$C_6$ alkynyl, aryl, heteroaryl, $C_3$-$C_9$ cycloalkyl, $C_3$-$C_9$ heterocyclyl;

the second linker moiety L is any cleavable linker or non-cleavable linker or is absent, when L is absent, $L_3$ is directly covalently linked to the drug moiety D.

Still furthermore, the above-mentioned $L_1$, $L_2$, $L_3$, Q, $R^1$ further may be respectively:

$L_1$, $L_2$ each are independently selected from $C_1$-$C_4$ alkyl, $C_6$-$C_8$ aryl, $C_6$-$C_8$ heteroaryl, $C_5$-$C_6$ cycloalkyl, $C_5$-$C_6$ heterocyclyl, $C_2$-$C_{12}$ polyethylene glycol, O, S, -continued

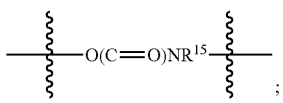

Q is selected from

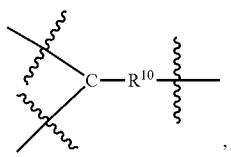

N, $C_6$-$C_8$ aryl, $C_6$-$C_8$ heteroaryl, $C_3$-$C_8$ cycloalkyl, $C_3$-$C_8$ heterocyclyl;

$L_3$ is selected from

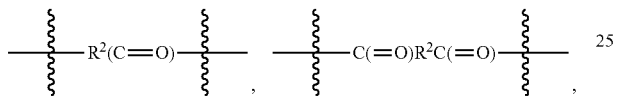

polyethylene glycol,

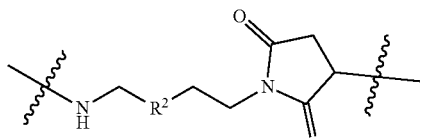

O, S and any combination thereof or is absent;

$R^1$ is selected from H, $C_1$-$C_6$ alkyl, $C_2$-$C_6$ alkenyl, $C_2$-$C_6$ alkynyl, aryl, heteroaryl, $C_3$-$C_9$ cycloalkyl, $C_3$-$C_9$ heterocyclyl.

Still furthermore, the first linker moiety has the structure:

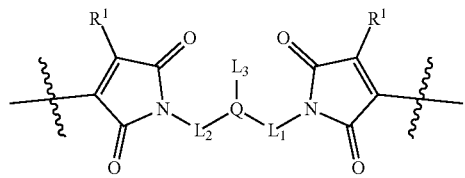
(A-1')

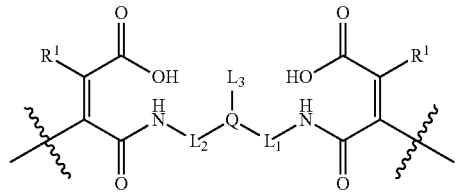
(A-1")

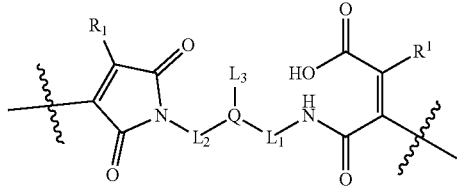
(A-1''')

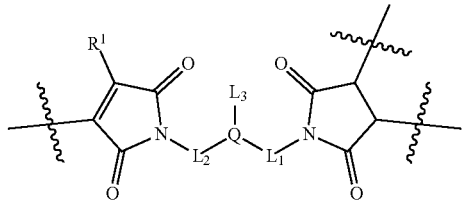
(A-2')

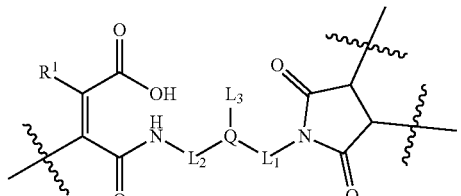
(A-2")

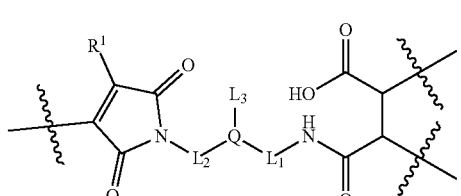
(A-2''')

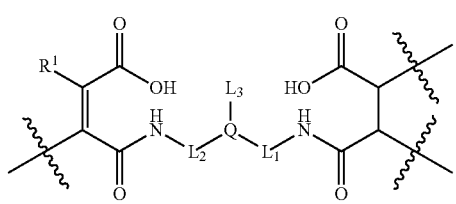
(A-2'''')

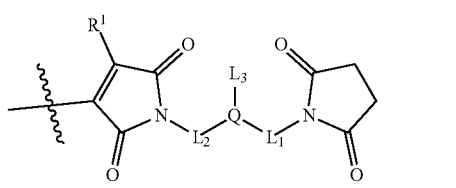
(A-3')

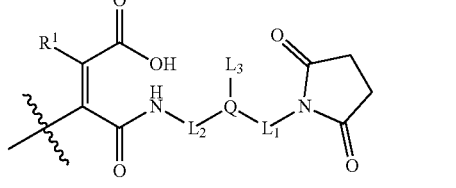
(A-3")

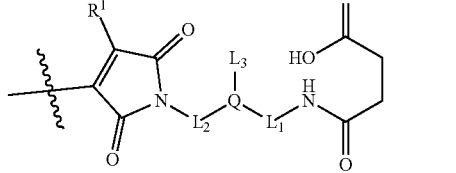
(A-3''')

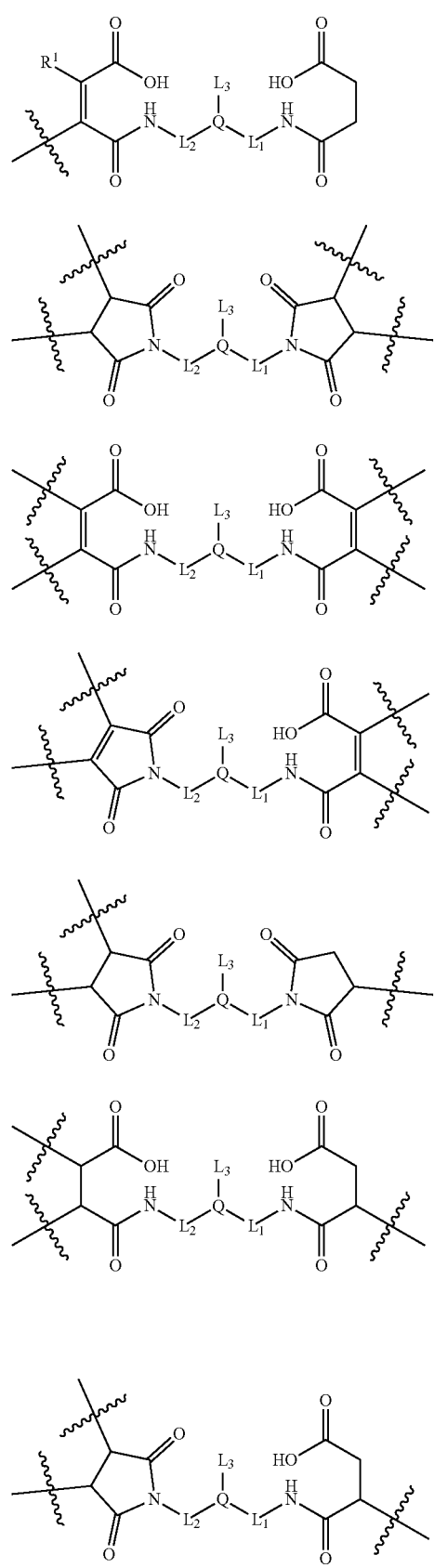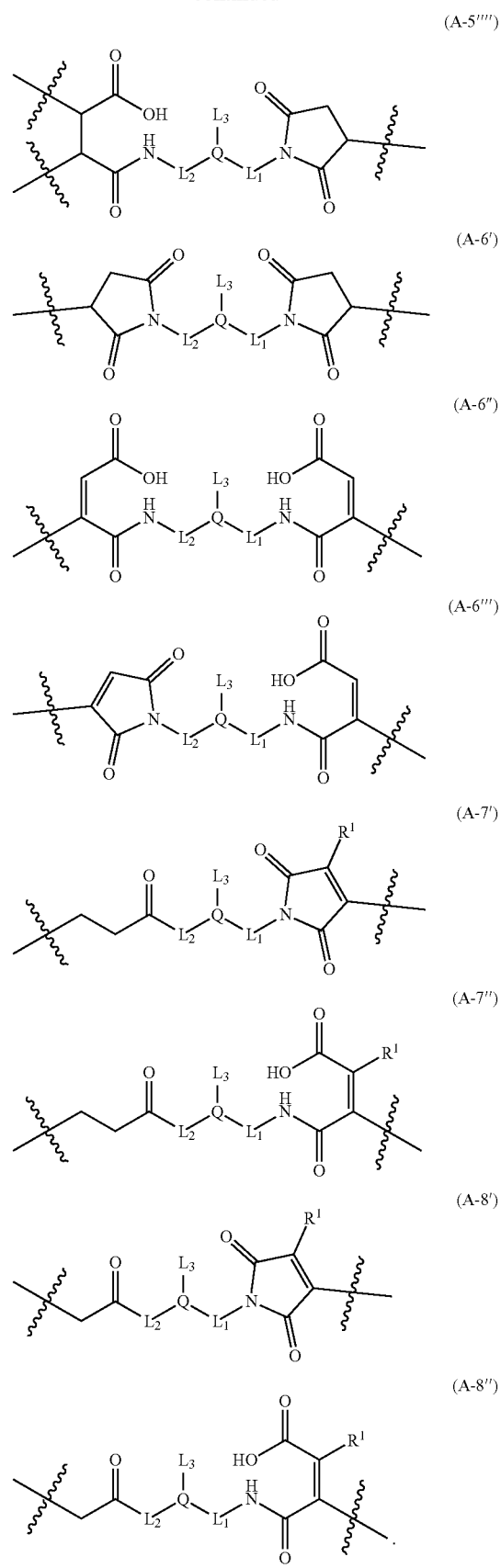

Still furthermore, the antibody or functional fragment of the antibody specifically binds to cell surface receptors or tumor-related antigens.
Still furthermore, the first linker moiety A includes a group that is covalently linked to the thiol group or amino group in the Ab.
Still furthermore, the first linker moiety A may have the structure:
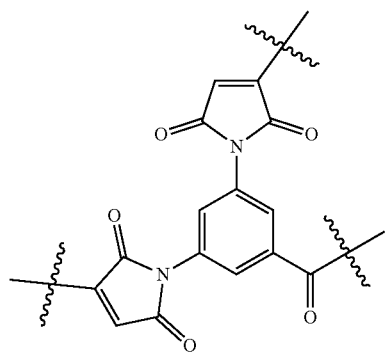
A-1
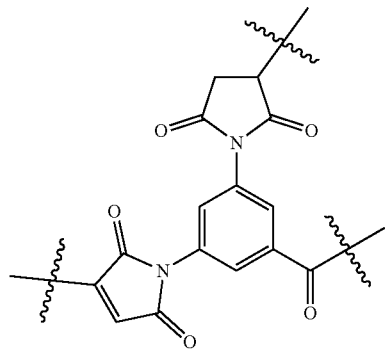
A-2
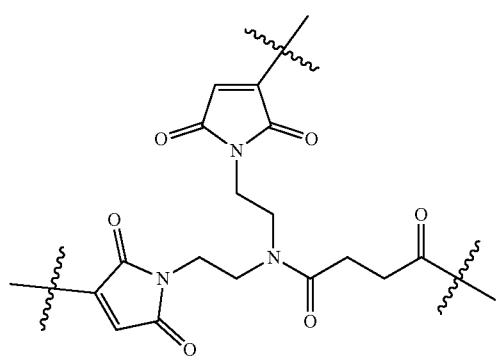
A-4
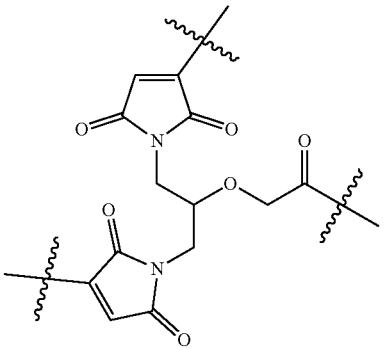
A-5
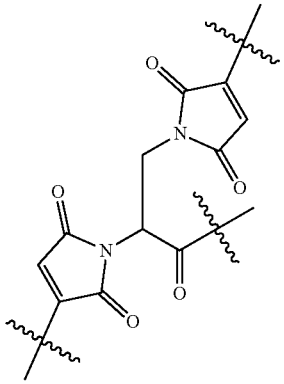
A-6
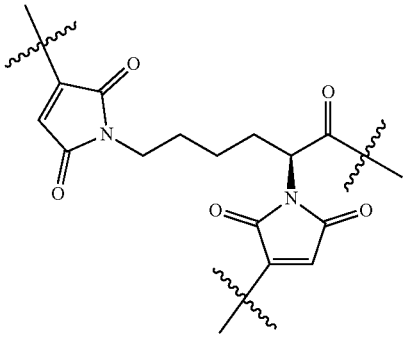
A-7
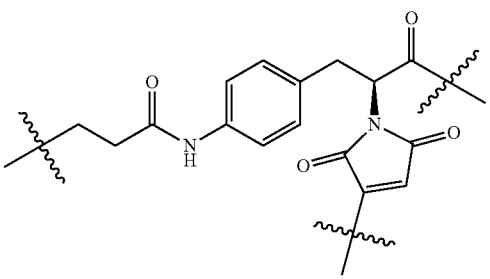
A-10

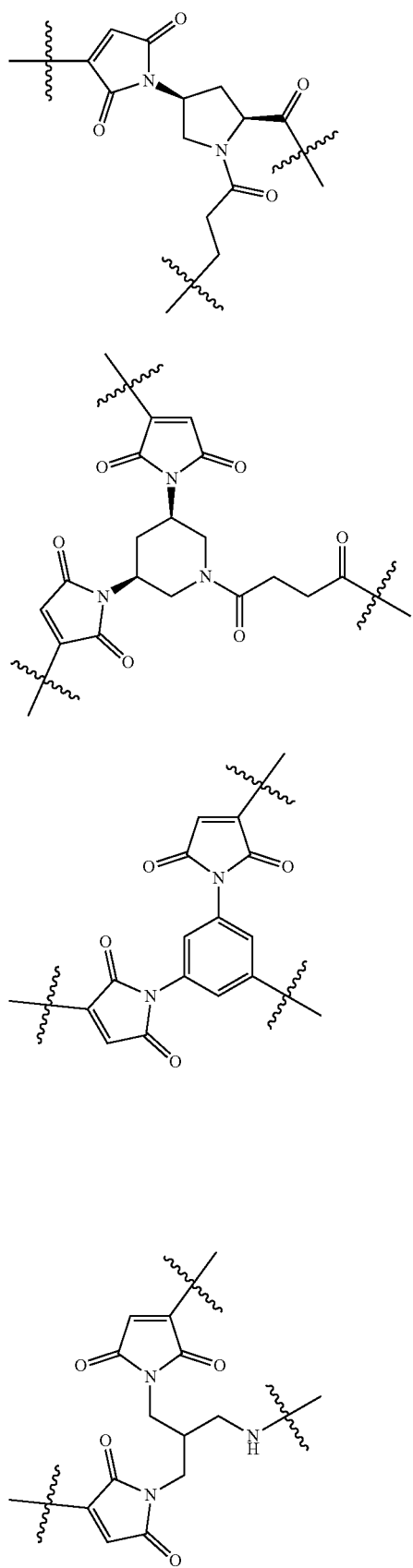
A-11
A-12
A-13
A-15
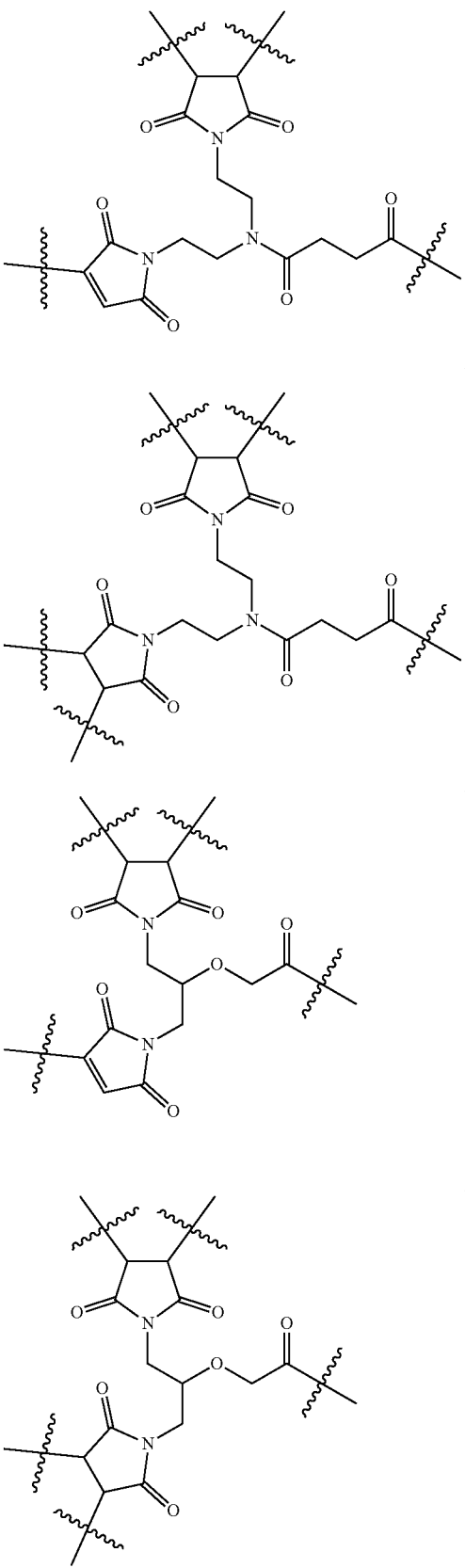
A-16
A-17
A-18
A-19

-continued
A-20
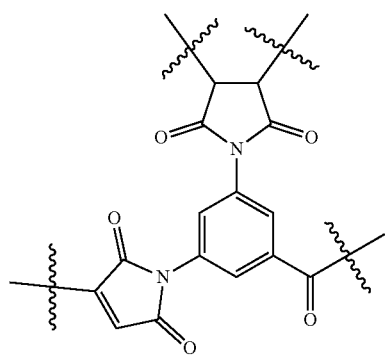
A-21
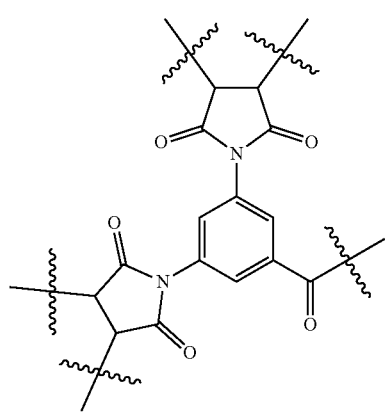
A-23
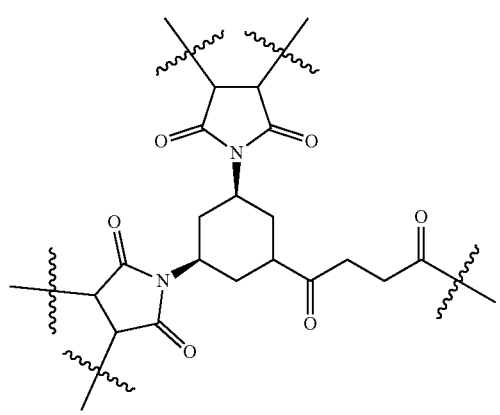
A-24
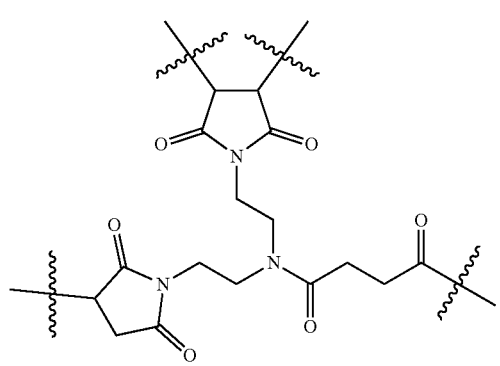
-continued
A-25
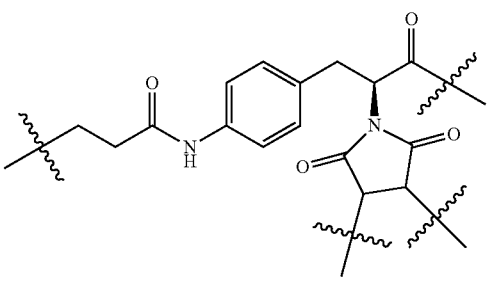
A-28
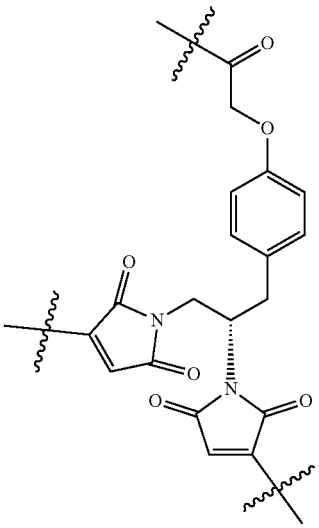
A-29
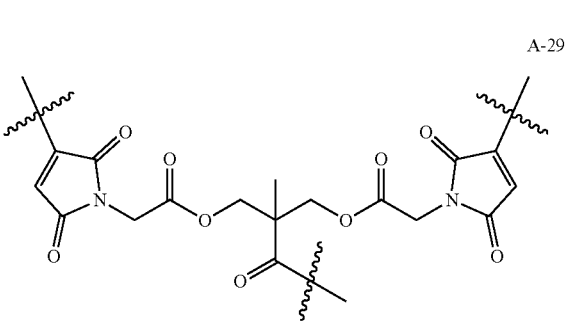
A-31
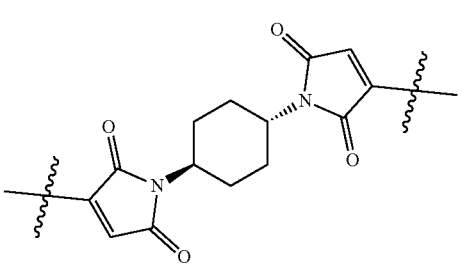

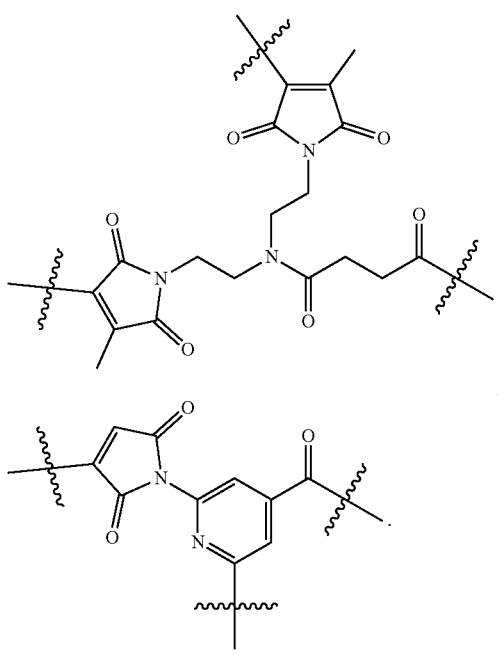

A-33

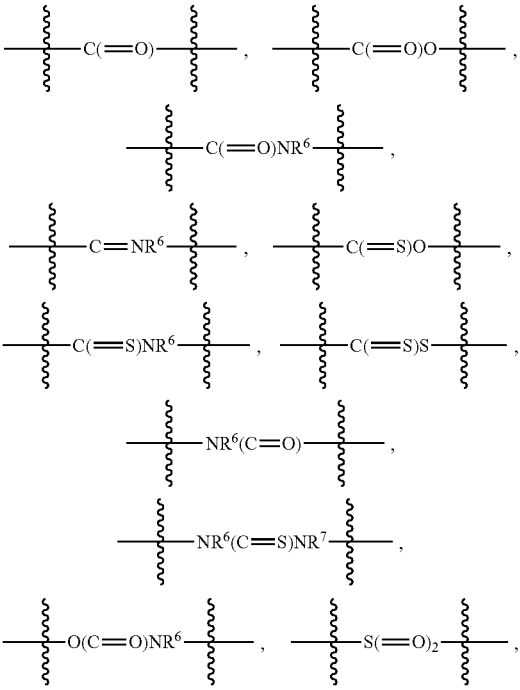

A-34

Still furthermore, the second linker moiety L may be: $C_1$-$C_9$ alkyl, $C_2$-$C_9$ alkenyl, $C_2$-$C_9$ alkynyl, aryl, heteroaryl, $C_3$-$C_9$ cycloalkyl, $C_3$-$C_9$ heterocyclyl,

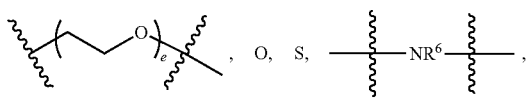, O, S,

Val-Val-PAB, Val-Cit-PAB, Val-Ala-PAB, Val-Lys (Ac)-PAB, Phe-Lys-PAB, Phe-Lys (Ac)-PAB, D-Val-Leu-Lys, Gly-Gly-Arg, Ala-Ala-Asn-PAB, Ala-PAB, PAB and any combination thereof or is absent, wherein, $R^6$, $R^7$ each are independently selected from H, $C_1$-$C_6$ alkyl, $C_2$-$C_6$ alkenyl, $C_2$-$C_6$ alkynyl, aryl, heteroaryl, $C_3$-$C_9$ cycloalkyl, $C_3$-$C_9$ heterocyclyl, e is 0, 1, 2, 3, 4, 5, 6, 7 or 8.

Preferably, the second linker moiety L may be:

L-1

L-2

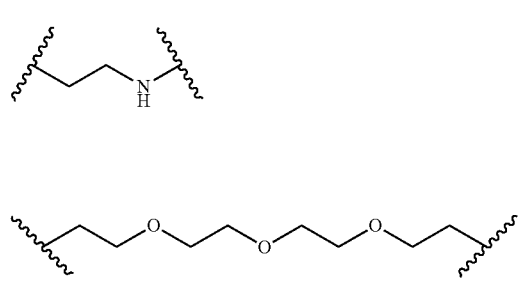

L-3

L-4

L-5

L-6

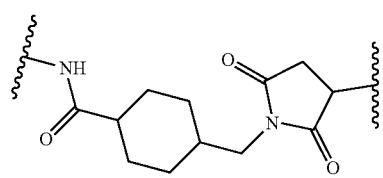

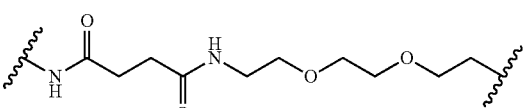

-continued
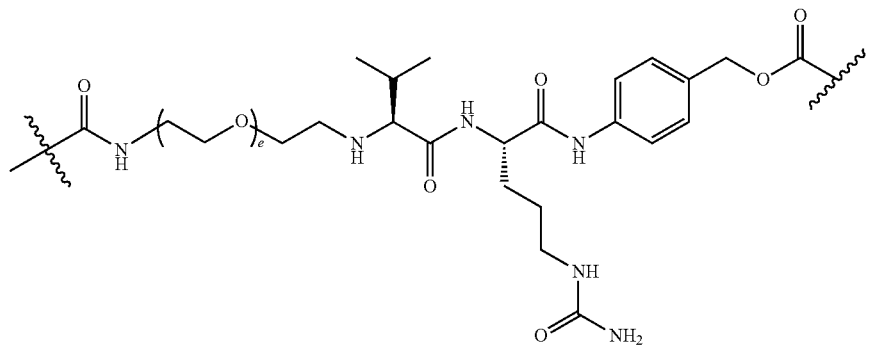
L-7
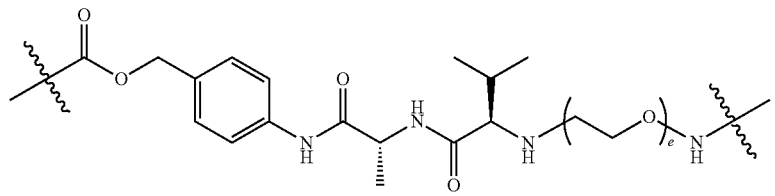
L-8
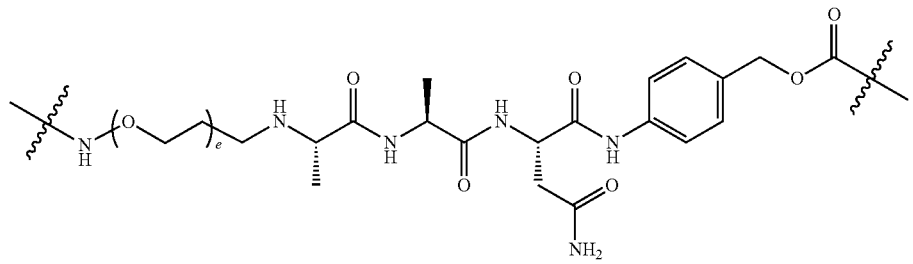
L-9
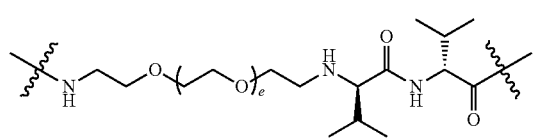
L10
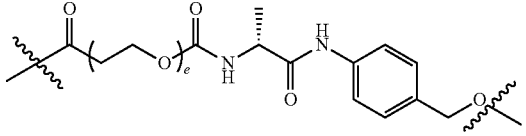
L11
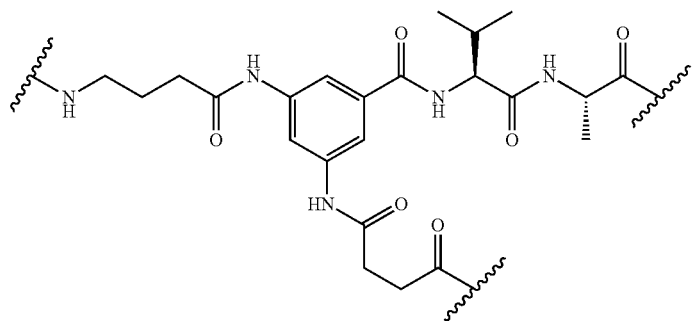
L-12

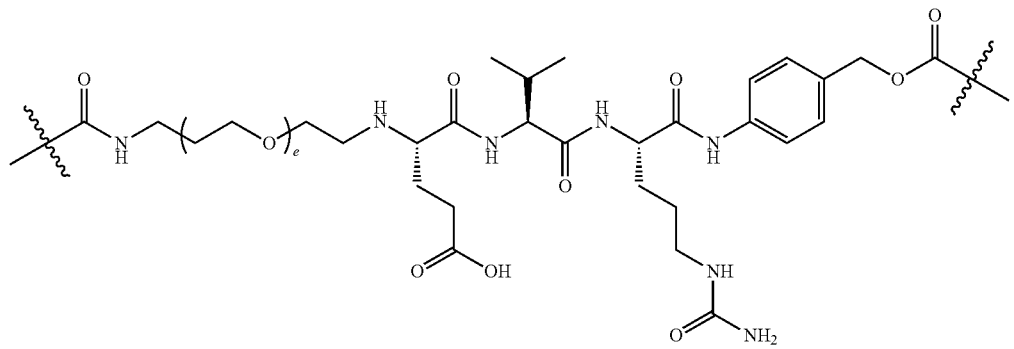

L-13

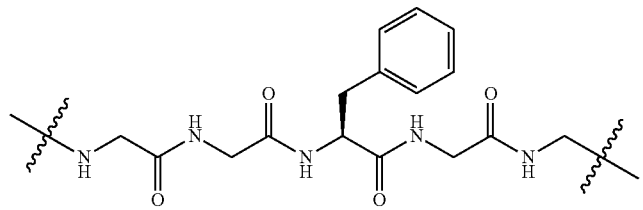

L-14

Still furthermore, the drug moiety is selected from cytotoxic drugs, cell differentiation factors, stem cell nutritional factors, steroid drugs, drugs for the treatment of autoimmune diseases, anti-inflammatory drugs or drugs for the treatment of infectious diseases.

Still furthermore, the drug moiety includes, but not limited to, tubulin inhibitors or DNA damaging agents.

Still furthermore, the tubulin inhibitor includes, but not limited to, dolastatins, auristatins, maytansines; the DNA damaging agent includes, but not limited to, calicheamicins, duocarmycins, anthramycin derivatives PBD, camptothecin derivatives (preferably camptothecin derivative SN-38), topoisomerase I inhibitors (i.e., Dxd).

Still furthermore, the drug moiety includes, but not limited to, amanitins, anthracyclines, baccatins, camptothecins, cemadotins, colchicines, colcimids, combretastatins, cryptophycins, discodermolides, docetaxel, doxorubicin, echinomycins, eleutherobins, epothilones, estramustines, lexitropsins, maytansines, methotrexate, netropsins, puromycins, rhizoxins, taxanes, tubulysins, or vinca alkaloids, vitamin A precursor, folic acid, camptothecin derivatives SN-38, topoisomerase I inhibitors (i.e., Dxd).

Preferably, the drug moiety D may be:

D-1

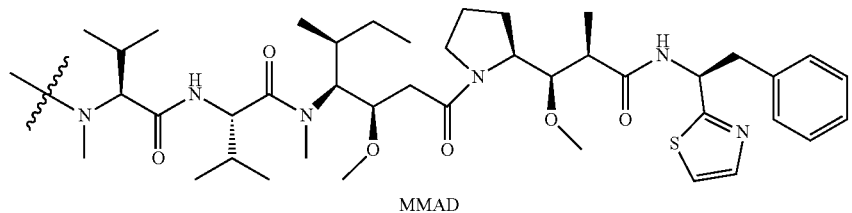

MMAD

D-2

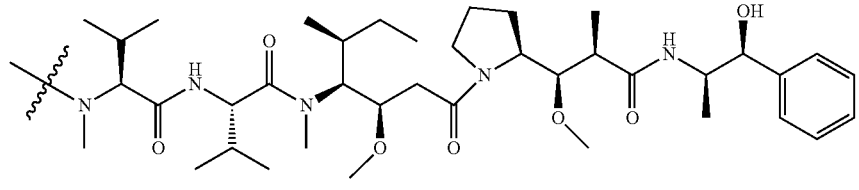

MMAE

D-3

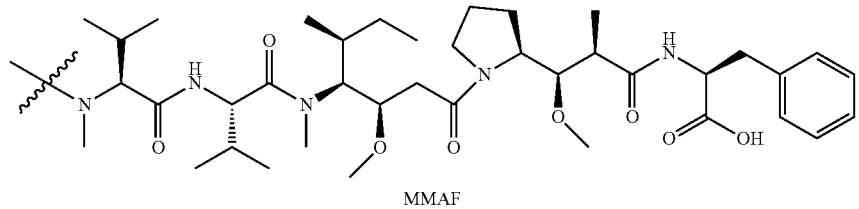

MMAF

-continued
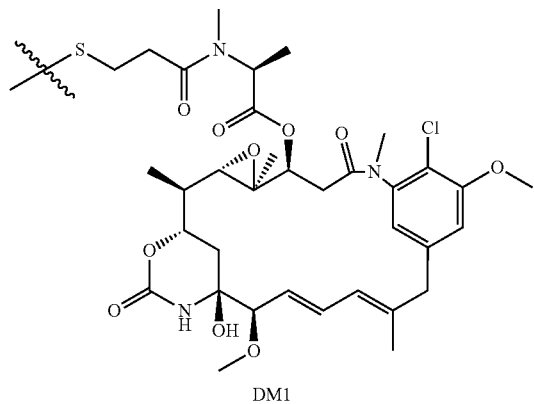
DM1  D-4
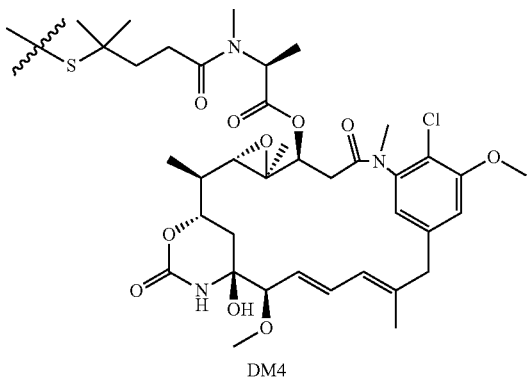
DM4  D-5
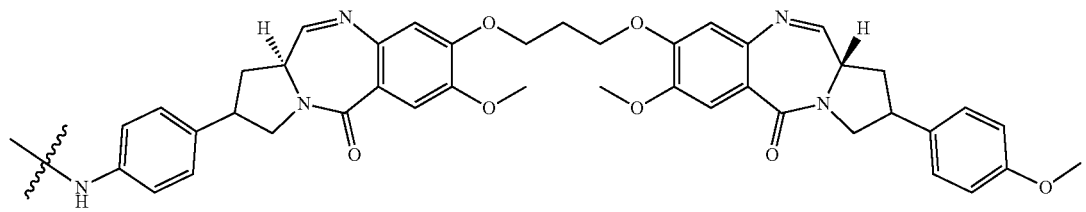
PBD  D-6
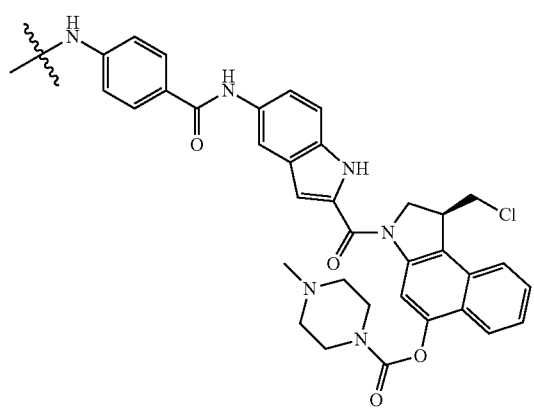
CBI  D-7
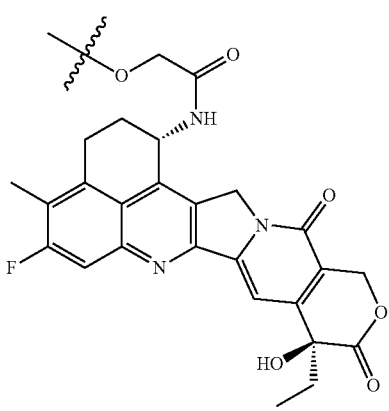
Dxd  D-8
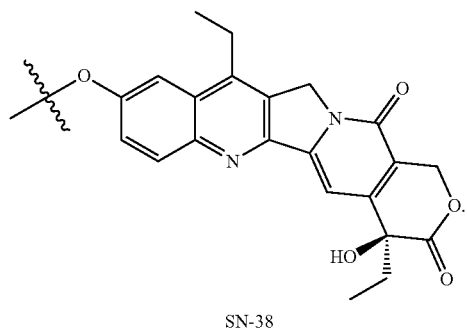
SN-38  D-9

In some preferred examples, the antibody-drug conjugate has the structure:
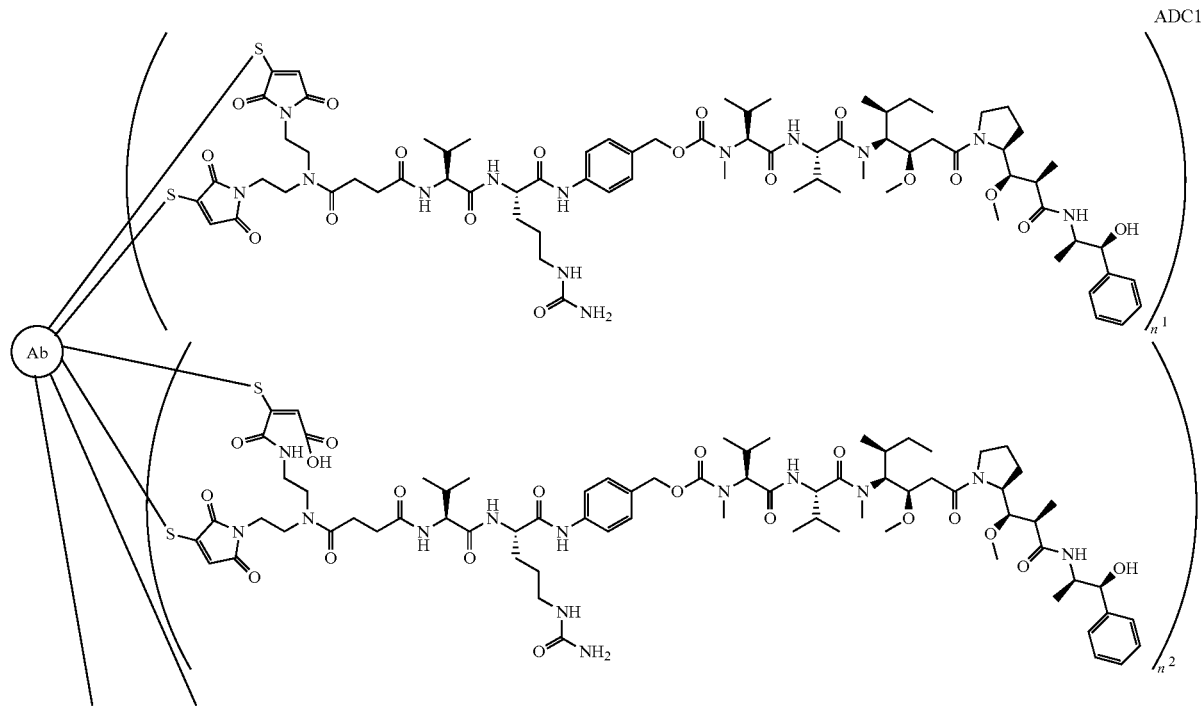
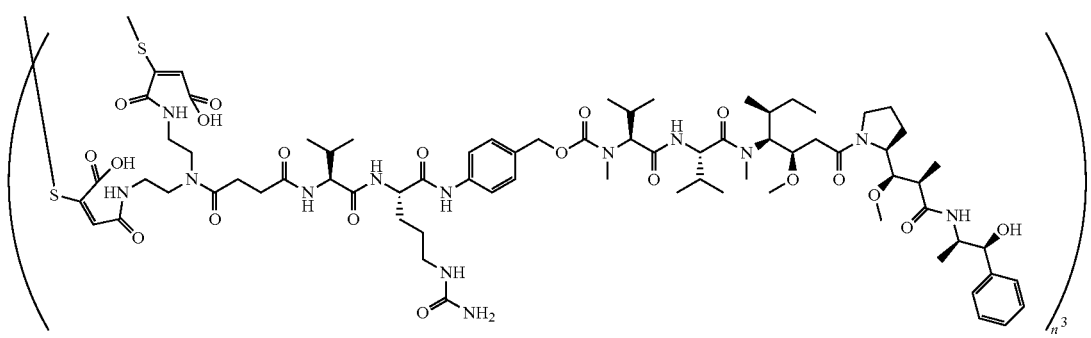

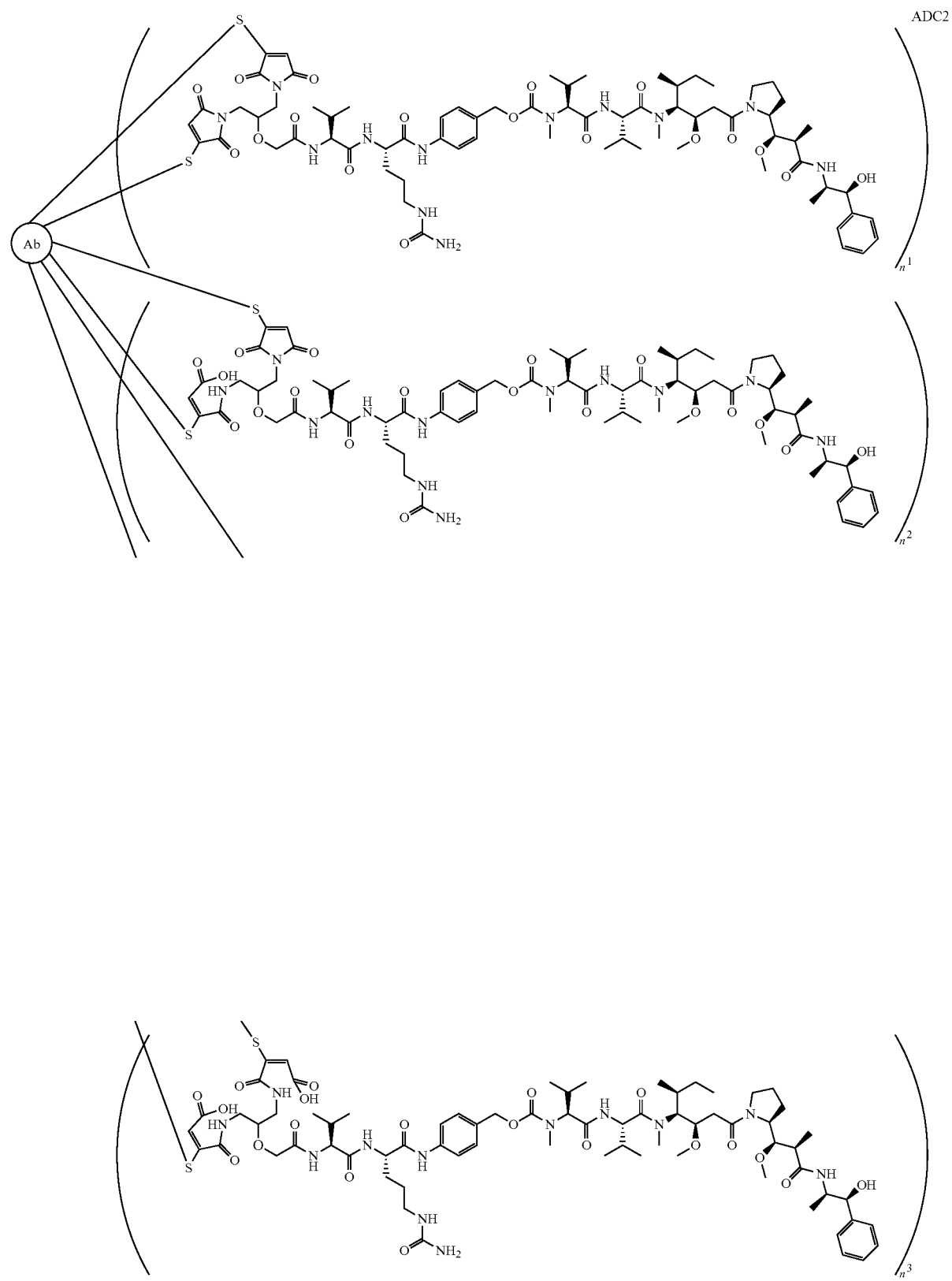

-continued
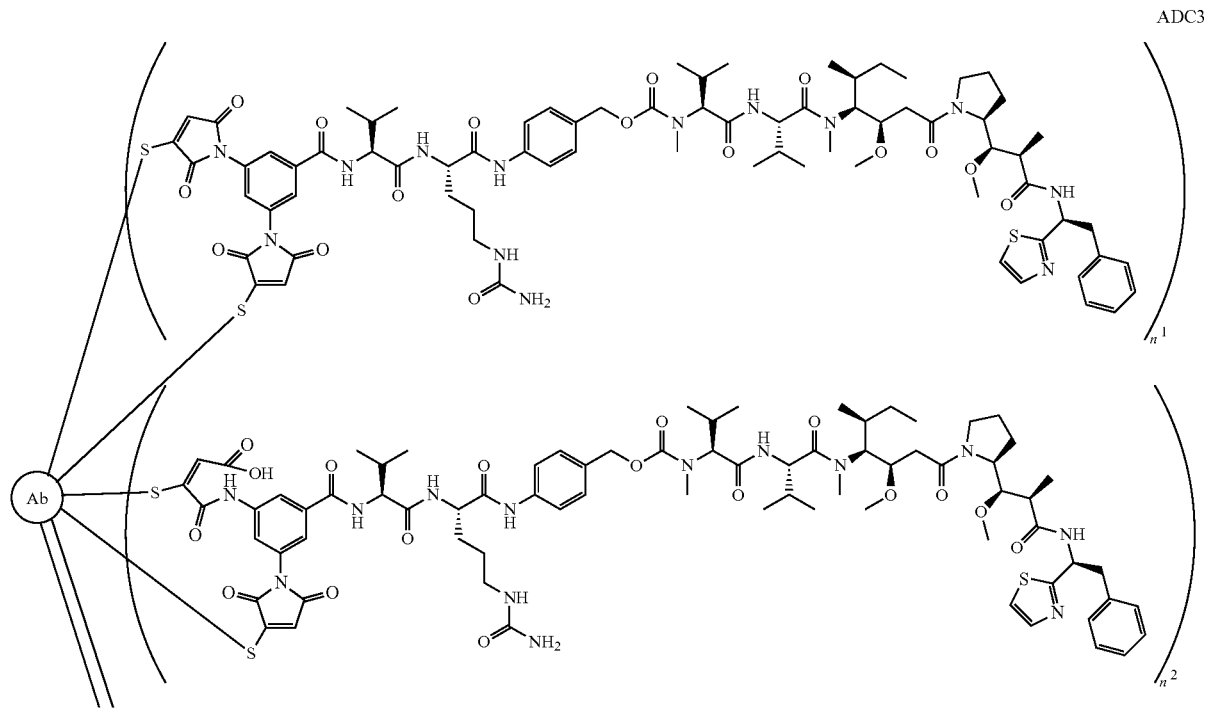
ADC3
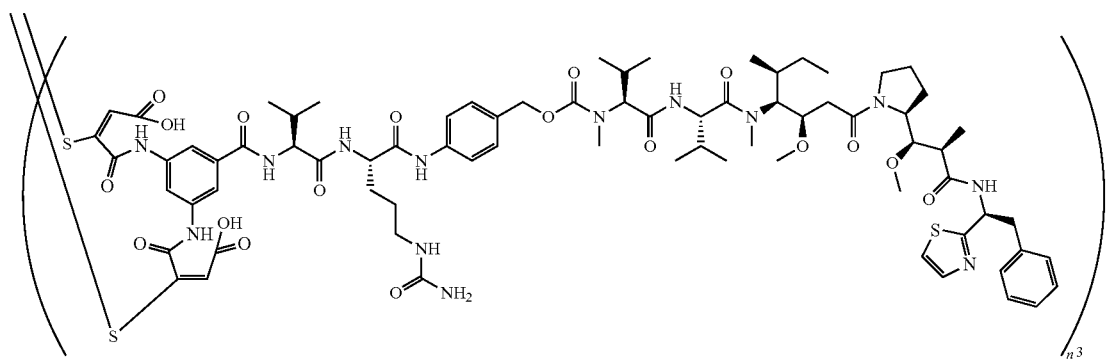

-continued
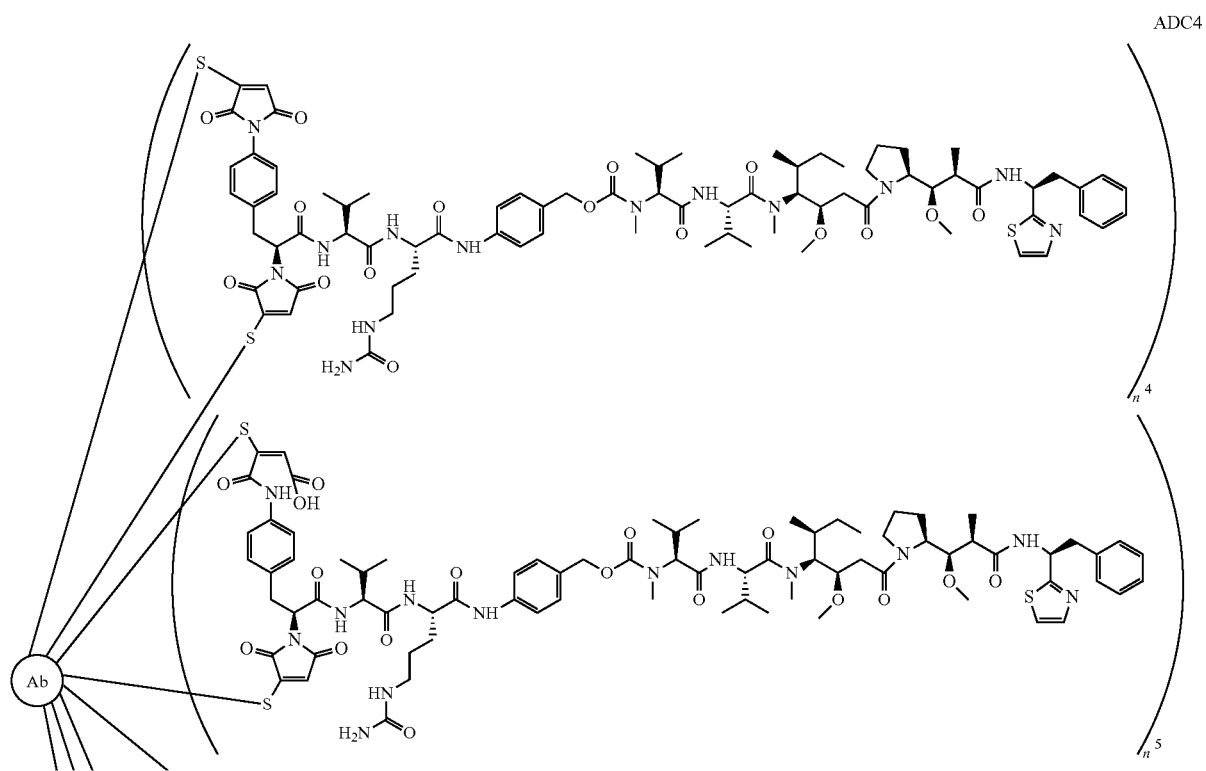
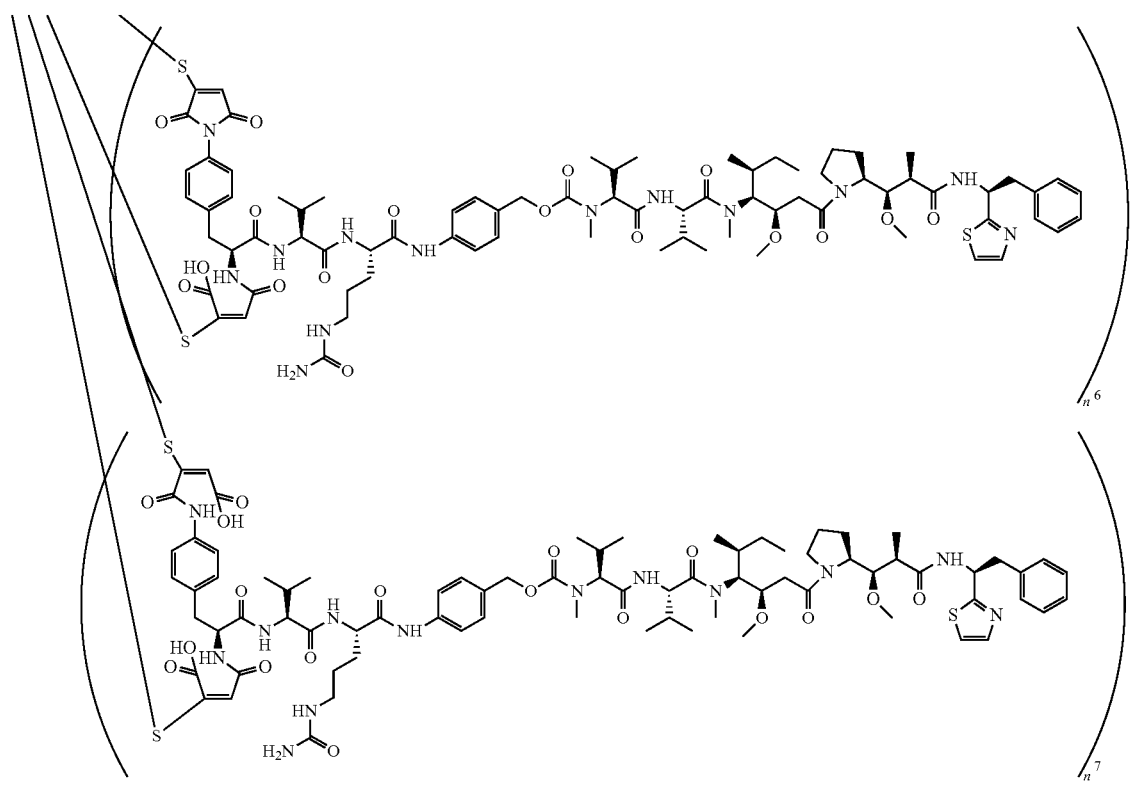

-continued
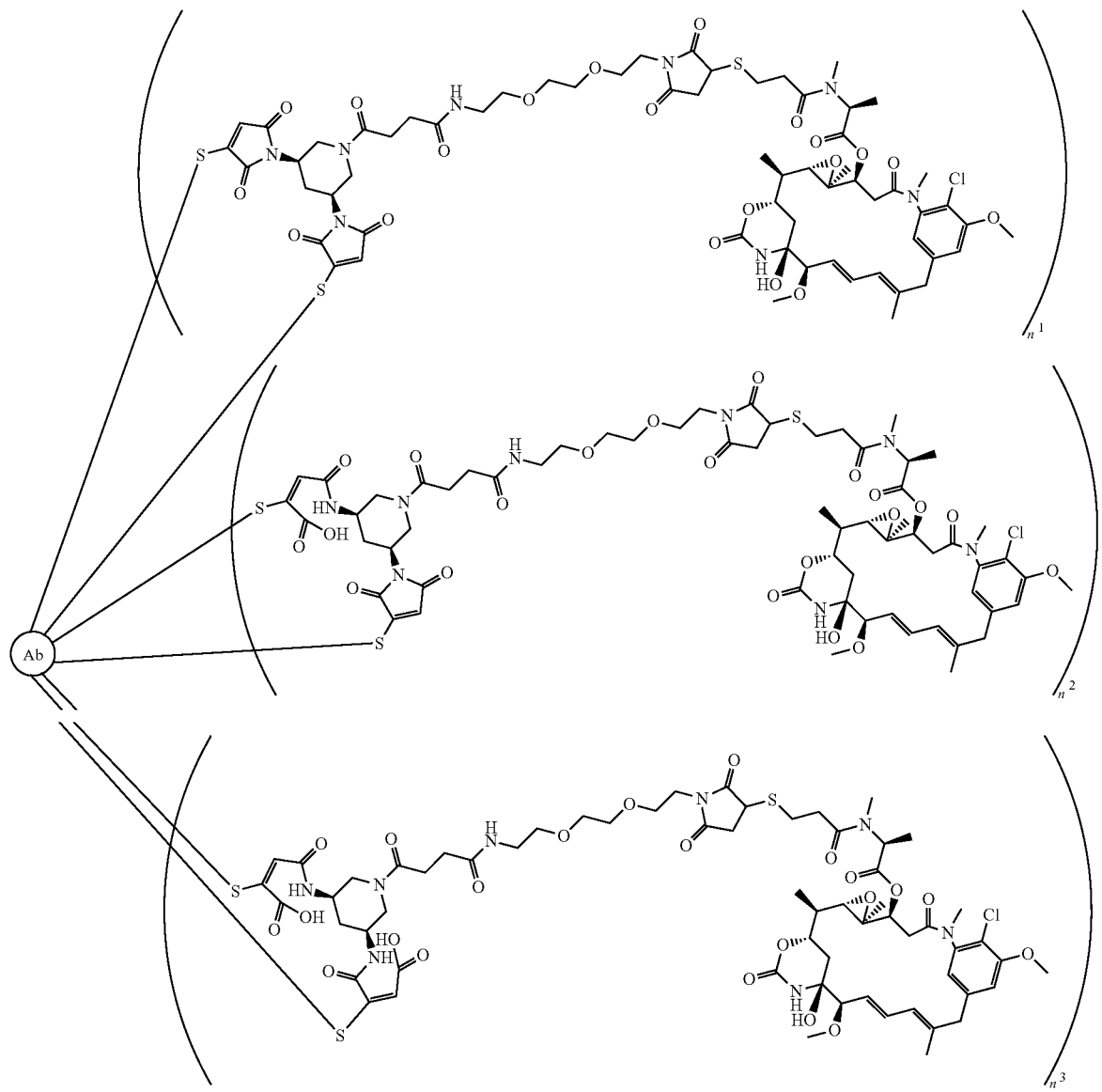
ADC5
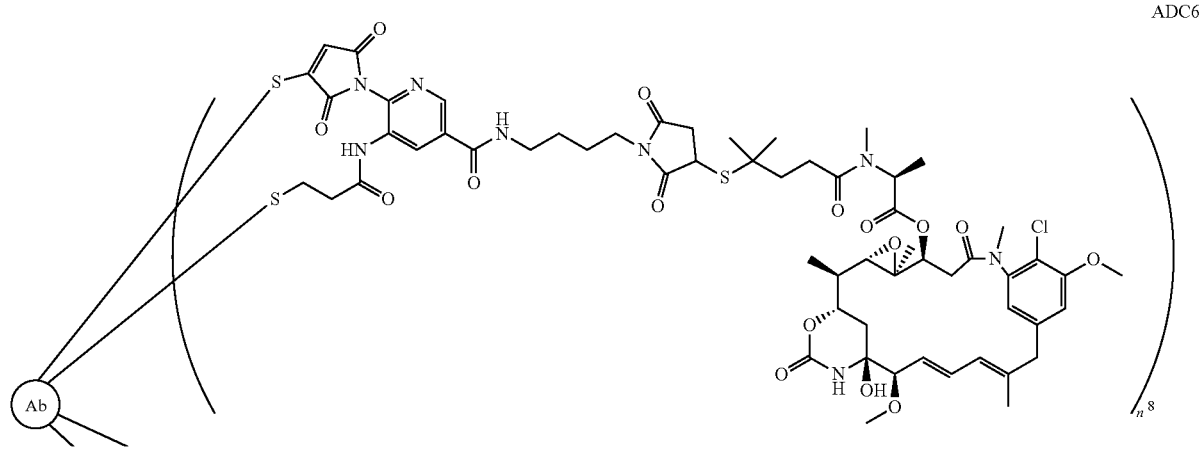
ADC6

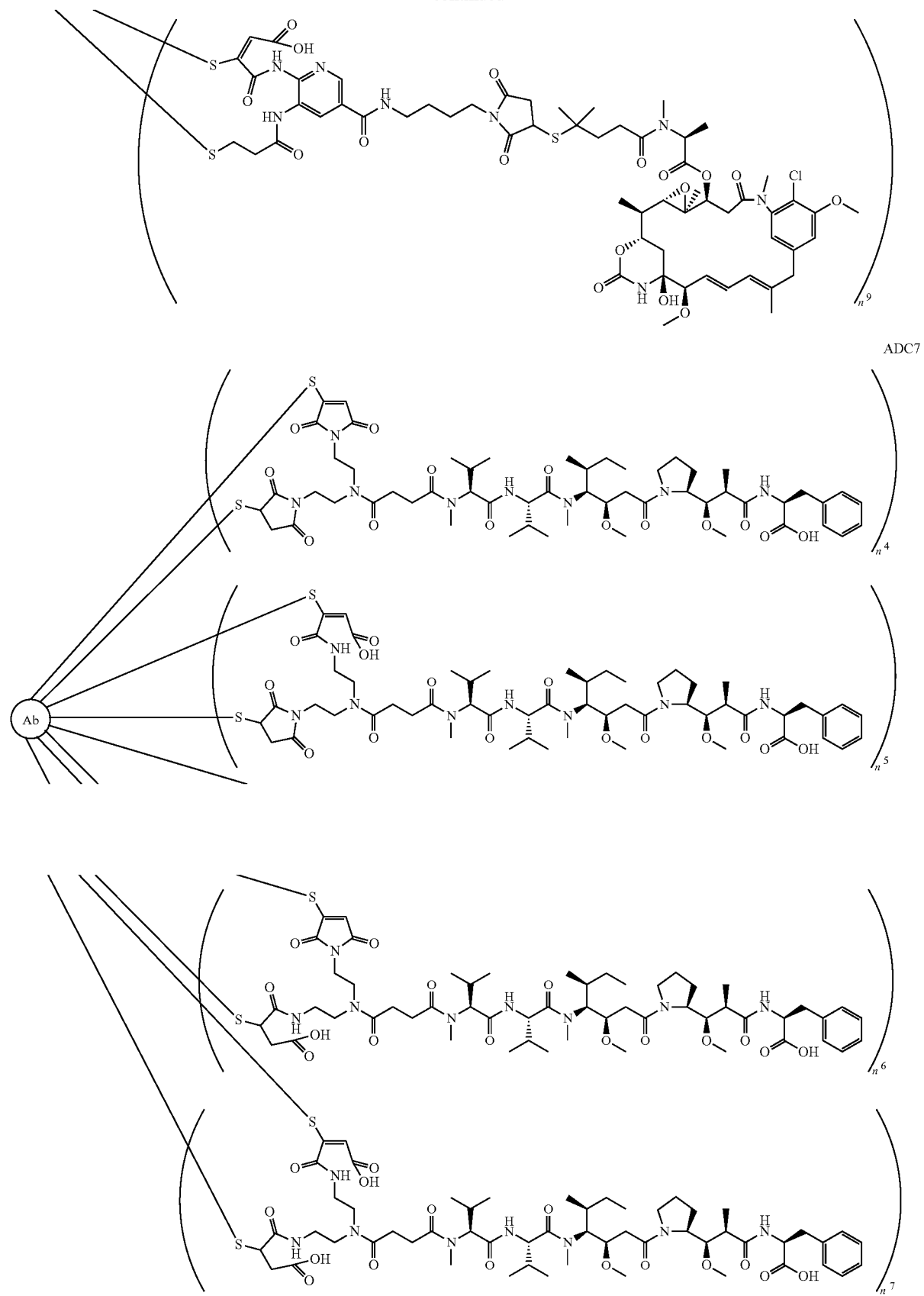

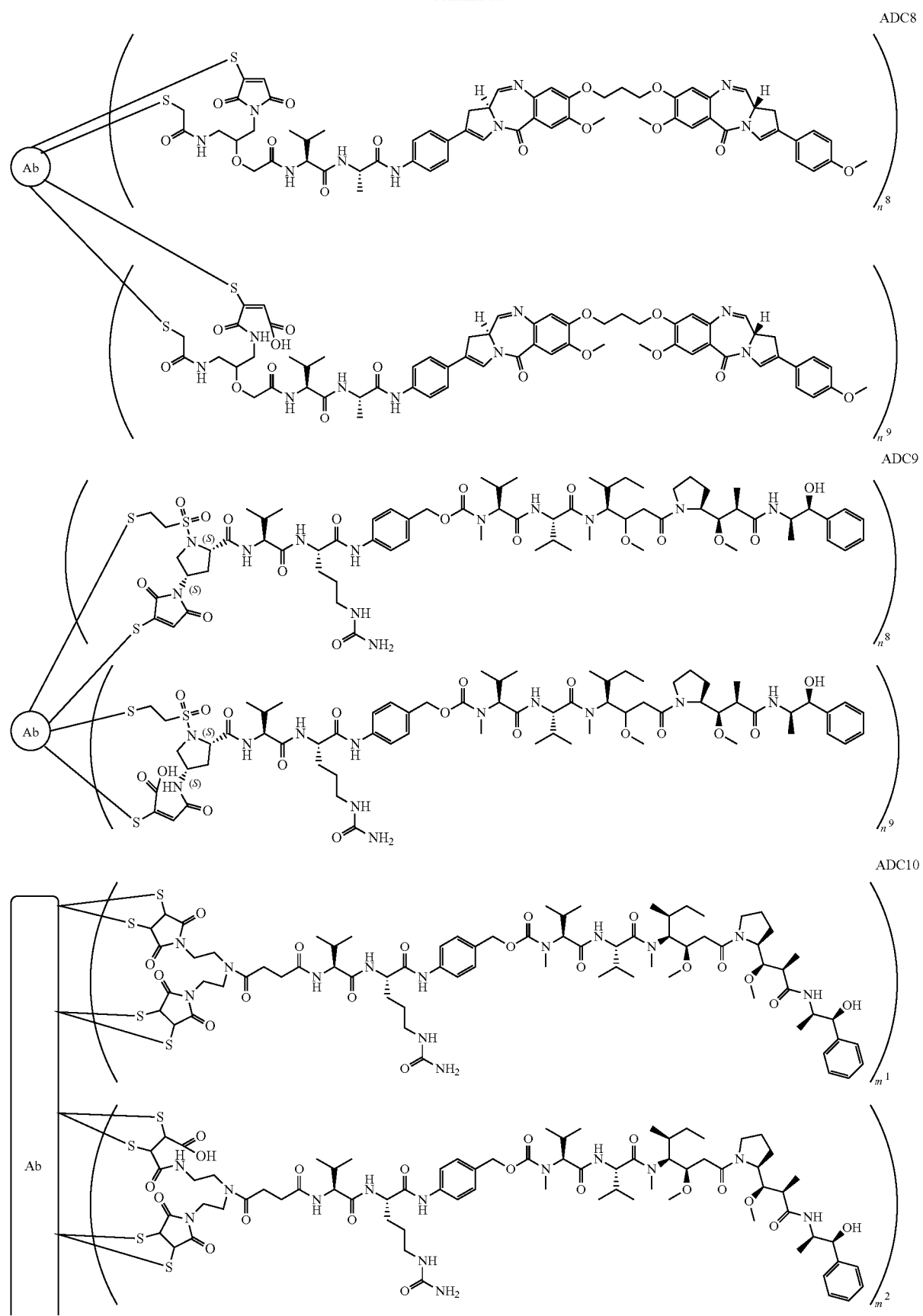

-continued
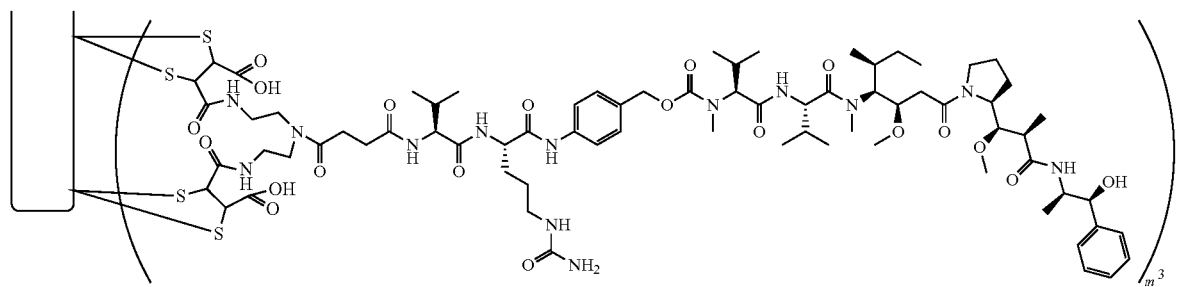
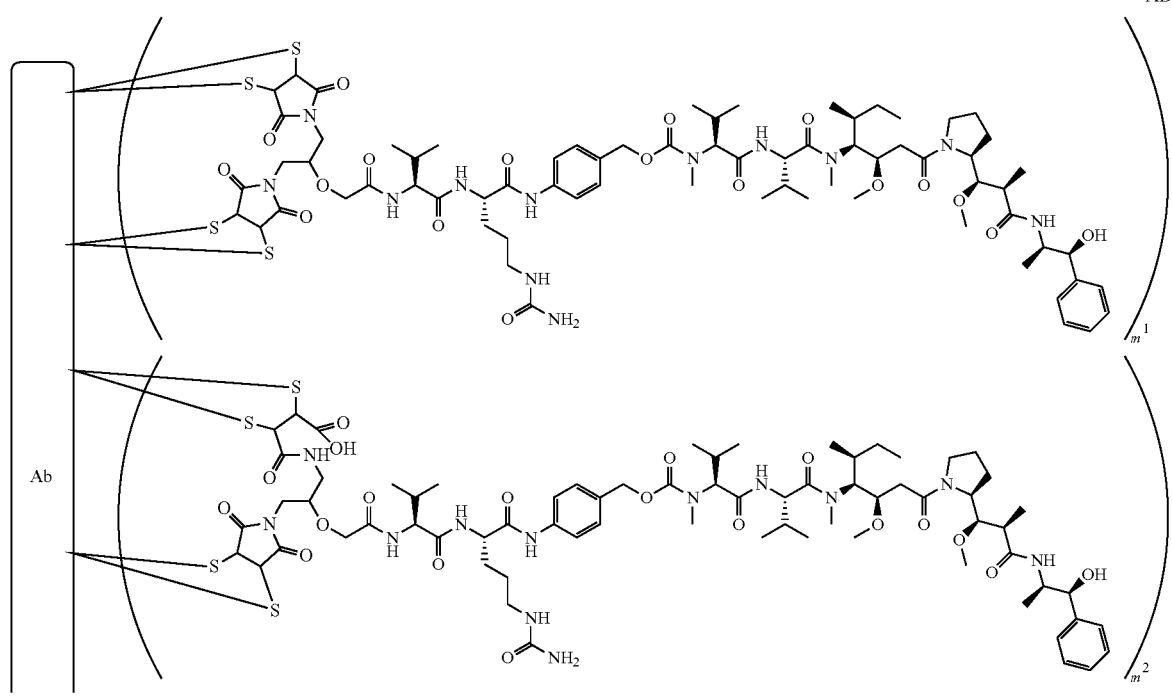
ADC11
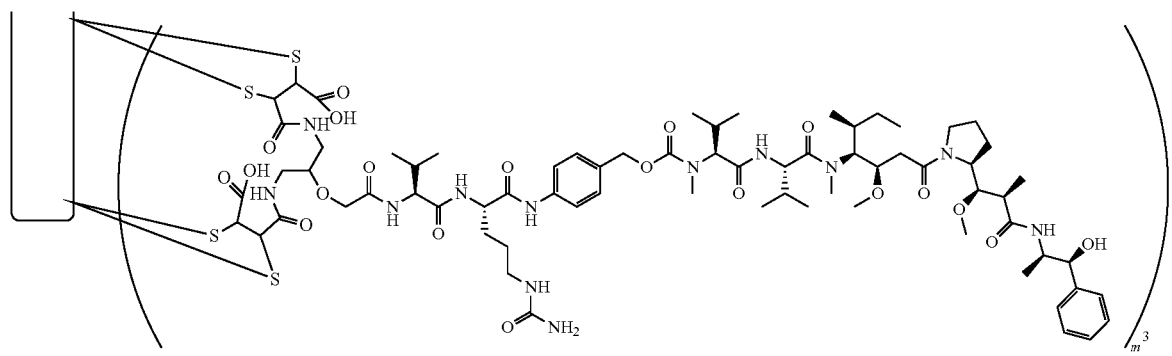

-continued
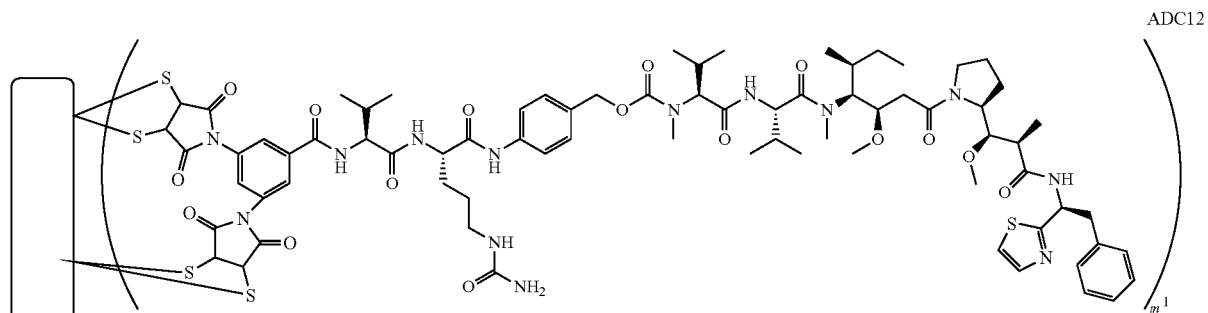
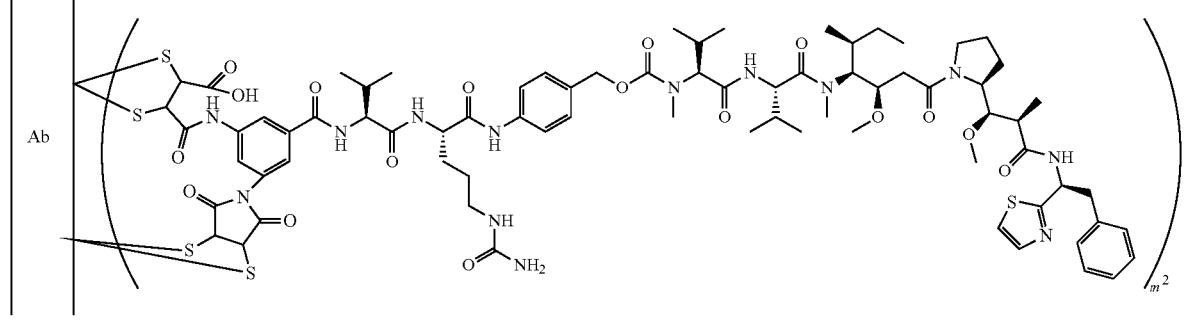
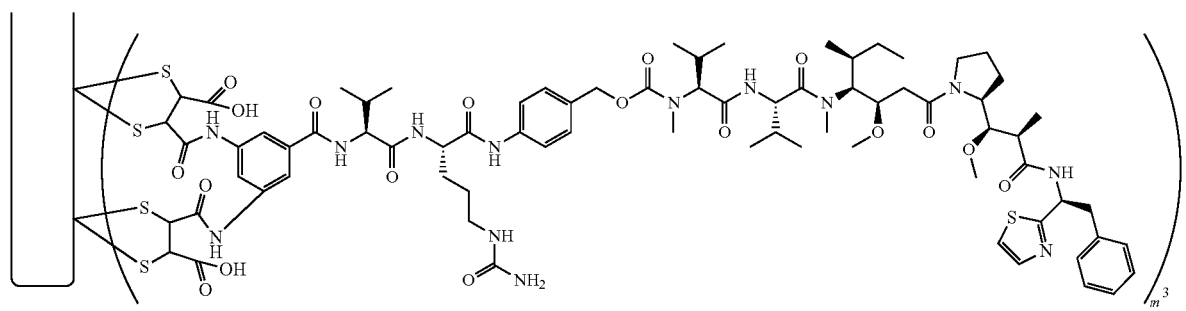

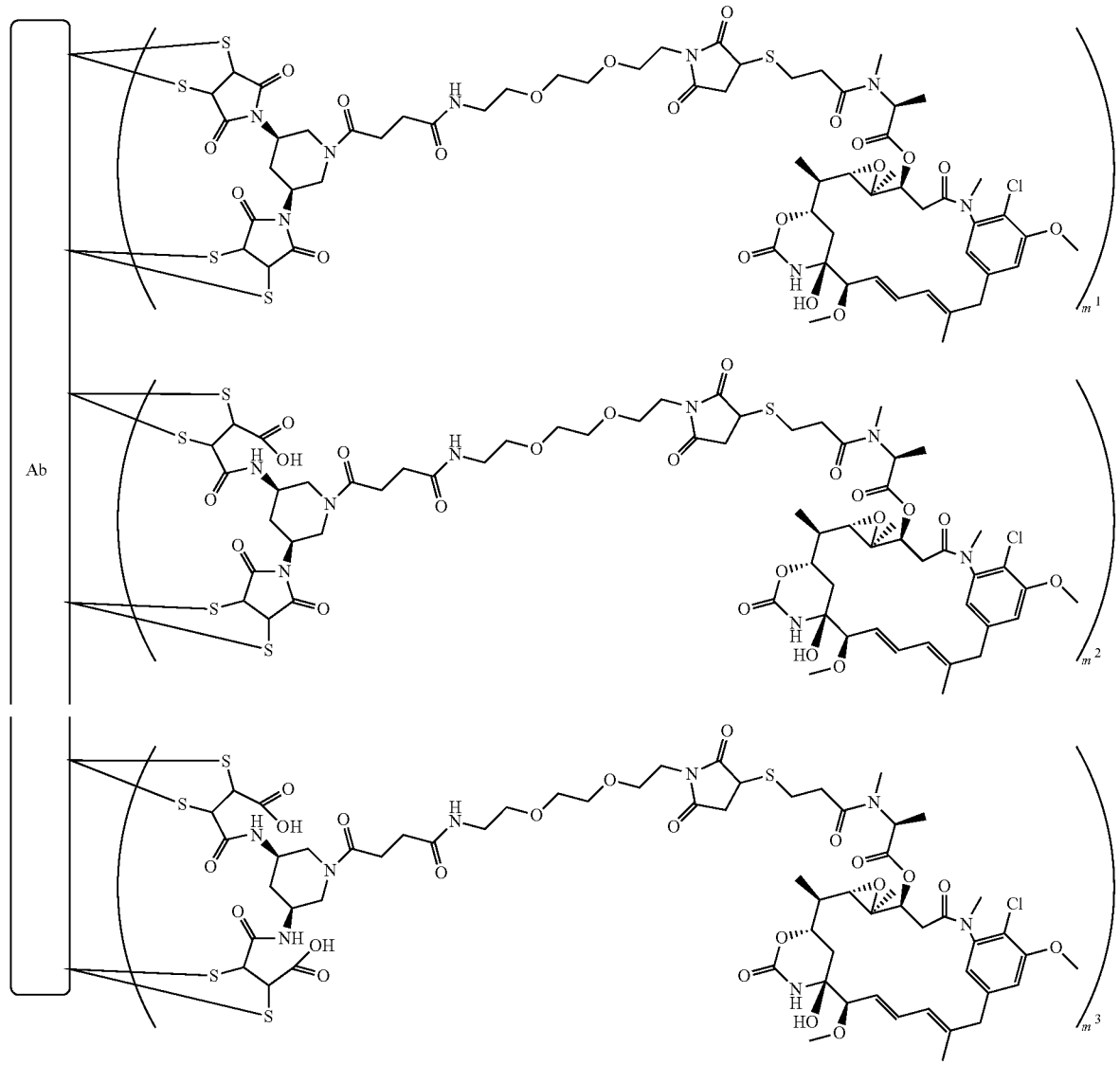
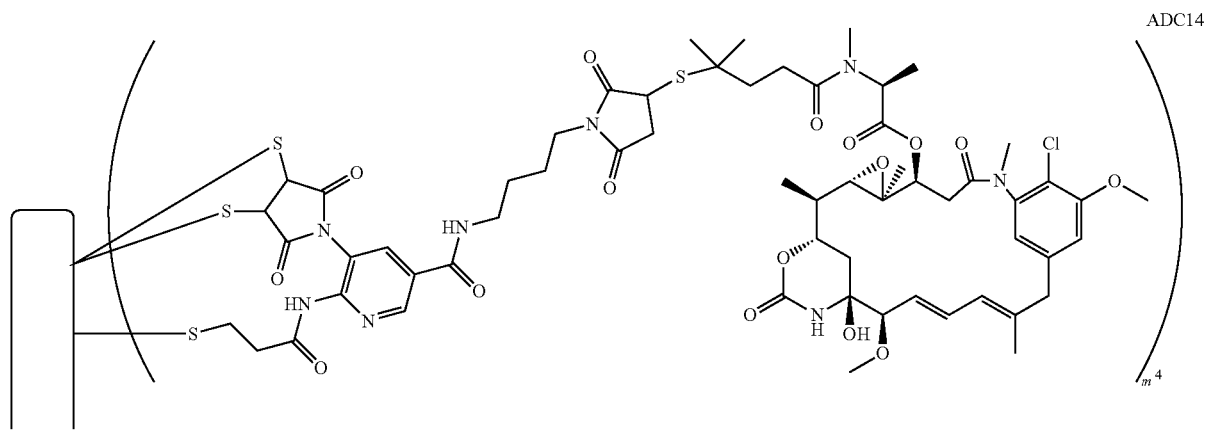

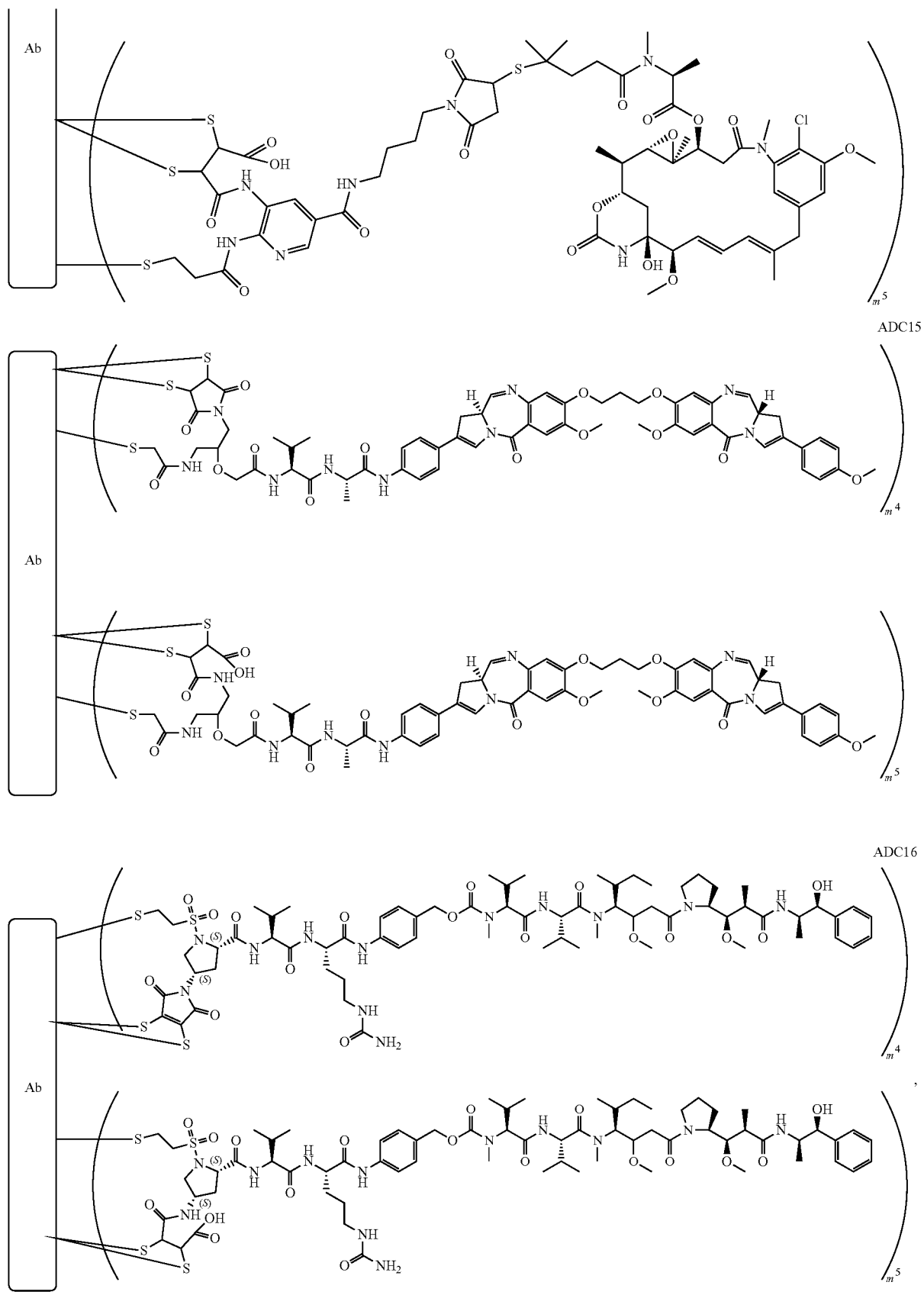

wherein:
the antibody or functional fragment of the antibody, Ab, is an antibody against cell surface receptors and tumor-related antigens;
$n^1, n^2, n^3$ each are independently selected from 0, 1, 2, 3, 4; $n^1, n^2, n^3$ are not 0 at the same time, and $n^1+n^2+n^3 \leq 4$;
$n^4, n^5, n^6, n^7$ each are independently selected from 0, 1, 2, 3, 4; $n^4, n^5, n^6, n^7$ are not 0 at the same time, and $n^4+n^5+n^6+n^7 \leq 4$;
$n^8, n^9$ each are independently selected from 0, 1, 2, 3, 4; $n^8, n^9$ are not 0 at the same time, and $n^8+n^9 \leq 4$;
$m^1, m^2, m^3$ each are independently selected from 0, 1, 2; at least one of $m^1, m^2, m^3$ is 0, but $m^1, m^2, m^3$ are not 0 at the same time, and $m^1+m^2+m^3 \leq 2$;
$m^4, m^5$ each are independently selected from 0, 1, 2; $m^4, m^5$ are not 0 at the same time, and $m^4+m^5 \leq 2$.

Furthermore, the antibody-drug conjugate has the structure:

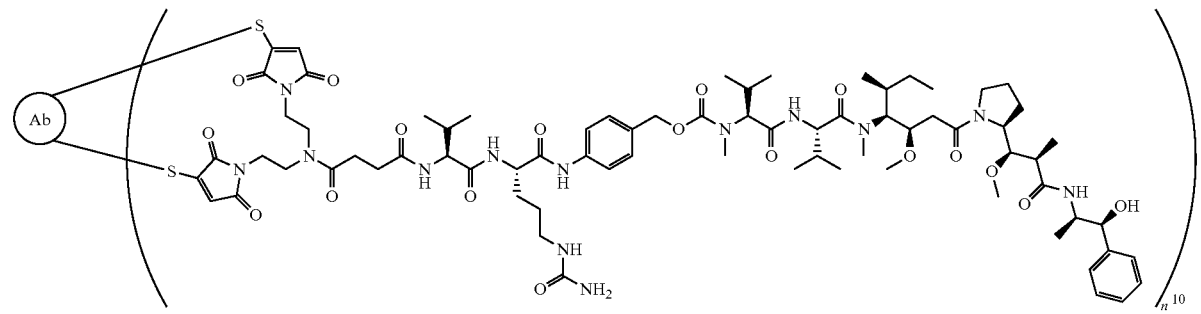

ADC17

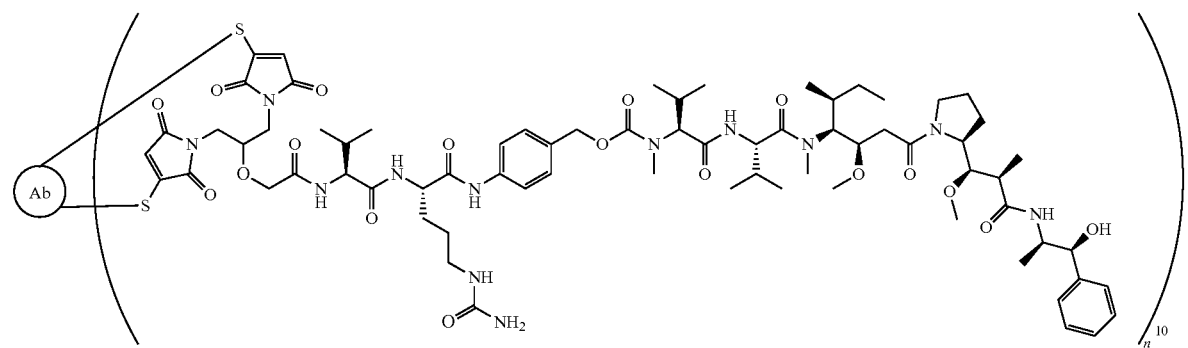

ADC18

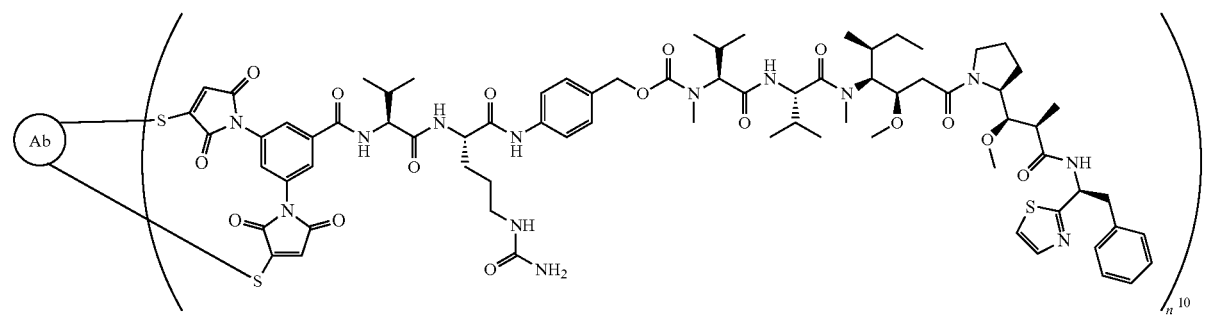

ADC19

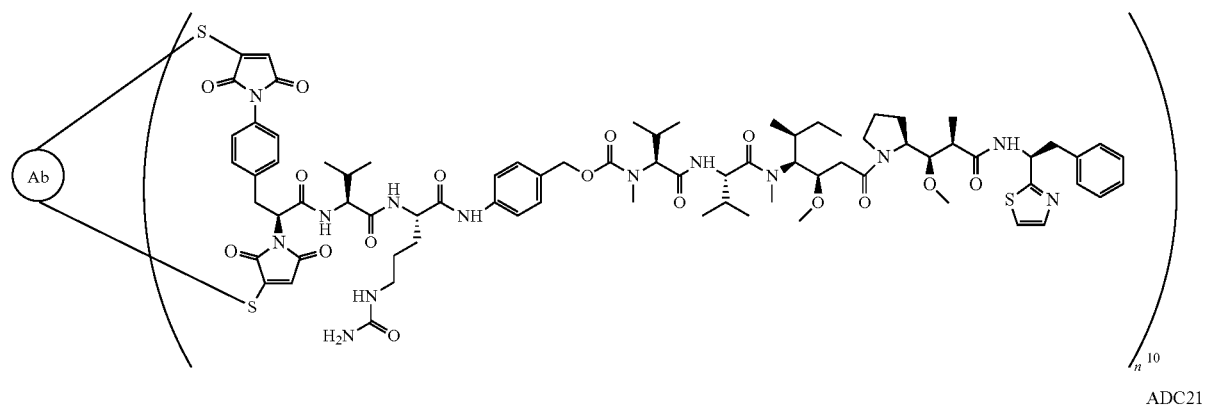
ADC20
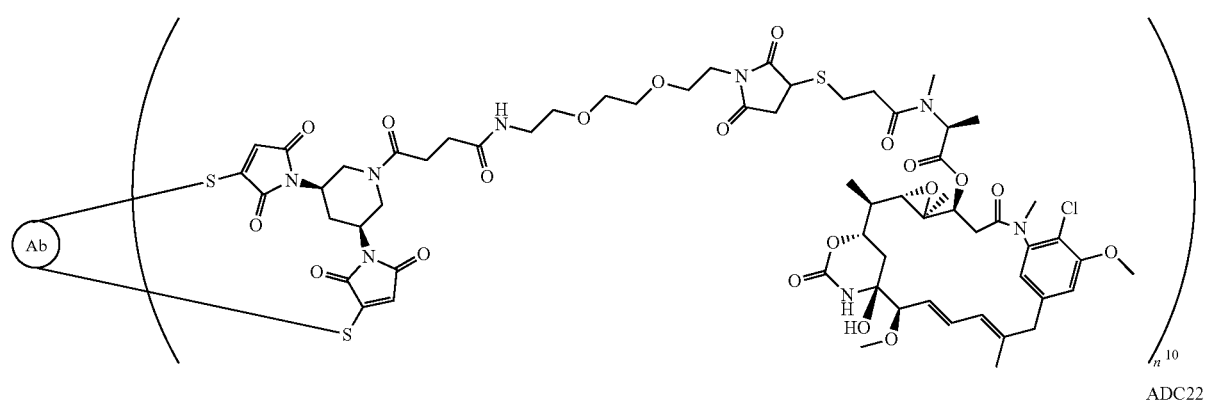
ADC21
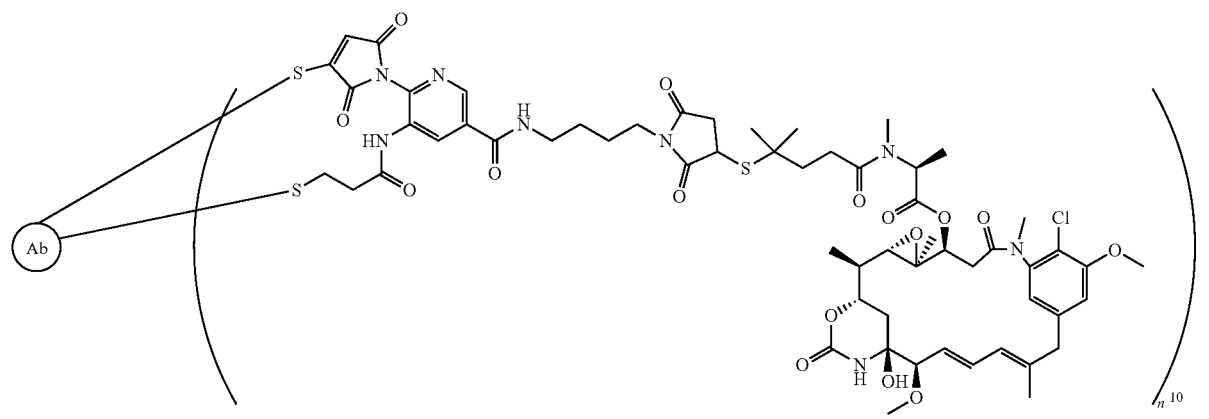
ADC22
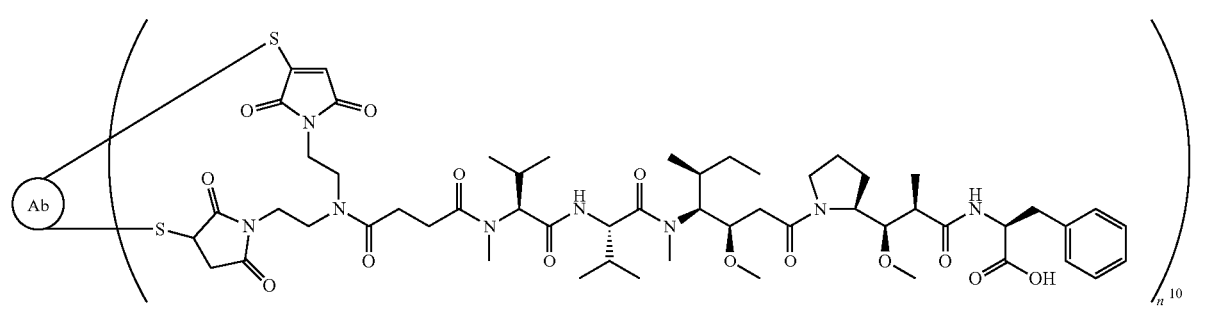
ADC23

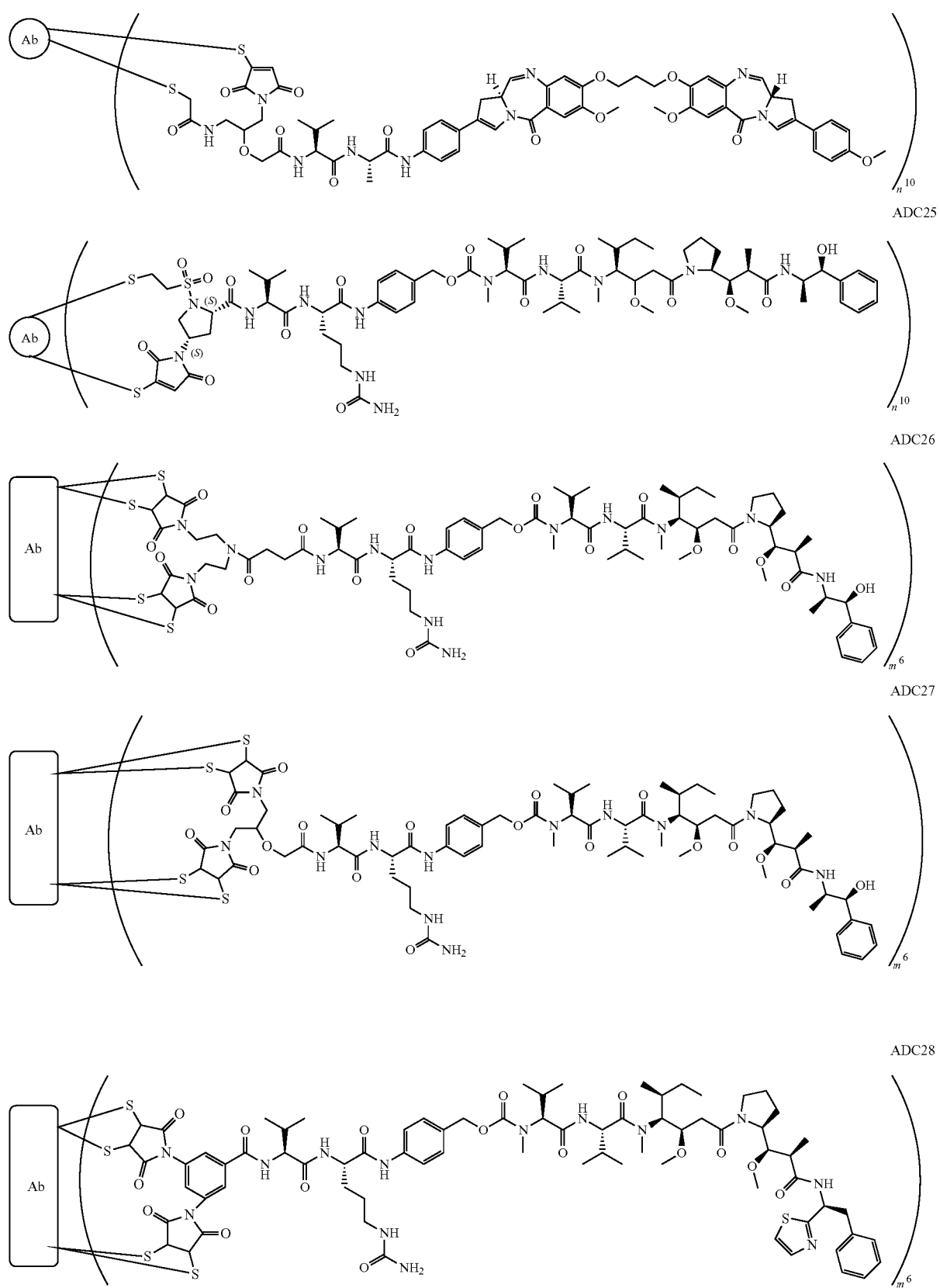

-continued
ADC29
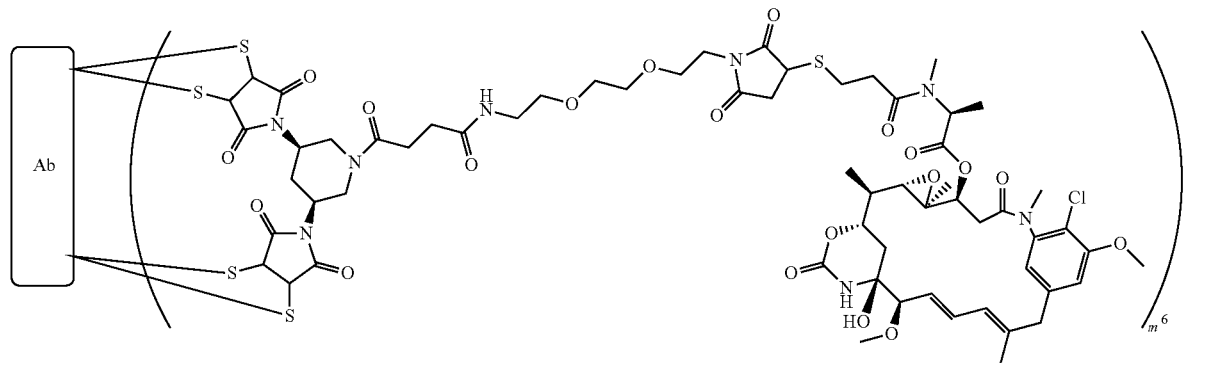
ADC30
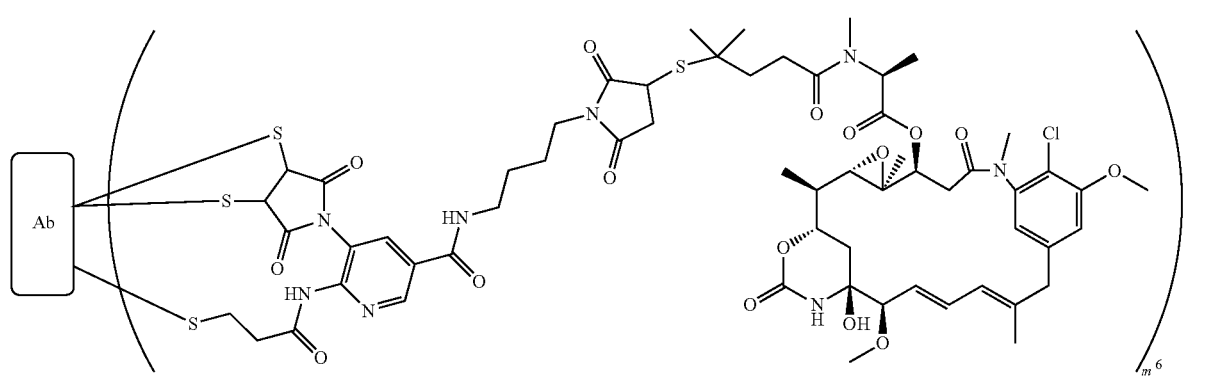
ADC31
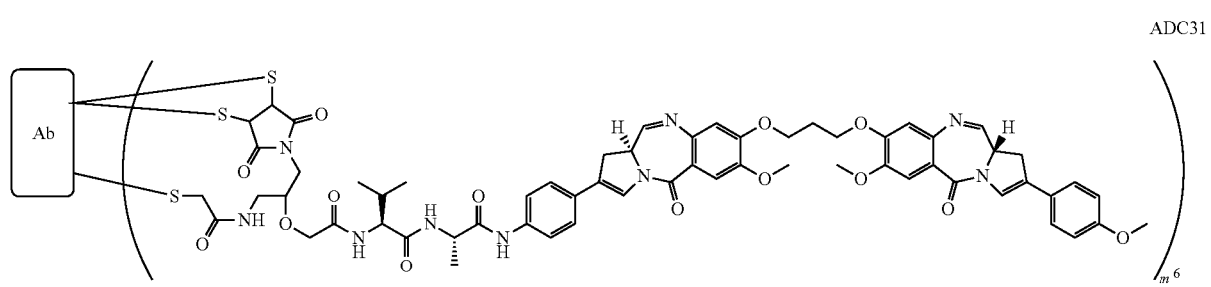
ADC32
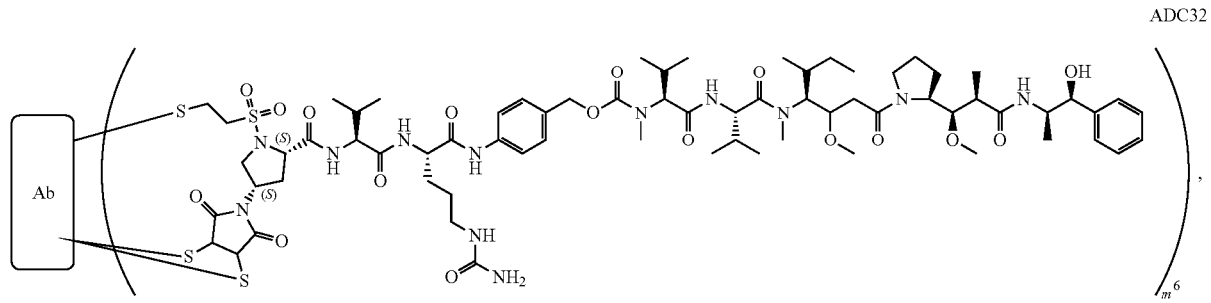

wherein:
the Ab is an antibody against cell surface receptors and tumor-related antigens;
$n^{10}$ is 0, 1, 2, 3 or 4;
$m^6$ is 0, 1 or 2.
Furthermore, the antibody-drug conjugate has the structure:
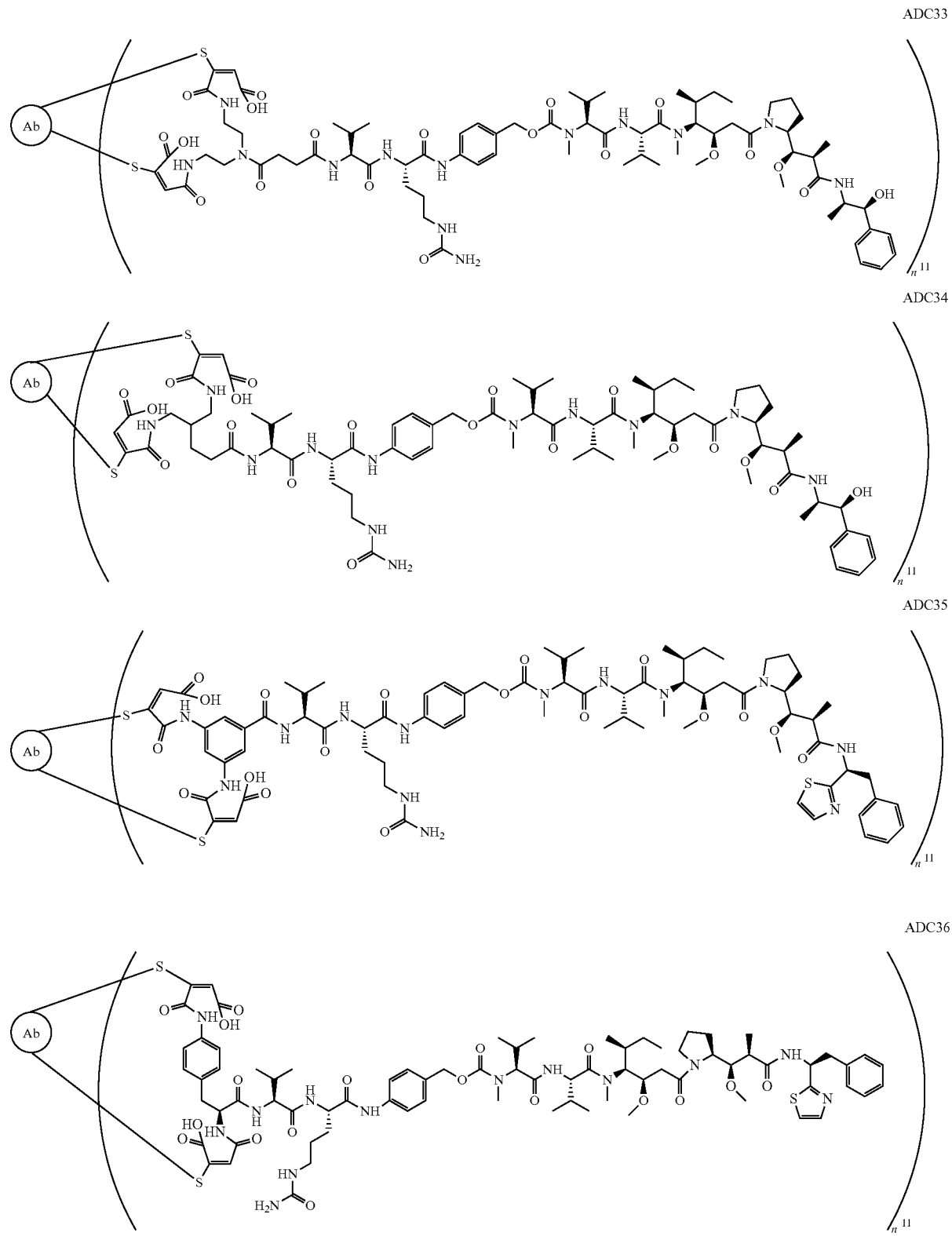

ADC37
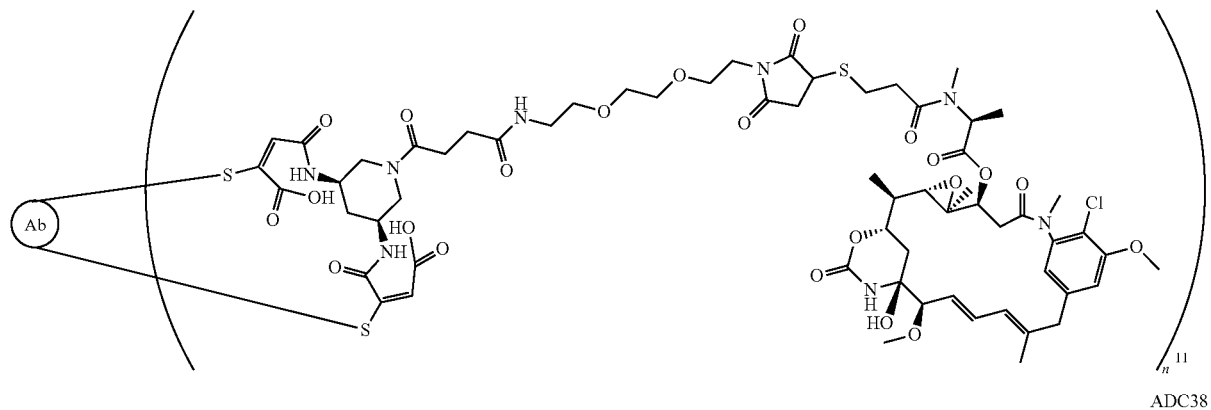
ADC38
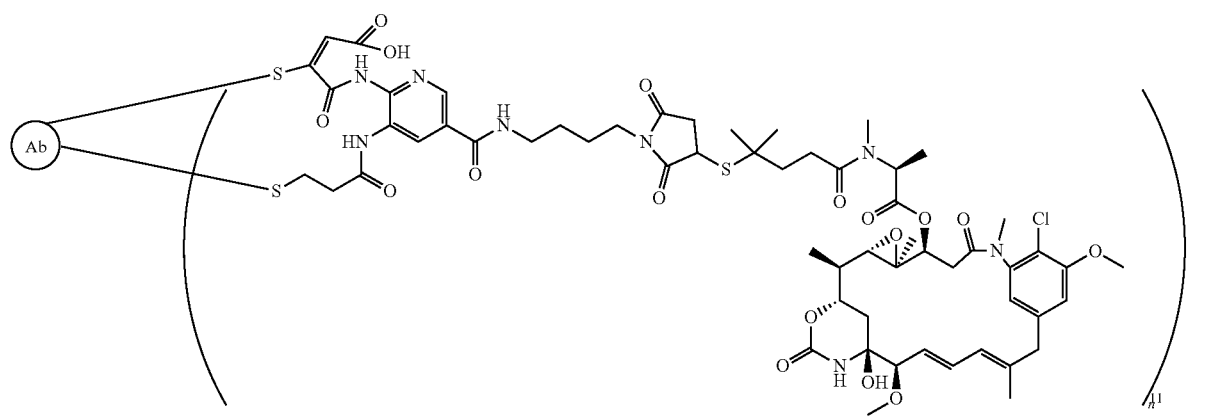
ADC39
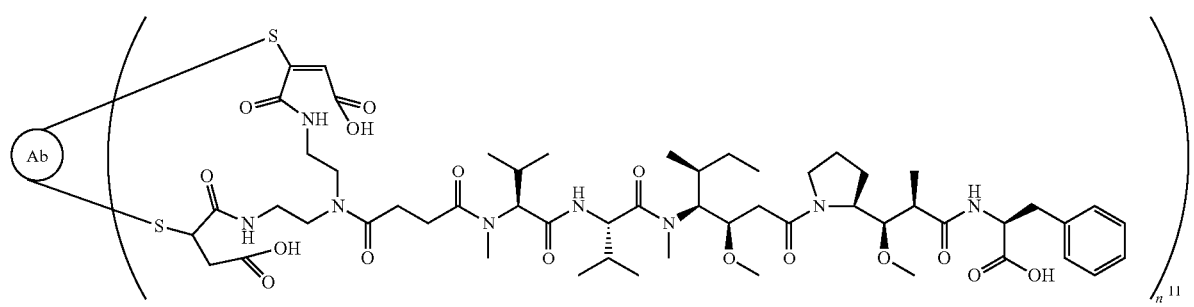
ADC40
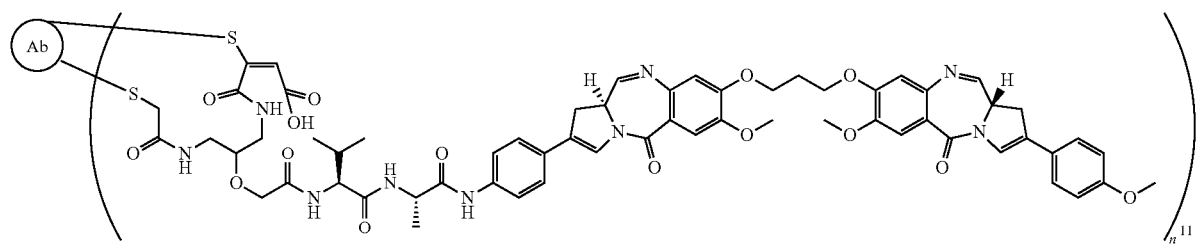

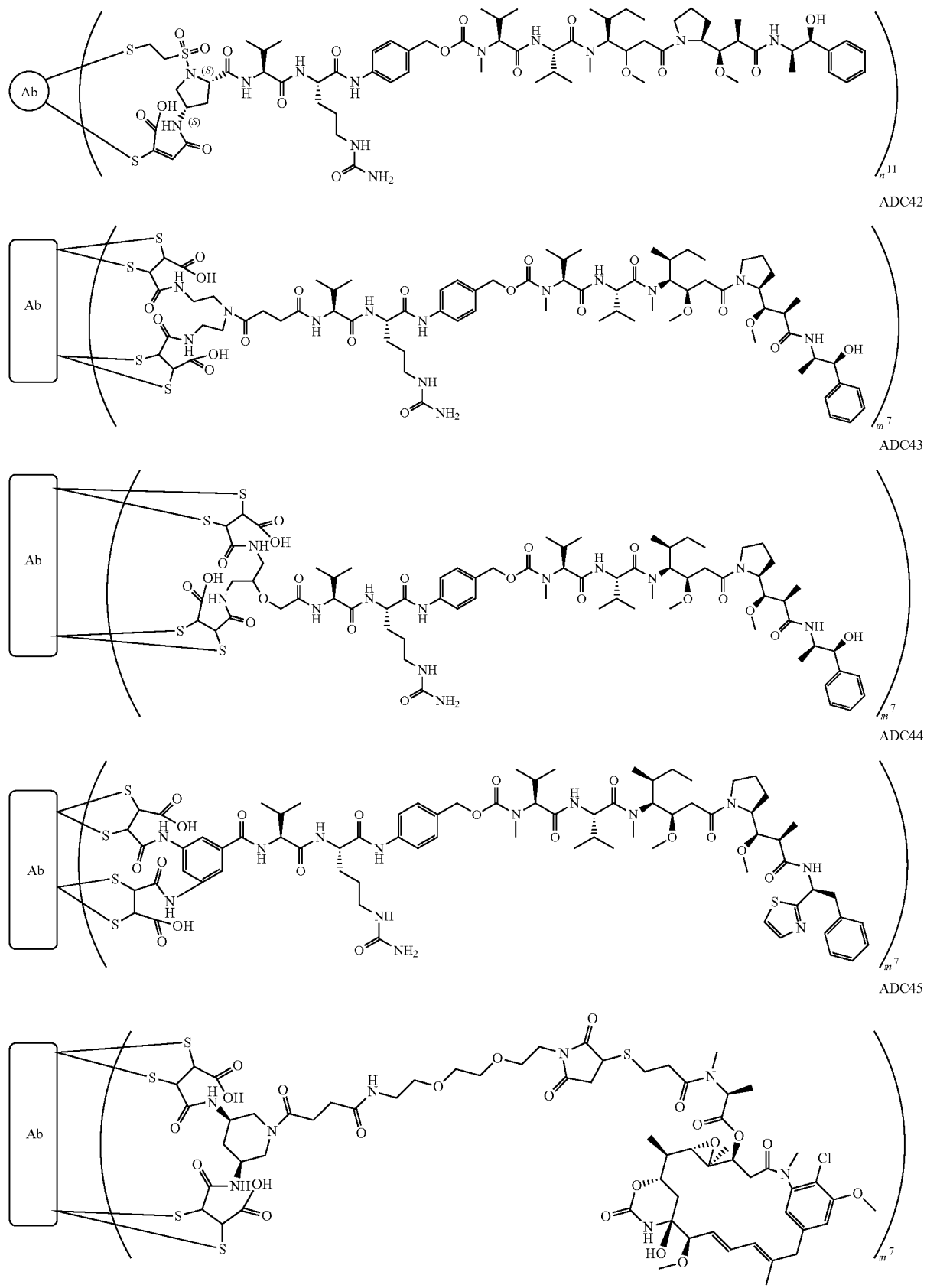

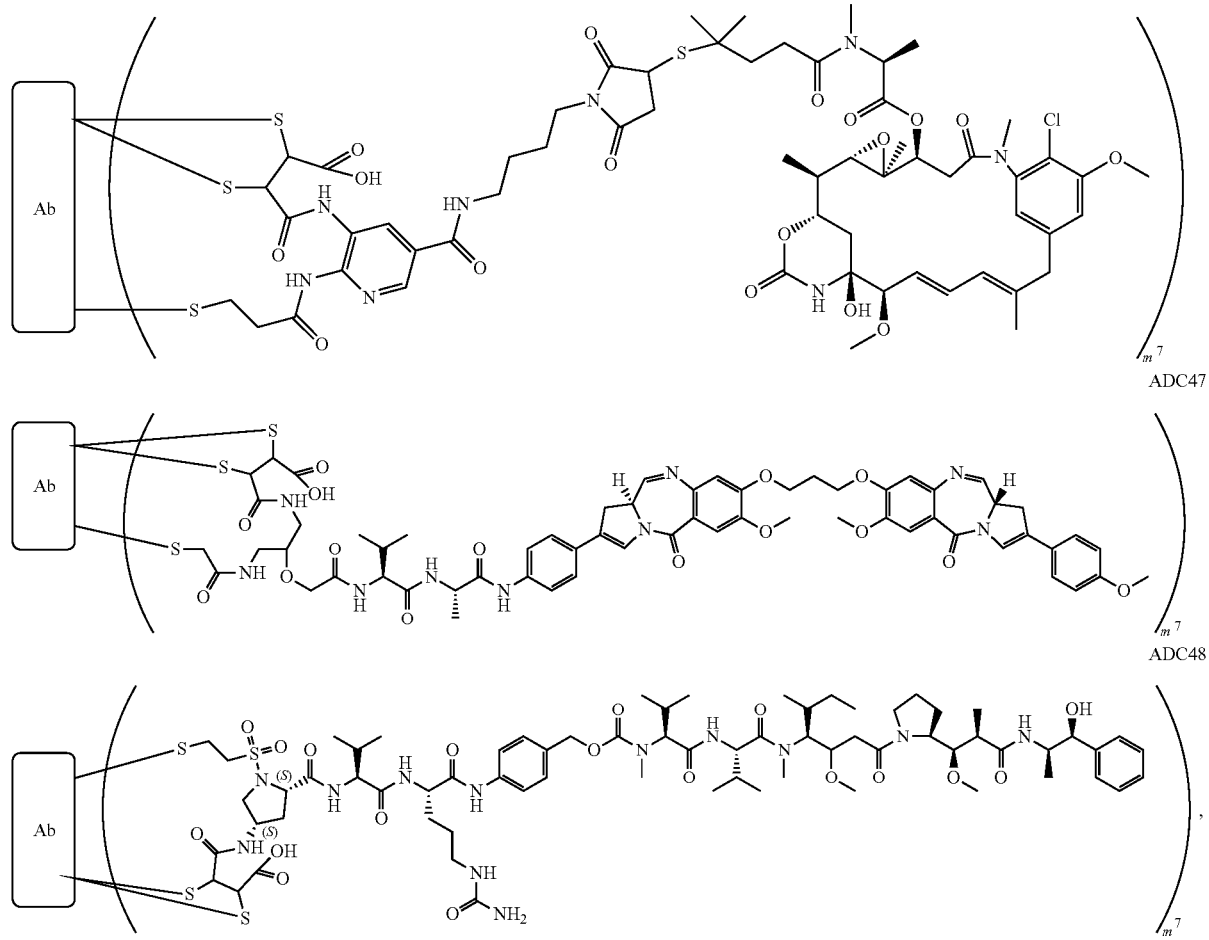

wherein:
the Ab is an antibody against cell surface receptors and tumor-related antigens;
$n^{11}$ is 0, 1, 2, 3 or 4;
$m^7$ is 0, 1 or 2.

The present invention also provides a pharmaceutical composition, which comprises any antibody-drug conjugate as described in the present invention and a pharmaceutically acceptable carrier.

The present invention also provides use of any linker as described in the present invention in the preparation of antibody-drug conjugate.

The present invention also provides use of any antibody-drug conjugate as described in the present invention, or any pharmaceutical composition as described in the present invention, in the preparation of a medicament for the treatment of cancer, autoimmune diseases, inflammatory diseases or infectious diseases.

MODE CARRYING OUT THE INVENTION

Figure 1A:
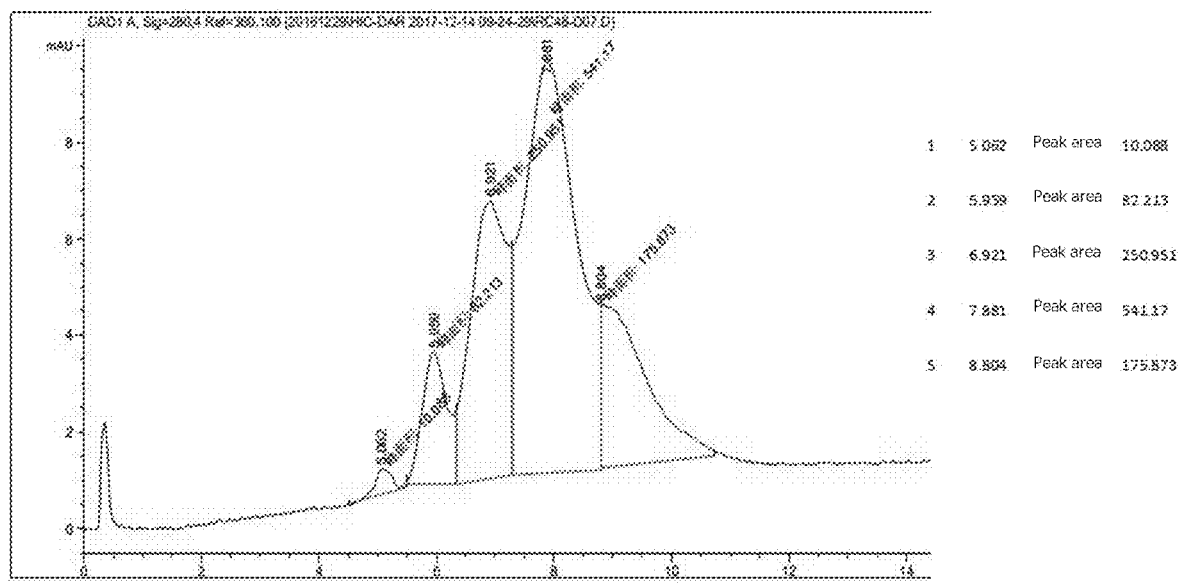
FIG. 1A shows an HIC-HPLC chromatogram of the antibody-drug conjugate Her2-A'-7-Val-Cit-PAB-MMAE (the molar ratio of drug to thiol group of antibody added during coupling is 5:1).
Figure 1B:
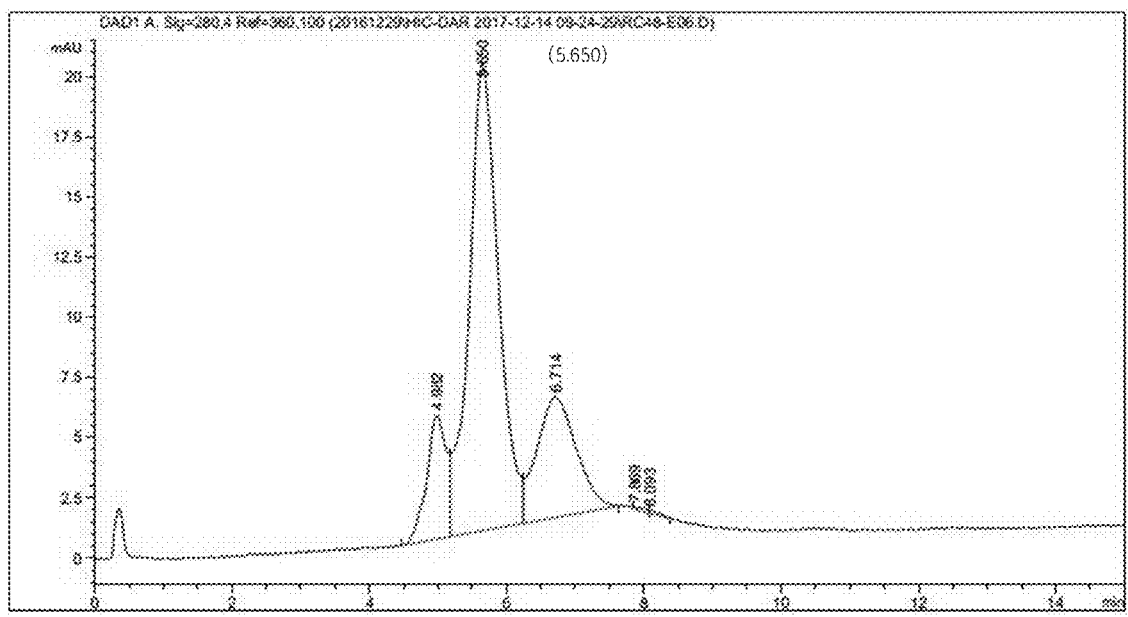
FIG. 1B shows an HIC-HPLC chromatogram of the antibody-drug conjugate Her2-A'-11-Val-Cit-PAB-MMAE (the molar ratio of drug to thiol group of antibody added during coupling is 5:1).
Figure 1C:
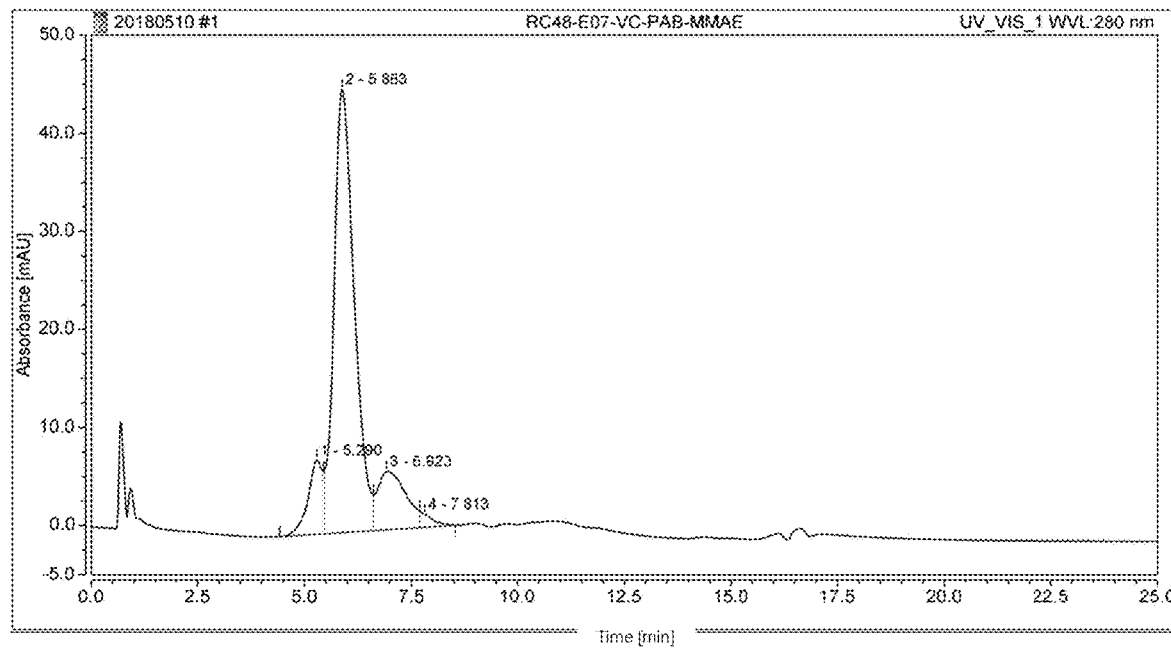
FIG. 1C shows an HIC-HPLC chromatogram of the antibody-drug conjugate Her2-A'-10-Val-Cit-PAB-MMAE (the molar ratio of drug to thiol group of antibody added during coupling is 5:1).
Figure 1D:
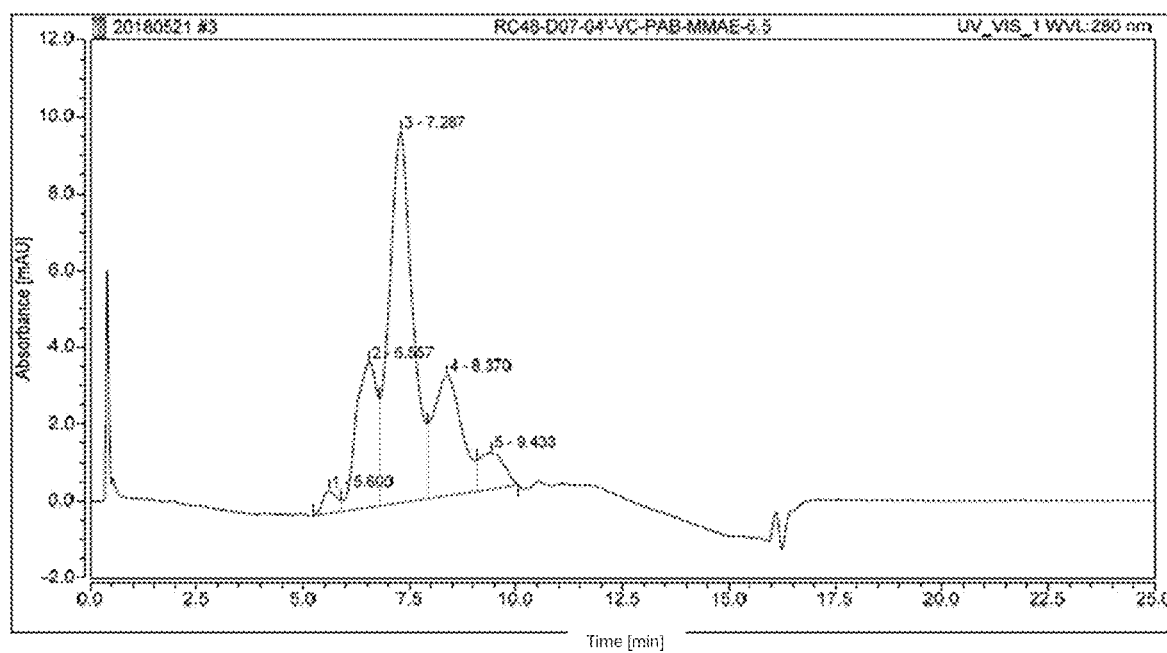
FIG. 1D shows an HIC-HPLC chromatogram of the antibody-drug conjugate Her2-575DZ-Val-Cit-PAB-MMAE (the molar ratio of drug to thiol group of antibody added during coupling is 5:1).

The embodiments of the present invention are described in detail below by way of specific examples, but in any case they cannot be construed as limiting the present invention.

Definitions

Unless otherwise defined, all scientific and technological terms used herein have the same meanings as understood by those skilled in the art.

Although the numerical ranges and parameter approximate values are shown in the broad scope of the present invention, the numerical values shown in the specific examples are recorded as accurately as possible. However, any numerical value inherently inevitably contains a certain error, which is caused by the standard deviation in measurement. In addition, all ranges disclosed herein should be understood as covering any and all sub-ranges contained therein. For example, the range of "1 to 10" recorded should be understood as covering any and all sub-ranges contained between the minimum value 1 and the maximum value 10 (including endpoints), that is, all sub-ranges starting with the minimum value 1 or greater, for example, 1 to 6.1, and all sub-ranges ending with the maximum value 10 or less, for example, 5.5 to 10. In addition, any reference referred to as "incorporated herein" should be understood as being incorporated in its entirety.

The symbol "$\xi$" used in the present invention refers to that the group containing "$\xi$" is linked here to other groups through chemical bond.

The term "antibody" in the present invention is used in the broadest sense, and covers various antibody structures, including, but not limited to, monoclonal antibody, polyclonal antibody, multispecific antibody (such as bispecific antibody), and antibody fragments. In particular, "antibody" used herein refers to a protein containing at least two heavy (H) chains and two light (L) chains interconnected by disulfide bonds. Each heavy chain includes a heavy chain variable region (abbreviated as VH) and a heavy chain constant region. The heavy chain constant region includes three domains, CH1, CH2 and CH3. Each light chain includes a light chain variable region (abbreviated as VL) and a light chain constant region. The light chain constant region includes one domain, CL. VH and VL regions can be further subdivided into multiple regions with high variability, called complementarity determining regions (CDR), interspersed with more conservative regions called framework regions (FR). Each of VH and VL consists of three CDRs and four FRs, arranged in the following order from amino terminal to carboxy terminal: FR1, CDR1, FR2, CDR2, FR3, CDR3, FR4. These variable regions of the heavy chain and light chain contain binding domains that interact with antigens. The constant region of an antibody can mediate the binding of immunoglobulins to host tissues or factors, including various cells (such as effector cells) of the immune system and the first component (Clq) of the classical complement system. Chimeric or humanized antibodies are also included in the antibodies according to the present invention.

The term "humanized antibody" refers to an antibody that contains CDR region derived from a non-human antibody, and the other moiety of the antibody molecule is derived from one (or several) human antibodies. Moreover, for retaining binding affinity, it is possible to modify some residues of the framework regions (called FR) (Jones et al., Nature, 321:522-525, 1986; Verhoeyen et al., Science, 239: 1534-1536, 1988; Riechmann et al., Nature, 332:323-327, 1988). The humanized antibody or fragments thereof according to the present invention can be prepared by techniques known to those skilled in the art (e.g., those described in the documents Singer et al., J. Immun. 150: 2844-2857, 1992; Mountain et al., Biotechnol. Genet. Eng. Rev., 10:1-142, 1992; or Bebbington et al., Bio/Technology, 10:169-175, 1992).

The term "chimeric antibody" refers to an antibody in which the variable region sequence is from one species and the constant region sequence is from another species. For example, the variable region sequence is from a mouse antibody and the constant region sequence is from a human antibody. The chimeric antibody or fragments thereof according to the present invention can be prepared by using genetic recombination technology. For example, the chimeric antibody can be produced by cloning recombinant DNA, and the recombinant DNA comprises a promoter and a sequence encoding the variable regions of a non-human, especially murine, monoclonal antibody according to the present invention, and a sequence encoding the constant regions of a human antibody. The chimeric antibody of the present invention encoded by this recombinant gene will be, for example, a mouse-human chimera. The specificity of this antibody is determined by the variable region derived from murine DNA, and its isotype is determined by the constant region derived from human DNA. As to the method of preparing a chimeric antibody, for example, please refer to the document Verhoeyn et al. (BioEssays, 8:74, 1988).

The term "monoclonal antibody" refers to a prepared products of antibody molecules with a single molecular composition. A monoclonal antibody composition shows a single binding specificity and affinity for a specific epitope.

The term "functional fragment" in the present invention means that the antibody fragment is composed of, or comprises, partial sequence of the heavy or light variable chain of the antibody from which it is derived, and the partial sequence is sufficient to retain the same binding specificity as the antibody from which it is derived and sufficient affinity, preferably at least equal to $1/100$ of the affinity of the antibody from which it is derived, and more preferably at least equal to $1/10$. This functional fragment will contain a minimum of 5 amino acids, preferably 10, 15, 25, 50 and 100 consecutive amino acids of the antibody sequence from which it is derived.

The term "DAR", also called drug to antibody ratio, in the present invention is a unique quality attribute of antibody-drug conjugate. A high DAR value may affect the safety of ADC, and its treatment window is narrow. A low DAR value may lead to a decrease in efficacy of ADC, but its safety is strong and its treatment window is wide. The best average DAR value range is 2-4.

The term "linker" in the present invention refers to a compound that can act as a "bridge" to respectively react with antibody/functional fragment of the antibody and drug, and connect the two. The "linker" involved in the present invention includes a first linker moiety and a second linker moiety. The term "first linker moiety" in the present invention includes two linking groups that are the same or different. The linking groups are capable of simultaneously covalently linked to the interchain thiol group(s) or amino group(s) of the antibody/functional fragment of the antibody, and the linking groups are any functional groups capable of covalently linked to thiol group(s) or amino group(s). The term "second linker moiety" in the present invention is used for coupling with a drug, and it is any cleavable or non-cleavable linker. The cleavable linker releases toxins depending on intracellular processes, such as intracytoplasmic reduction process, exposure to acidic conditions in lysosome or cleavage by intracellular specific protease. Non-cleavable linker can release the drug only after the protein of the ADC antibody moiety is degraded.

The term "drug" in the present invention generally refers to any compound that has the desired biological activity and has a reactive functional group to prepare the conjugate of the present invention. The desired biological activity includes diagnosis, cure, alleviation, treatment, prevention of human or other animal diseases. With the continuous discovery and development of new drugs, these new drugs should also be included in the drugs of the present invention. Specifically, the drugs include, but not limited to, cytotoxic drugs, cell differentiation factors, stem cell nutritional factors, steroid drugs, drugs for the treatment of autoimmune diseases, anti-inflammatory drugs or drugs for the treatment of infectious diseases. More specifically, the drugs include, but not limited to, tubulin inhibitors or DNA, RNA damaging agents.

In some embodiments of the present invention, the drug is selected from: maytansine compounds, V-ATPase inhibitors, pro-apoptotic agents, Be 12 inhibitors, McL1 inhibitors, HSP90 inhibitors, IAP inhibitor, mTOr inhibitors, microtubule stabilizers, microtubule destabilizers, auristatin, dolastatin, MetAP (methionine aminopeptidase), nuclear export inhibitors of protein CRM1, DPPIV inhibitors, proteasome inhibitors, inhibitors of phosphoryl transfer reaction in mitochondria, protein synthesis inhibitors, kinase inhibitors, CDK2 inhibitors, CDK9 inhibitors, kinesin inhibitors, HDAC inhibitors, DNA damaging agents, DNA alkylating agents, DNA intercalators, DNA minor groove binder, DHFR inhibitors, as well as dolastatin peptide, vitamin A precursors, folic acid, camptothecin derivatives.

In some preferred embodiments of the present invention, the drug is a cytotoxic drug (such as antimetabolites, anti-tumor antibiotics, alkaloids), immunopotentiator or radioisotope. Preferably, the drug can be selected from amanitins, anthracyclines, baccatins, camptothecins, cemadotins, colchicines, colcimids, combretastatins, cryptophycins, discodermolides, docetaxel, doxorubicin, echinomycins, eleutherobins, epothilones, estramustines, lexitropsins, maytansines, methotrexate, netropsins, puromycins, rhizoxins, taxanes, tubulysins, or vinca alkaloids. More preferably, the "drug" is selected from MMAD (Monomethyl auristatin D) and its derivatives, MMAE (Monomethyl auristatin E) and its derivatives, MMAF (Monomethyl auristatin F) and its derivatives, maytansine derivatives DM1 (Mertansine derivative M1), maytansine derivatives DM4 (Mertansine derivative M4), Duocarmycine and its derivatives, Calicheamicin and its derivatives, PBDA (Pyrrolobenzodiazepines), Doxorubicin, Vinca Alkaloids, Metrotrexate, Vinblastine, Daunorubicin and its derivatives, tubulysins and its derivatives, camptothecin derivatives SN-38, topoisomerase I inhibitors (i.e., Dxd).

In some specific embodiments, the "drug" may be the following substances and their derivatives:

Maytansine:

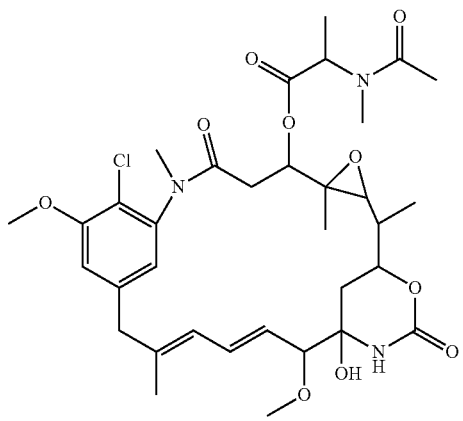

Maytansine

Maytansinoid derivatives:
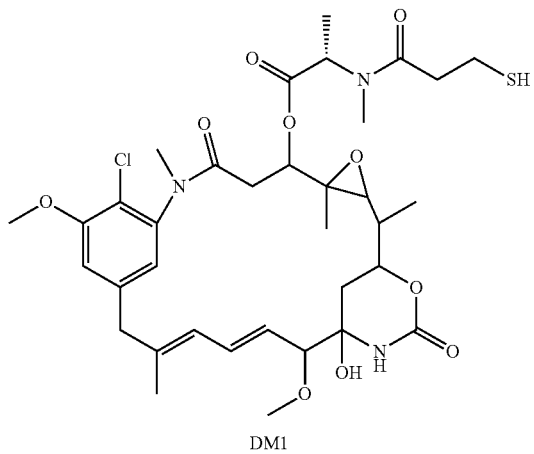
DM1
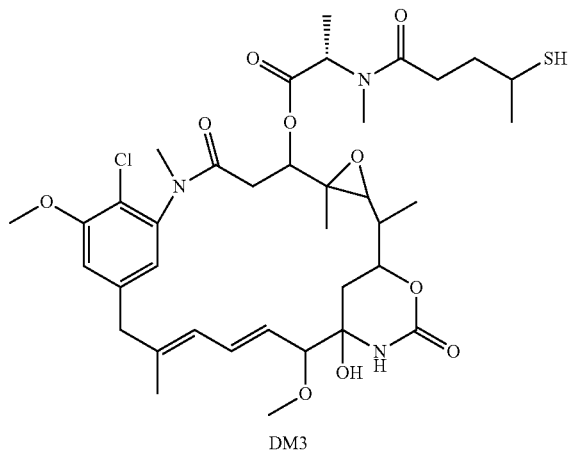
DM3
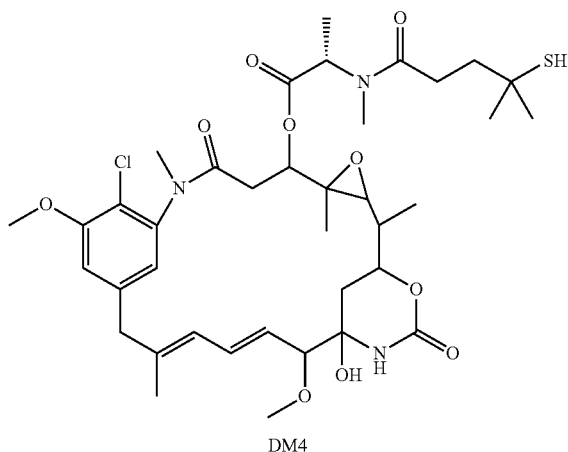
DM4
Ansamitocin derivatives:
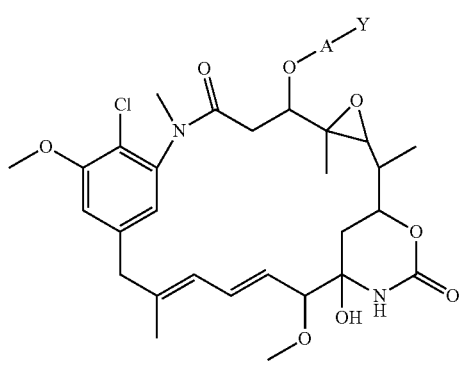
A is C=O, (C=O)NR′, and (C=O)O
Y is a substituent group
Ansamitocin derivatives
Alaninyl maytansinol:
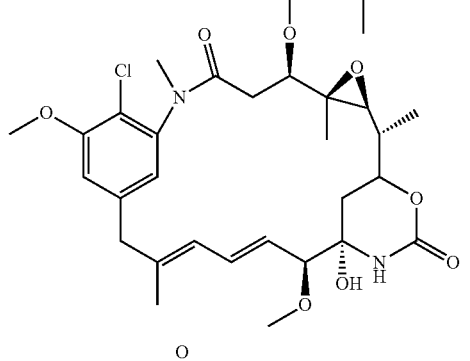
L is 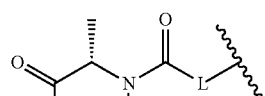
Alaninyl maytansinol -continued
MMAE:
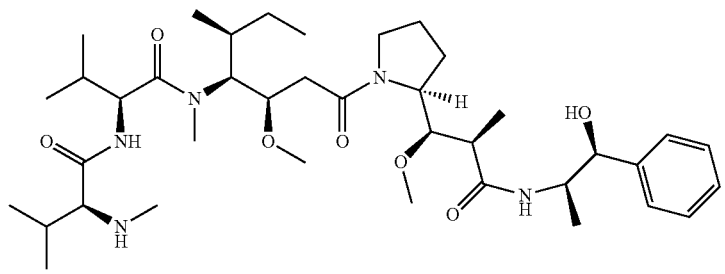
MMAE
MMAD:
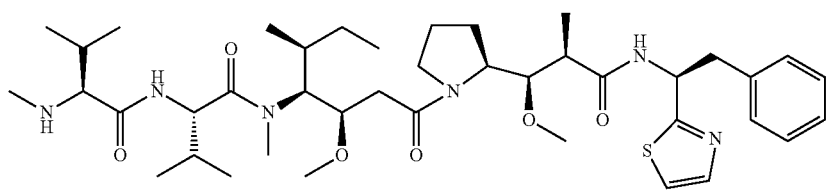
MMAD
MMAF:
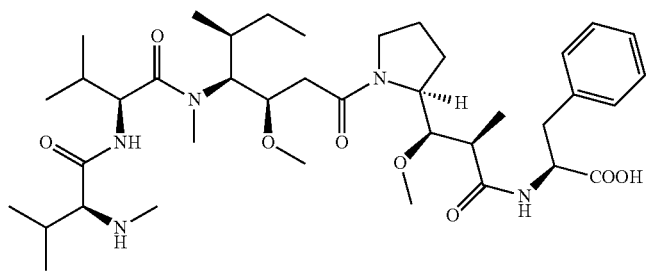
MMAF
Tubulysin D:
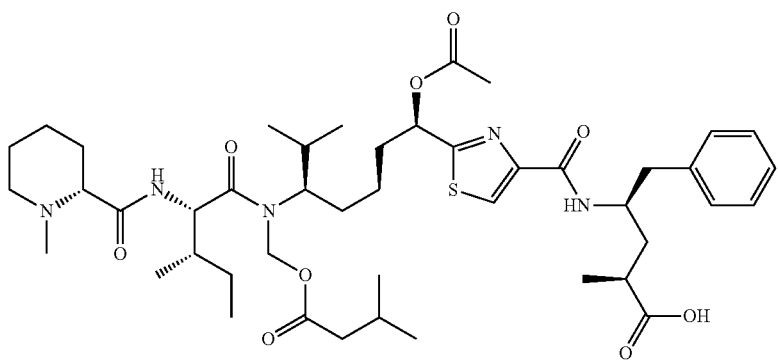
Tubulysin D -continued
Calicheamicin:
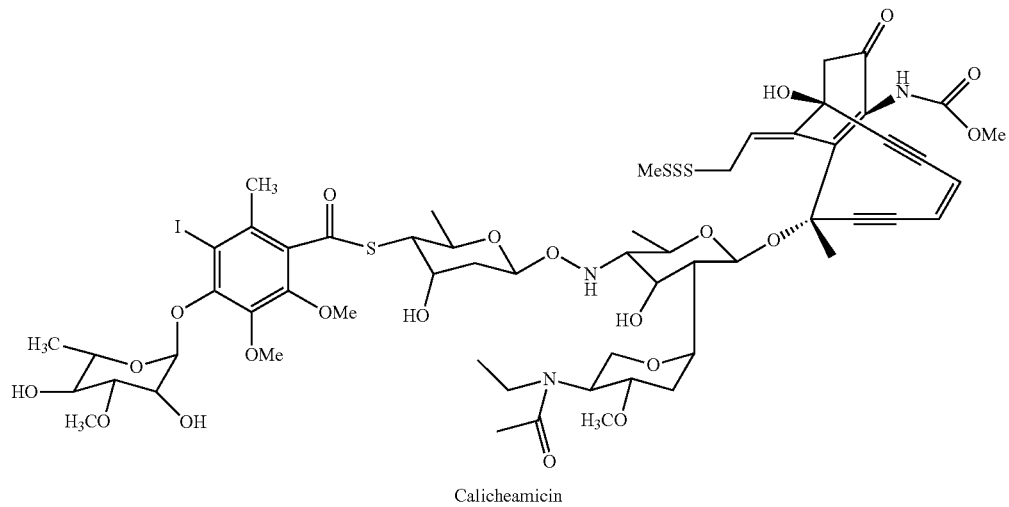
Calicheamicin
Doxorubicin:
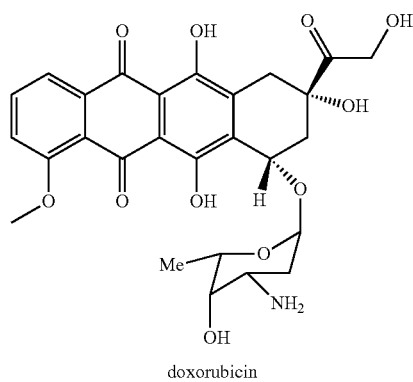
doxorubicin
Pyrrolobenzodiazepine derivatives:
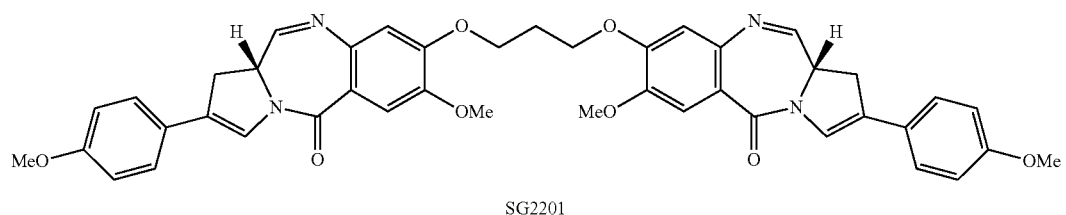
SG2201
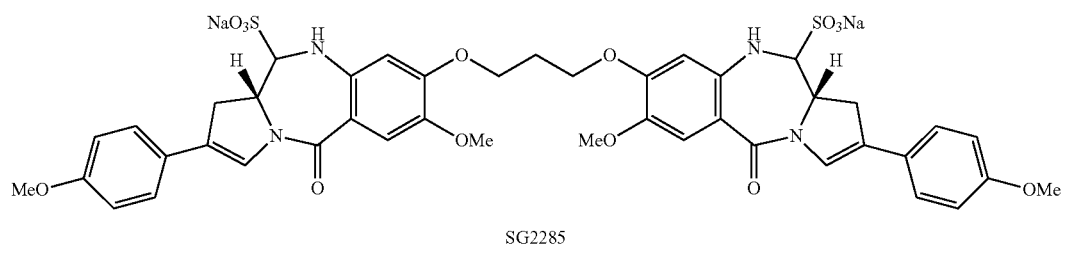
SG2285

-continued

Folic acid:

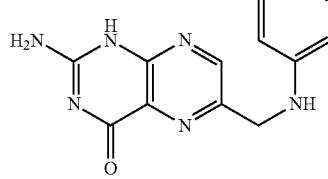

Vitamin A precursor:

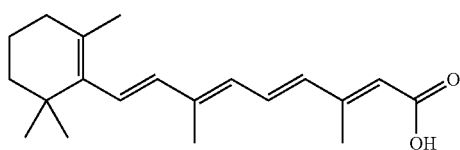

Topoisomerase I inhibitor (i.e., Dxd):

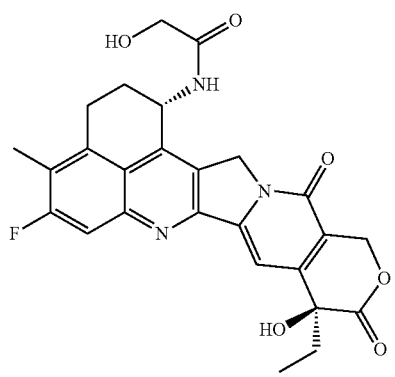

The term "antibody-drug conjugate" in the present invention refers to a compound obtained by linking an antibody/a functional fragment of the antibody, a linker (a first linker moiety, a second linker moiety), and a drug moiety together through chemical reaction. Although the antibody-drug conjugate involved in the present invention is still a mixture, compared with the conjugate obtained in the traditional way, its DAR distribution range is very narrow, and the best antibody-drug conjugate has an average DAR value range of 2-4. Regarding the preparation of the antibody-drug conjugate according to the present invention, when the conjugate (A-L-D) of the first linker moiety (A) and the second linker moiety-drug conjugate (L-D) is coupled with an antibody (such as claudin18.2 antibody provided in the example), it can hydrolyze under easy hydrolysis conditions, and the hydrolysis site is in the maleimide moiety of the first linker. Taking Ab-A'-7-VC-PAB-MMAE (and in the case where one antibody is coupled with 4 drugs) as an example, when the Ab-A'-7-VC-PAB-MMAE conjugate undergoes 4 hydrolysis, the structure diagram is:

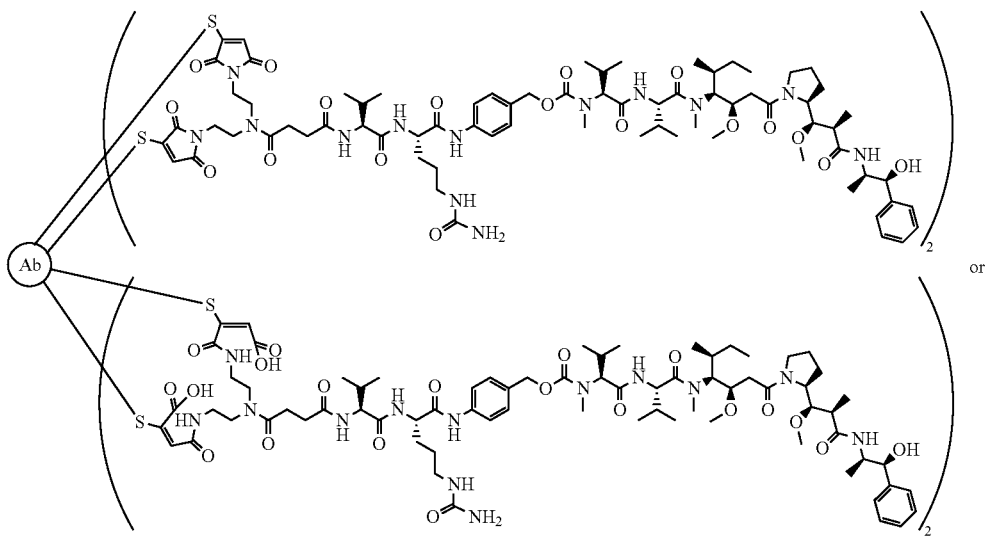

or

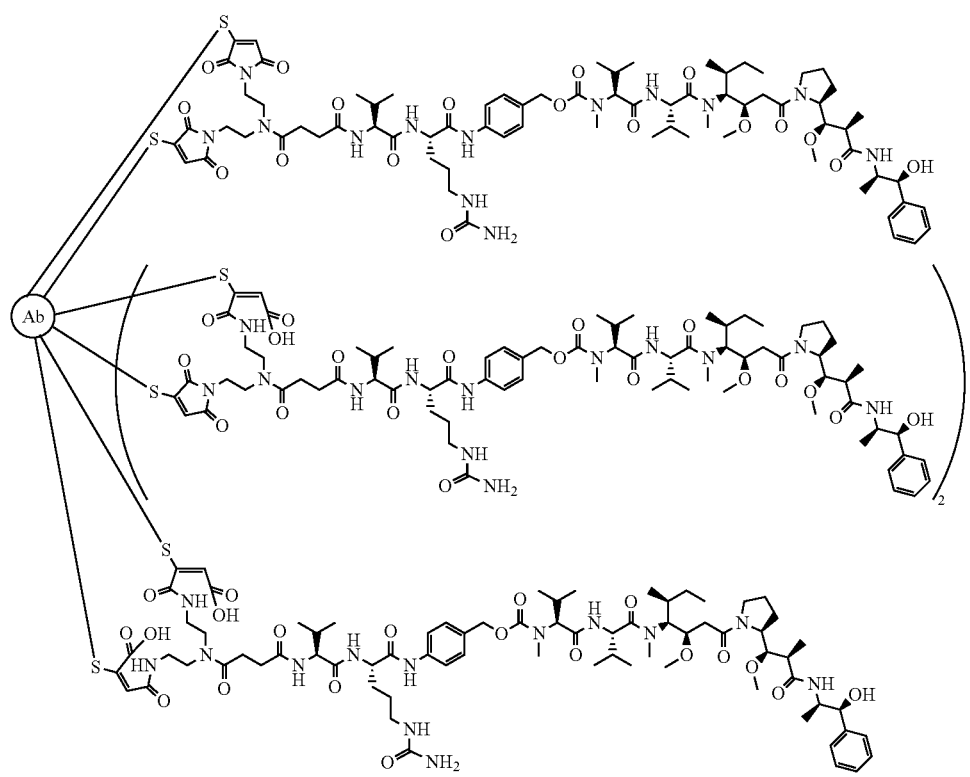
When the Ab-A'-7-VC-PAB-MMAE conjugate undergoes 7 hydrolysis, the structure diagram is:
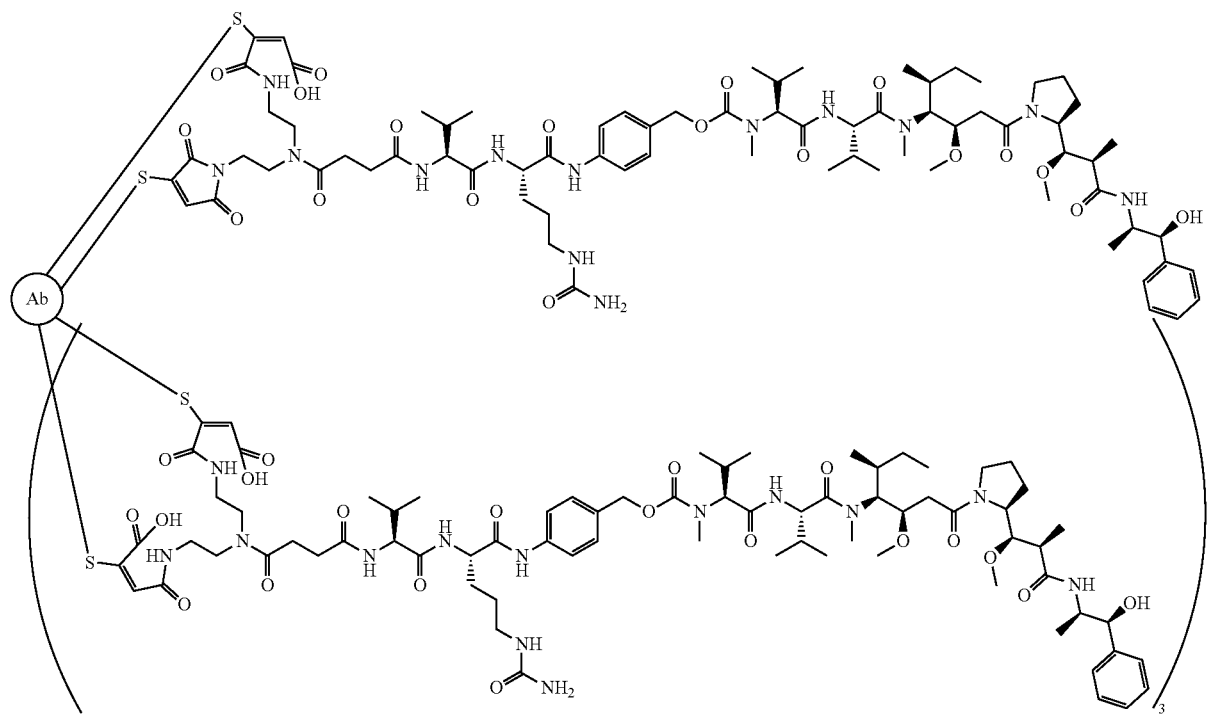

When the Ab-A'-7-VC-PAB-MMAE conjugate undergoes 8 hydrolysis, the structure diagram is:

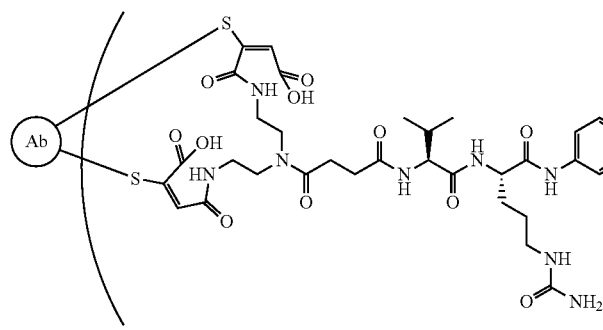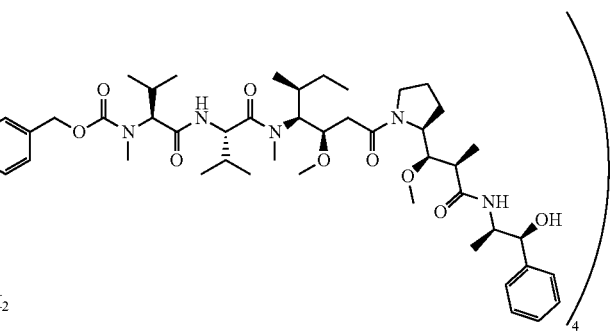

The term "pharmaceutical composition" in the present invention refers to a combination of at least one drug and optionally a pharmaceutically acceptable carrier or excipient that are combined to achieve a specific purpose. In some embodiments, the pharmaceutical composition includes a combination of ingredients that are separated in time and/or space, as long as they can work together to achieve the purpose of the present invention. For example, the ingredients contained in the pharmaceutical composition can be administered to a subject as a whole, or separately. When the ingredients contained in the pharmaceutical composition are separately administered to a subject, the ingredients can be simultaneously or sequentially administered to the subject. Preferably, the pharmaceutically acceptable carrier is water, buffered aqueous solution, isotonic salt solution such as PBS (phosphate buffer), glucose, mannitol, dextroglucose, lactose, starch, magnesium stearate, cellulose, magnesium carbonate, 0.3% glycerol, hyaluronic acid, ethanol or polyalkylene glycol such as polypropylene glycol, triglycerides and the like. The type of the pharmaceutically acceptable carrier used particularly depends on whether the composition according to the present invention is formulated for oral, nasal, intradermal, subcutaneous, intramuscular or intravenous administration. The composition according to the present invention can contain wetting agents, emulsifiers or buffer substances as additives.

The pharmaceutical composition, vaccine or pharmaceutical preparation according to the present invention can be administered by any suitable route, such as oral, nasal, intradermal, subcutaneous, intramuscular or intravenous administration.

The term "alkyl" in the present invention refers to a linear or branched saturated hydrocarbon (i.e., free of double bonds or triple bonds). Alkyl group can have 1 to 9 carbon atoms (when appearing in the present invention, the numerical range of "1 to 9" refers to any integer in this range, for example, "1 to 9 carbon atoms" means that the alkyl group can contain 1 carbon atom, 2 carbon atoms, 3 carbon atoms, . . . , up to 9 carbon atoms. At the same time, the definition of alkyl also includes alkyl groups with no specified chain length). The alkyl group can be a medium-sized alkyl group containing 1 to 9 carbon atoms. A typical alkyl group includes, but not limited to: methyl, ethyl, propyl, isopropyl, butyl, isobutyl, tert-butyl, pentyl, hexy and the like.

The term "alkenyl" in the present invention refers to a linear or branched hydrocarbon containing one or multiple double bonds. Alkenyl group can have 2 to 9 carbon atoms, and also includes alkenyl groups with no specified chain length. The alkenyl group can be a medium-sized alkenyl group containing 2 to 9 carbon atoms. The alkenyl group can also be a small-sized alkenyl group containing 2 to 4 carbon atoms. The alkenyl group can be designed as "C2-4 alkenyl" or similar designs. For example, "C2-4 alkenyl" means that there are 2-4 carbon atoms in the alkenyl chain, that is, the alkenyl chain can be selected from: ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, buta-1,2-dien-4-yl. Typical alkenyl includes, but not limited to: ethenyl, propenyl, butenyl, pentenyl, hexenyl and the like.

The term "alkynyl" in the present invention refers to a linear or branched hydrocarbon containing one or multiple triple bonds. Alkynyl group can have 2 to 9 carbon atoms, and also includes alkynyl groups with no specified chain length. The alkynyl group can be a medium-sized alkynyl group containing 2 to 9 carbon atoms. The alkynyl group can also be a lower alkynyl group containing 2 to 4 carbon atoms. The alkynyl group can be designed as "C2-4 alkynyl" or similar designs. For example, "C2-4 alkynyl" means that there are 2-4 carbon atoms in the alkynyl chain, that is, the alkynyl chain can be selected from: ethynyl, propyn-1-yl, propyn-2-yl, butyn-1-yl, butyn-2-yl, butyn-3-yl and 2-butynyl. Typical alkynyl includes, but not limited to: ethynyl, propynyl, butynyl, pentynyl, hexynyl and the like.

The term "aryl" in the present invention refers to a ring or ring system with conjugated π-electron system, and includes carbocyclic aryl (such as phenyl) and heterocyclic aryl (such as pyridine). The term includes groups with a single ring or multiple fused rings (i.e., rings that share a pair of adjacent atoms), and the whole ring system is aromatic.

The term "heteroaryl" in the present invention refers to an aromatic ring or ring system (i.e., two or multiple fused rings that share two adjacent atoms) containing one or multiple heteroatoms. That is, in addition to carbon, the ring skeleton includes, but not limited to, nitrogen, oxygen, sulfur and other elements. When heteroaryl is a ring system, each ring in the system is aromatic. Heteroaryl can have 5-18 ring members (i.e., the number of atoms constituting the ring skeleton, including the number of carbon atoms and heteroatoms). The current definition also includes heteroaryl groups with no specified ring size. Examples of heteroaryl include, but not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridyl, pyridazinyl, pyrimidinyl, pyrazinyl, triazinyl, quinolinyl, isoquinolinyl, benzimidazolyl, benzoxazolyl, benzothiazolyl, indolyl, isoindolyl, benzothienyl.

The term "cycloalkyl" in the present invention refers to a fully saturated carbocyclic or ring system. Examples include, but not limited to, cyclopropyl, cyclobutyl, cyclopentyl, cyclohexyl.

The term "(heterocyclyl) alkyl" in the present invention refers to heterocyclyl as a substituent connected to other groups through alkylene. Examples include, but not limited to, imidazolinyl methyl and indolinyl ethyl. The term "heterocyclyl" refers to a non-aromatic ring or ring system containing at least one heteroatom in its skeleton. Heterocyclyl can be connected in the form of fused rings, bridged rings or spiro rings. At least one ring in the heterocyclyl ring system is non-aromatic, and it can have any degree of saturation. The heteroatom can be located on the non-aromatic or aromatic ring of the ring system. The heterocyclyl can have 3 to 20 ring atoms (i.e., the number of atoms constituting the ring skeleton, including the number of carbon atoms and heteroatoms). The current definition also includes heterocyclyl groups with no specified range of ring numbers. The heterocyclyl group can be a medium-sized heterocyclyl group containing 3 to 10 ring atoms. The heterocyclyl group can also be a small-sized heterocyclyl group containing 3 to 6 ring atoms. Examples of heterocyclyl include, but not limited to: azepinyl, acridinyl, carbazolyl, cinnolinyl, dioxolanyl, imidazolinyl, imidazolidinyl, morpholinyl, oxiranyl, oxepanyl, thietanyl, piperidinyl, piperazinyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathianyl, 1,4-oxathianyl, 2H-1,3-dioxolanyl, 1,3-dithiolanyl, 1,3-dithiolanyl, isoxazolinyl, isoxazolidinyl, oxazolinyl, oxazolidinyl, oxazolidinone, oxazolidinone, thiazolidinyl, 1,3-isoindolinyl, tetrahydrofuranyl, tetrahydropyranyl, oxathiolyl, indolinyl, tetrahydrothiopyranyl, tetrahydro-1,4-thiazinyl, tetrahydrothienyl, thiomorpholinyl, dihydrobenzofuranyl, benzimidazolidinyl and tetrahydroquinolinyl.

EXAMPLES

General Procedure A: General Synthesis Method of Bromomaleimide Linker

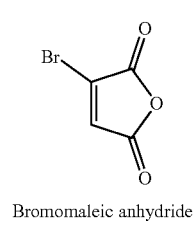

Bromomaleic anhydride

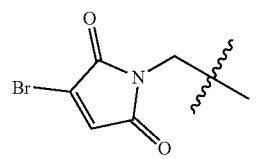

Amines and their salts or Boc protected derivative (1 eq) and anhydrous sodium acetate (2.5 eq) were dissolved in acetic acid (1 mmol/2 mL), and heated up to 50-100° C., followed by rapid addition of bromomaleic anhydride (2.5 eq), and reacted at 50-100° C. overnight. The reaction solution was cooled to 45° C., concentrated under reduced pressure, and ethyl acetate was added to the residue, followed by washing, drying and concentrating to get a crude product. The crude product was purified by normal phase column chromatography or reversed phase preparative liquid chromatography to obtain the target product.

General Procedure B: General Synthesis Method of Thiophenol Maleimide Linker

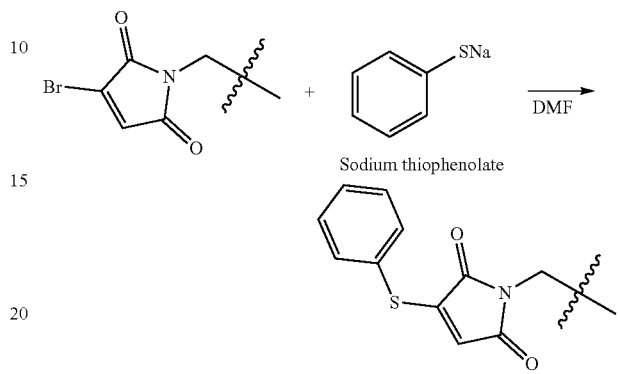

Bromomaleimide linker (1.0 eq) was dissolved in anhydrous DMF (1 mmol/5 mL), to which was added pyridine (3.0 eq), followed by stirring at room temperature for 5-10 min. Sodium thiophenolate (2.1 eq) was dissolved in anhydrous DMF (1 mmol/1 mL), and added dropwise to the reaction solution. Thereafter, stirring was continued at room temperature for 0.5-5 h. After the reaction was completed, 5 times volume of distilled water was added, to precipitate out solids, followed by filtering, washing, drying and concentrating to get a crude product. The crude product was purified by normal phase column chromatography or reversed phase preparative liquid chromatography to obtain the target product.

Example 1 Synthesis of A'-1

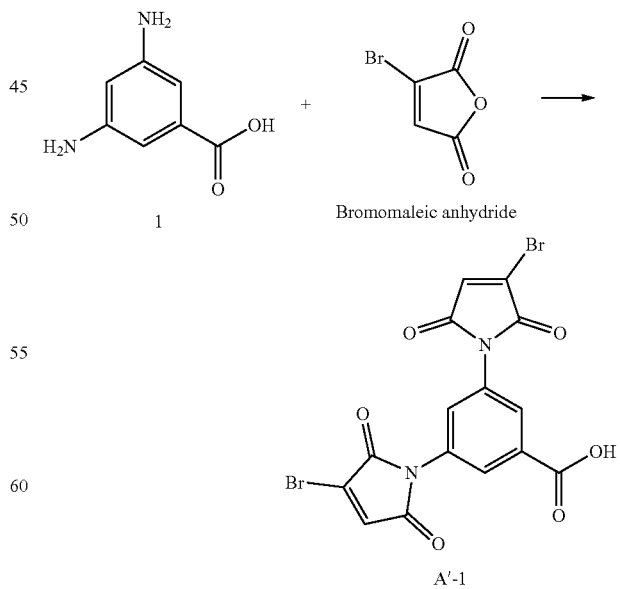

According to General procedure A, 300 mg of compound 1 (i.e., 3, 5-diaminobenzoic acid) was added, while other materials being added in molar ratios. The reaction was carried out at 70° covernight. The reaction solution was purified by preparative liquid chromatography, to obtain the target compound A'-1. LC-MS (ESI+) 468.9 [M+H]$^+$.

Example 2 Synthesis of A'-4

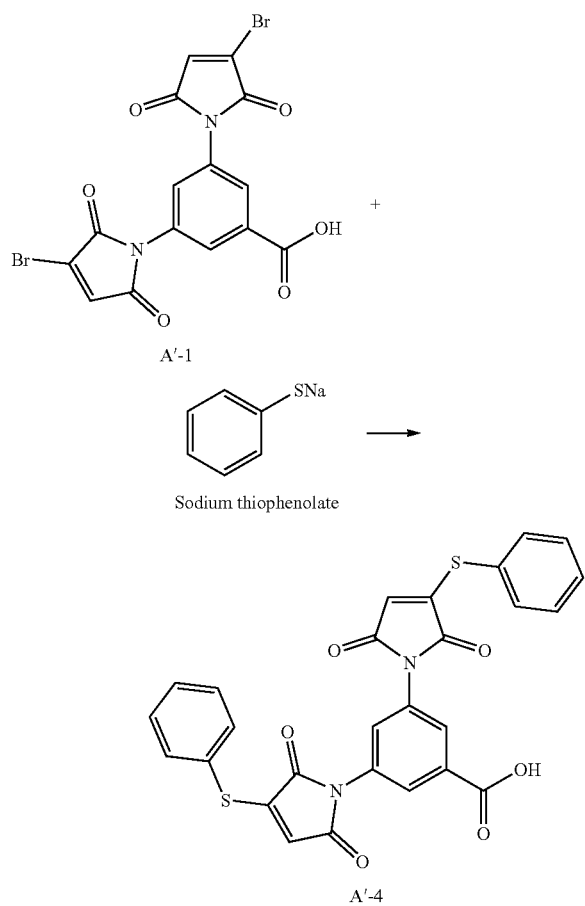

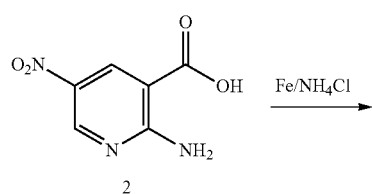

According to General procedure B, 100 mg of compound A'-1 was added, while other materials being added in molar ratios. The reaction solution was purified by preparative liquid chromatography, to obtain the target compound A'-4. LC-MS (ESI+) 529.0 [M+H]$^+$.

Example 3 Synthesis of A'-2

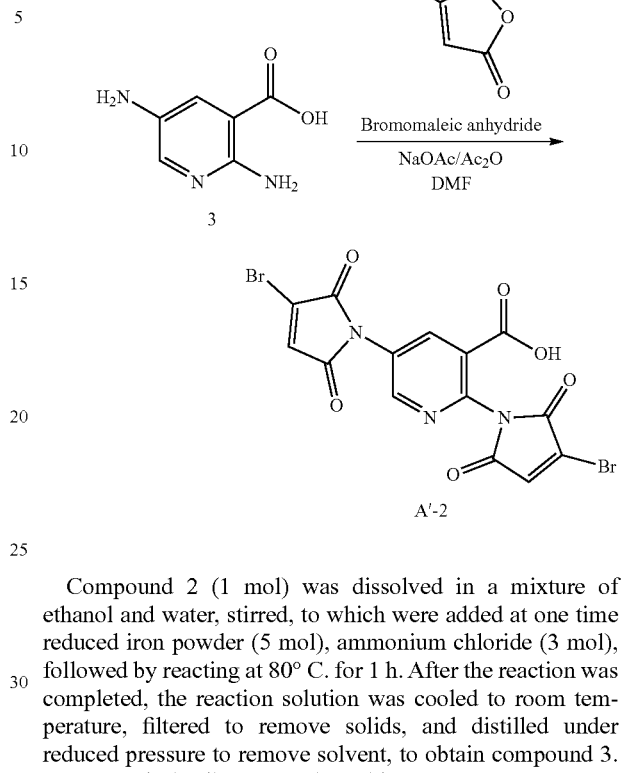

Compound 2 (1 mol) was dissolved in a mixture of ethanol and water, stirred, to which were added at one time reduced iron powder (5 mol), ammonium chloride (3 mol), followed by reacting at 80° C. for 1 h. After the reaction was completed, the reaction solution was cooled to room temperature, filtered to remove solids, and distilled under reduced pressure to remove solvent, to obtain compound 3. LC-MS m/z (ES$^+$), 154.05 (M+H)$^+$.

According to General procedure A, compound 3 (1 mol) was added, while other materials being added in molar ratios. The reaction was carried out at 80° C. overnight. The reaction solution was purified by preparative liquid chromatography, to obtain the target compound A'-2. LC-MS m/z (ES$^+$), 471.85 (M+H)$^+$.

Example 4 Synthesis of A'-7

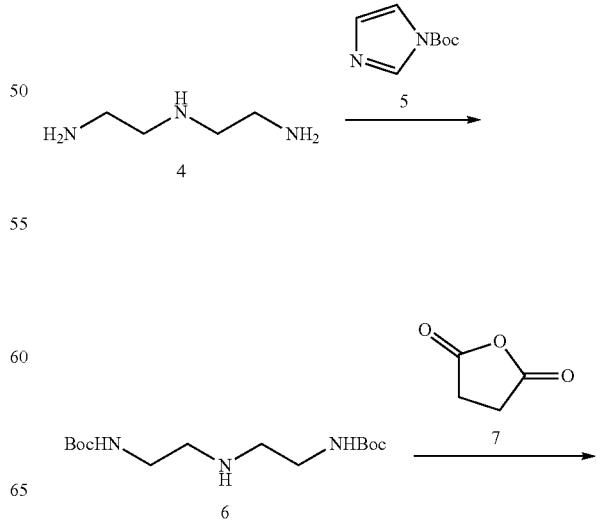

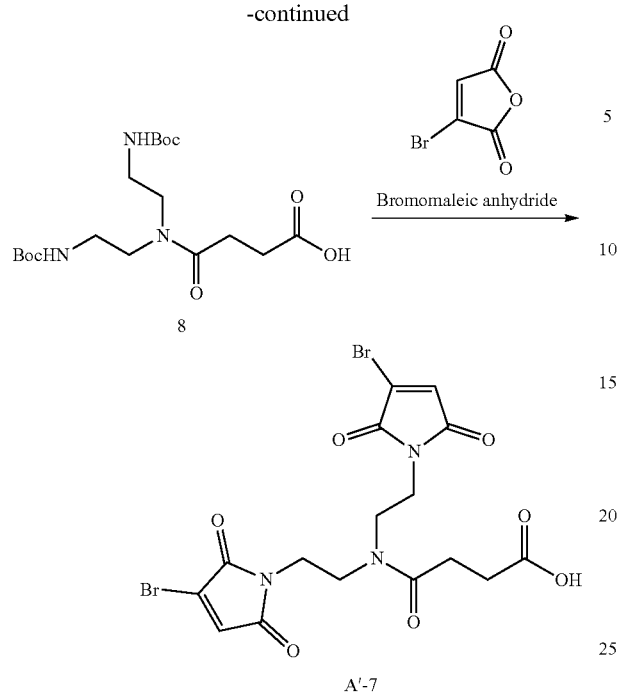

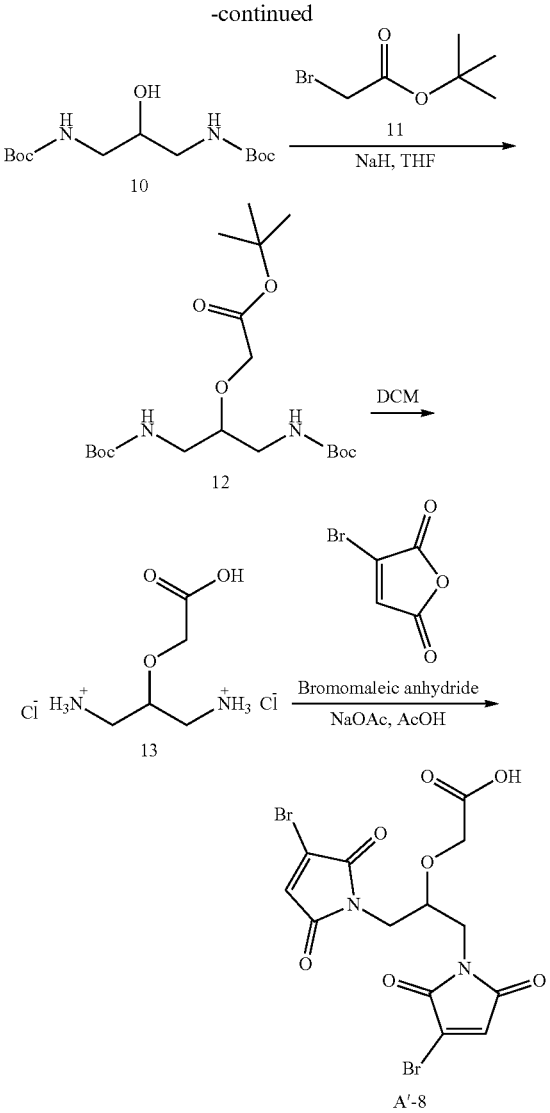

Compound 5 (Boc-imidazole, 2.37 g, 14.1 mmol) was dissolved in 30 mL of toluene, to which was added compound 4 (diethylenetriamine, 0.66 g, 6.41 mmol) at room temperature, followed by stirring with heating at 60° C. for 6 h. After the reaction was completed, the reaction solution was distilled under reduced pressure to obtain an oily crude product. The crude product was dissolved in 40 mL of dichloromethane, washed with water (40 mL×3), dried, filtered and concentrated to obtain 1.84 g of compound 6, in a yield of 95%. LC-MS (ESI+) 304.2 [M+H]+.

Compound 6 (3.3 g, 10.89 mmol) was dissolved in 30 mL of anhydrous toluene, to which was added compound 7 (succinic anhydride, 1.3 g, 13 mmol), followed by stirring with heating at 60° C. overnight. After the reaction was completed, the reaction solution was distilled under reduced pressure to remove toluene, the residue was dissolved in 20 mL of dichloromethane, washed with water (20 mL×2), washed with saturated NaCl (20 mL×1), dried, filtered and distilled under reduced pressure to obtain 3.5 g of compound 8, in a yield of 80%. LC-MS (ESI+) 404.3 [M+H]+.

According to General procedure A, 100 mg of compound 8 was added, while other materials being added in molar ratios. The reaction was carried out at 70° C. overnight. The reaction solution was purified by preparative liquid chromatography, to obtain 25.8 mg of the target compound A'-7, in a yield of 20%. LC-MS (ESI+) 519.9 [M+H]+.

Example 5 Synthesis of A'-8

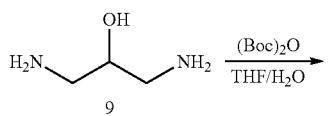

Compound 9 (1,3-diaminopropanol, 5.0 g, 55.47 mmol) was dissolved with 50 mL of THF and 20 mL of water with stirring. A solution of Boc$_2$O (25.4 g, 116.5 mmol, 2.1 eq) in 30 mL of THF was added dropwise at room temperature. Thereafter, the reaction solution was stirred at room temperature overnight. After the reaction was completed, the reaction solution was concentrated under reduced pressure. The residue, to which was added 30 mL of petroleum ether, was stirred at room temperature for 20 min, to precipitate out a white solid, which was filtered and dried to obtain 14.7 g of white compound 10, in a yield of 91%. LC-MS (ESI+) 291.2 [M+H]+.

Compound 10 (14.7 g, 50.64 mmol) was dissolved with 100 mL of anhydrous THF with stirring, followed by cooling in ice bath. Then, NaH (4.8 g, 202.55 mmol, 4 eq) was added in batches, followed by stirring for 10 min. A solution of compound 11 (tert-butyl bromoacetate, 24.7 g, 126.6 mmol, 2.5 eq) in 50 mL of THF was added dropwise. Thereafter, the reaction solution was heated up to 40° C., and stirred overnight. After the reaction was completed, the reaction solution was cooled to room temperature, diluted with 250 mL of ethyl acetate, to which was added slowly an ice-water mixture until no large amount of bubbles were formed, and then liquid separation was performed. The aqueous phase was extracted with ethyl acetate, and the organic phases were combined, washed, dried and concentrated. The residue, to which was added 50 mL of petroleum ether, was stirred at room temperature for 20 min, to precipitate out a white solid, which was filtered and dried to obtain 12.1 g of white compound 12, in a yield of 60%. LC-MS (ESI+) 404.1 [M+H]+.

Compound 12 (12.1 g, 30.0 mmol) was dissolved with 120 mL of anhydrous DCM with stirring, to which was then added a solution (4 M, 45 mL, 180 mmol) of hydrogen chloride in 1,4-dioxane, followed by stirring at room temperature overnight. After the reaction was completed, the reaction solution was concentrated under reduced pressure. The residue was dispersed by ultrasound with 30 mL of methyl tert-butyl ether, centrifuged with the removal of supernatant, and then dispersed with 30 mL of petroleum ether, centrifuged with the removal of supernatant. The solid was distilled under reduced pressure to remove the solvent, to obtain 7.7 g of white compound 13, in a yield of 100%. LC-MS (ESI+) 148.1 [M+H]+.

According to General procedure A, 1.2 g of compound 13 was added, while other materials being added in molar ratios. The reaction was carried out at 85° C. for 5 h. The reaction solution was purified by preparative liquid chromatography, to obtain 890 mg of the target compound A'-8, in a yield of 35%. LC-MS (ESI+) 464.9 [M+H]+.

Example 6 Synthesis of A'-9

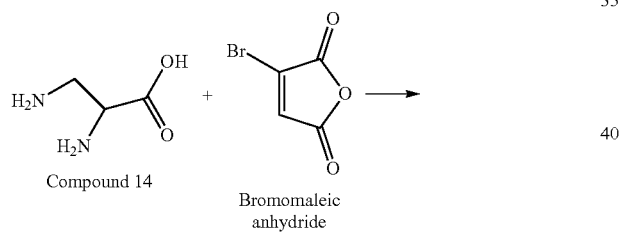

Compound 14

Bromomaleic anhydride

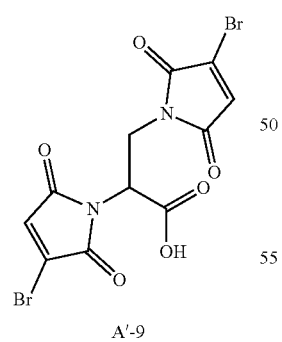

A'-9

According to General procedure A, 500 mg of compound 14 (2, 3-diaminopropionic acid) was added, while other materials being added in molar ratios. The reaction was carried out at 70° C. overnight. The reaction solution was purified by normal phase column chromatography, to obtain 240 mg of the target compound A'-9, in a yield of 23%. LC-MS (ESI$^+$) 420.9 [M+H]$^+$.

Example 7 Synthesis of A'-10

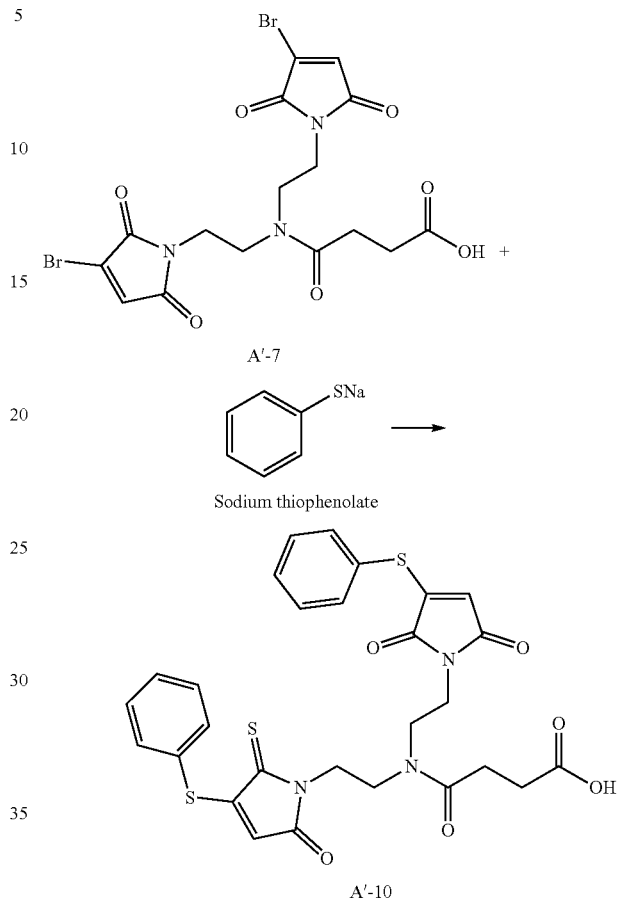

According to General procedure B, 104 mg of compound A'-7 was added, while other materials being added in molar ratios. The reaction was carried out at room temperature for 2.5 h. The reaction solution was purified by preparative liquid chromatography, to obtain 27.7 mg of the target compound A'-10, in a yield of 24%. LC-MS (ESI$^+$) 596.1 [M+H]$^+$.

Example 8 Synthesis of A'-11

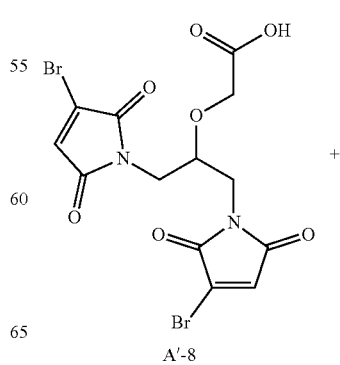

A'-8

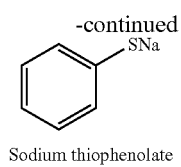

Sodium thiophenolate

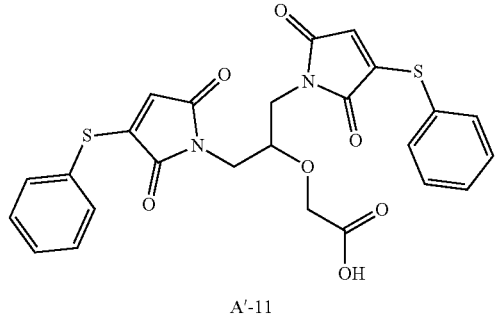

A'-11

According to General procedure B, 600 mg of compound A'-8 was added, while other materials being added in molar ratios. The reaction was carried out at room temperature for 2.5 h. The reaction solution was purified by preparative liquid chromatography, to obtain 203 mg of the target compound A'-11, in a yield of 30%. LC-MS (ESI$^+$) 525.1 [M+H]$^+$.

Example 9 Synthesis of A'-12

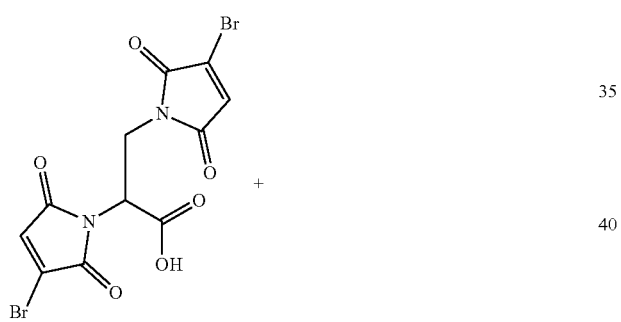

A'-12

According to General procedure B, 120 mg of compound A'-9 was added, while other materials being added in molar ratios. The reaction was carried out at room temperature for 0.7 h. The reaction solution was purified by preparative liquid chromatography, to obtain 30 mg of the target compound A'-12, in a yield of 22%. LC-MS (ESI$^+$) 481.0 [M+H]$^+$.

Example 10 Synthesis of A'-13

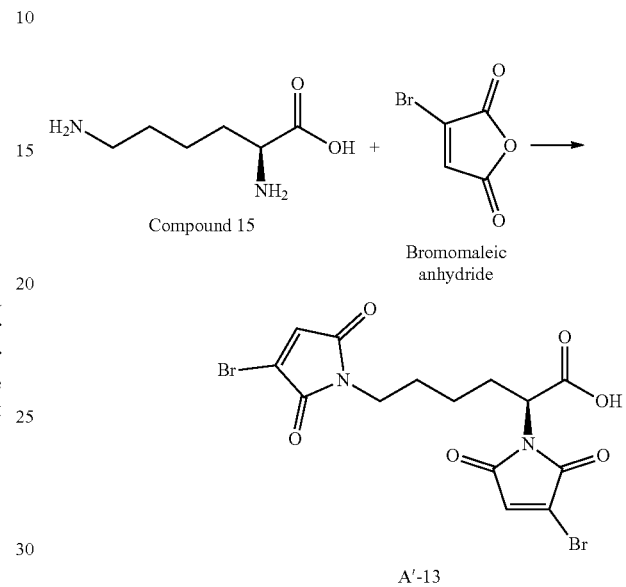

A'-13

According to General procedure A, 500 mg of compound 15 (L-lysine) was added, while other materials being added in molar ratios. The reaction was carried out at 70° C. overnight. The reaction solution was purified by normal phase column chromatography, to obtain 410 mg of the target compound A'-13, in a yield of 26%. LC-MS (ESI$^+$) 462.9 [M+H]$^+$.

Example 11 Synthesis of A'-14

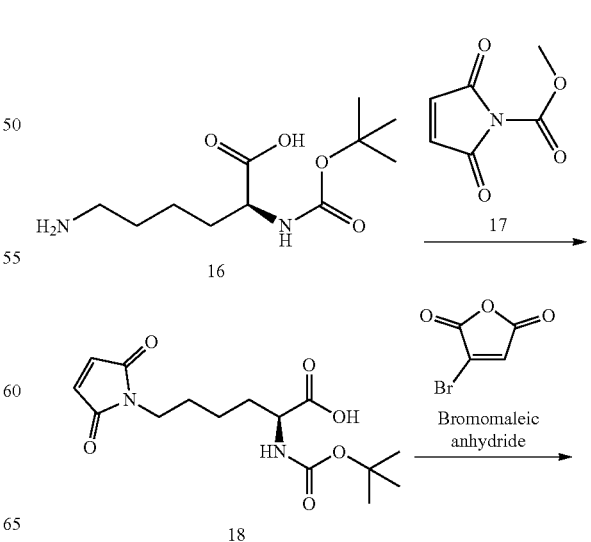

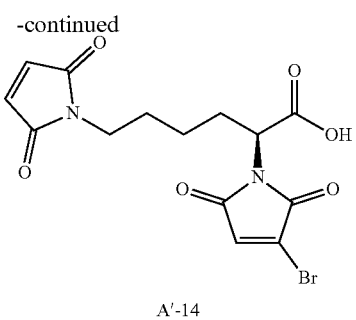

A'-14

Compound 16 (500 mg, 2.03 mmol) was dissolved with the addition of 1 mL of THF and 1 mL of saturated NaHCO₃ aqueous solution with stirring, followed by stirring in ice bath for 5 min. Then, compound 17 (724.4 mg, 4.67 mmol) was added slowly in batches, followed by stirring in ice bath for 40 min, and then stirring at room temperature for 2.5 h. After the reaction was completed, the reaction solution was subjected to rotary evaporation to remove THE, diluted with 1 mL of methanol, and separated by preparative liquid chromatography to obtain 245 mg of compound 18, in a yield of 37%. LC-MS (ESI$^+$) 327.1 [M+H]$^+$.

According to General procedure A, 245 mg of compound 18 was added, while other materials being added in molar ratios. The reaction was carried out at 70° C. overnight. The reaction solution was purified by normal phase column chromatography, to obtain 67 mg of the target compound A'-14, in a yield of 23%. LC-MS (ESI$^+$) 462.9 [M+H]$^+$.

Example 12 Synthesis of A'-15

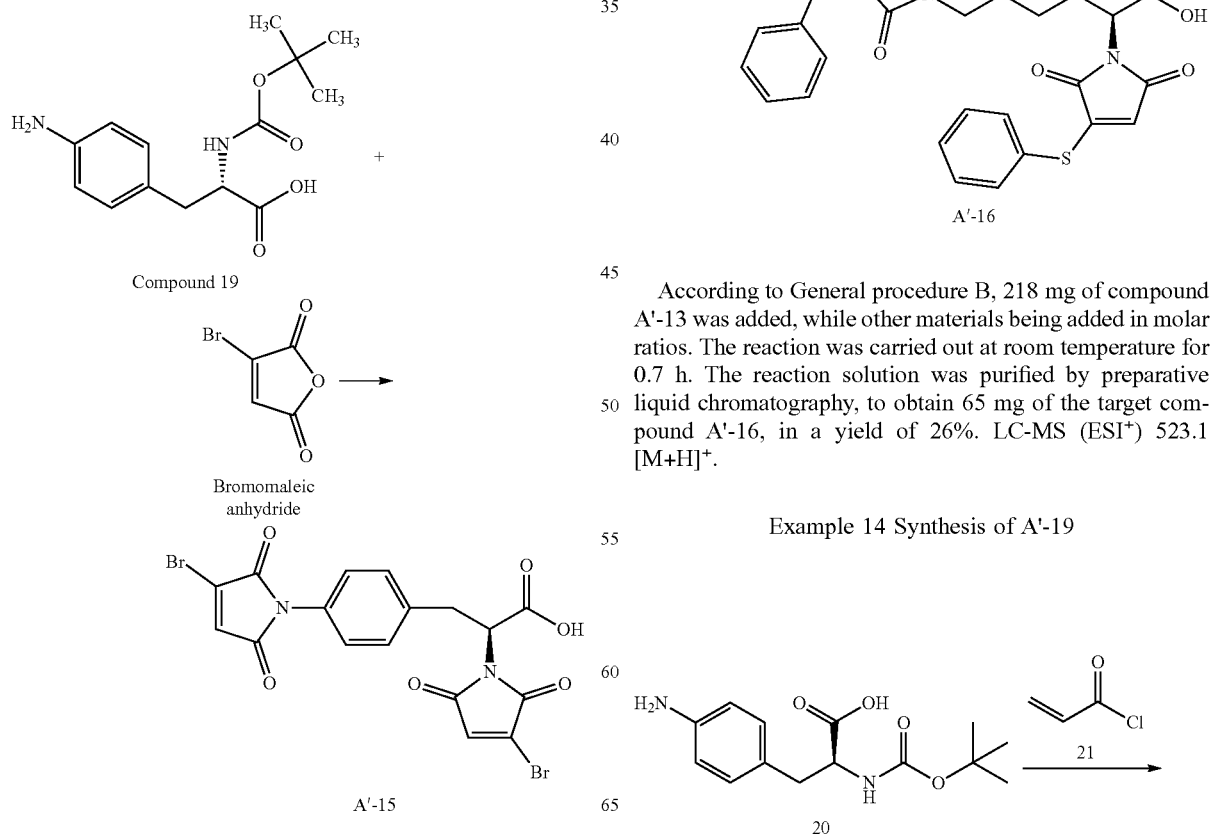

Compound 19

Bromomaleic anhydride

A'-15

According to General procedure A, 56.1 mg of compound 19 (Boc-4-amino-L-phenylalanine) was added, while other materials being added in molar ratios. The reaction was carried out at 70° C. overnight. The reaction solution was purified by normal phase column chromatography, to obtain 17.9 mg of the target compound A'-15, in a yield of 18%. LC-MS (ESI$^+$) 496.9 [M+H]$^+$.

Example 13 Synthesis of A'-16

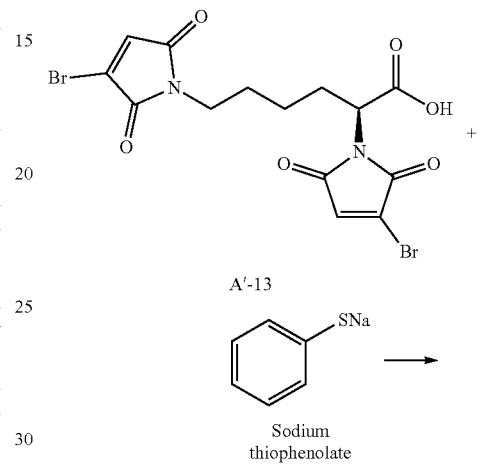

A'-13

Sodium thiophenolate

A'-16

According to General procedure B, 218 mg of compound A'-13 was added, while other materials being added in molar ratios. The reaction was carried out at room temperature for 0.7 h. The reaction solution was purified by preparative liquid chromatography, to obtain 65 mg of the target compound A'-16, in a yield of 26%. LC-MS (ESI$^+$) 523.1 [M+H]$^+$.

Example 14 Synthesis of A'-19

20

-continued

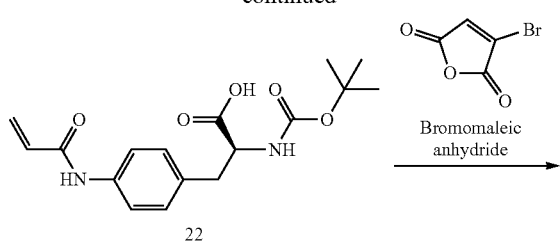

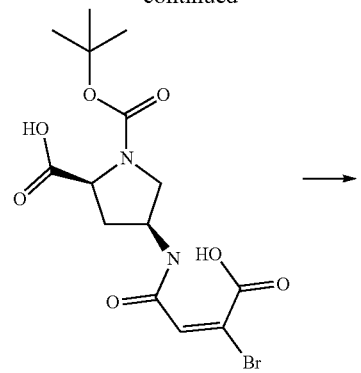

Compound 20 (140 mg, 0.5 mmol) was dissolved with 3 mL of dichloromethane, to which was added triethylamine (210 µL, 1.5 mmol), followed by stirring in ice bath. Compound 21 (62.5 µL, 0.75 mmol) was dissolved in 2 mL of DCM, and added dropwise to the reaction solution, followed by stirring in ice bath for 0.5 h, and stirring at room temperature for 2 h. After the reaction was completed, the reaction solution was concentrated. The residue was dissolved with acetonitrile, and separated by preparative liquid chromatography to obtain 93.5 mg of compound 22, in a yield of 56.1%. LC-MS (ESI⁺) 335.2 [M+H]⁺.

According to General procedure A, 33.4 mg of compound 22 was added, while other materials being added in molar ratios. The reaction was carried out at 70° C. overnight. The reaction solution was purified by normal phase column chromatography, to obtain 7.5 mg of the target compound A'-19, in a yield of 19.1%. LC-MS (ESI⁺) 393.0 [M+H]⁺.

Example 15 Synthesis of A'-20

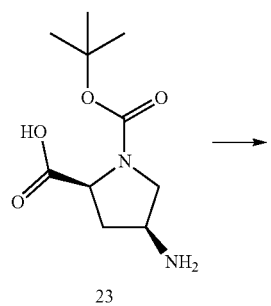

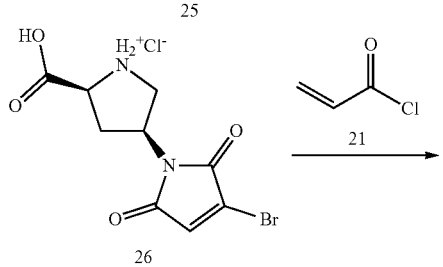

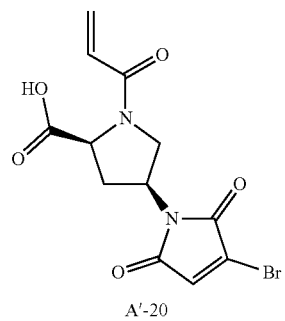

Compound 23 (230 mg, 1 mmol) was dissolved in 3 mL of THF, to which was added bromomaleic anhydride (354 mg, 2 mmol), followed by stirring at room temperature for 3 h. After the reaction was completed, the reaction solution was subjected to rotary evaporation to remove THE, to obtain a crude product of compound 24. Compound 24 was dissolved with 3 mL of acetic anhydride, to which was added sodium acetate (41 mg, 0.5 mmol), followed by stirring at 70° C. for 8 h. After the reaction was completed, the reaction solution was subjected to rotary evaporation to remove the solvent. The residue was dissolved with 4 mL of acetonitrile/water (1:1), and purified by preparative liquid chromatography to obtain 70 mg of compound 25, in a yield of 18%. LC-MS (ESI⁺) 389.0 [M+H]⁺.

To compound 25 (99.2 mg, 0.32 mmol) 2 mL of a solution (4M, 8 mmol) of hydrogen chloride in 1,4-dioxane was added, followed by stirring in ice bath for 2 h. After the reaction was completed, the reaction solution was subjected to rotary evaporation to remove the solvent. The residue was washed with diethyl ether (5 mL×3), and dried to obtain 64.1 mg of compound 26, in a yield of 95.3%. LC-MS (ESI$^+$) 289.0 [M+H]$^+$.

Compound 26 (21 mg, 0.1 mmol) was dissolved with 1 mL of dichloromethane, to which was added triethylamine (42 μL, 0.3 mmol), followed by stirring in ice bath. Compound 21 (12.5 μL, 0.15 mmol) was dissolved in 1 mL of DCM, and added dropwise to the reaction solution, followed by stirring in ice bath for 0.5 h, and stirring at room temperature for 2 h. After the reaction was completed, the reaction solution was concentrated. The residue was dissolved with acetonitrile, and separated by preparative liquid chromatography to obtain 18.2 mg of A'-20, in a yield of 69.1%. LC-MS (ESI$^+$) 343.0 [M+H]$^+$.

Example 16 Synthesis of A'-26

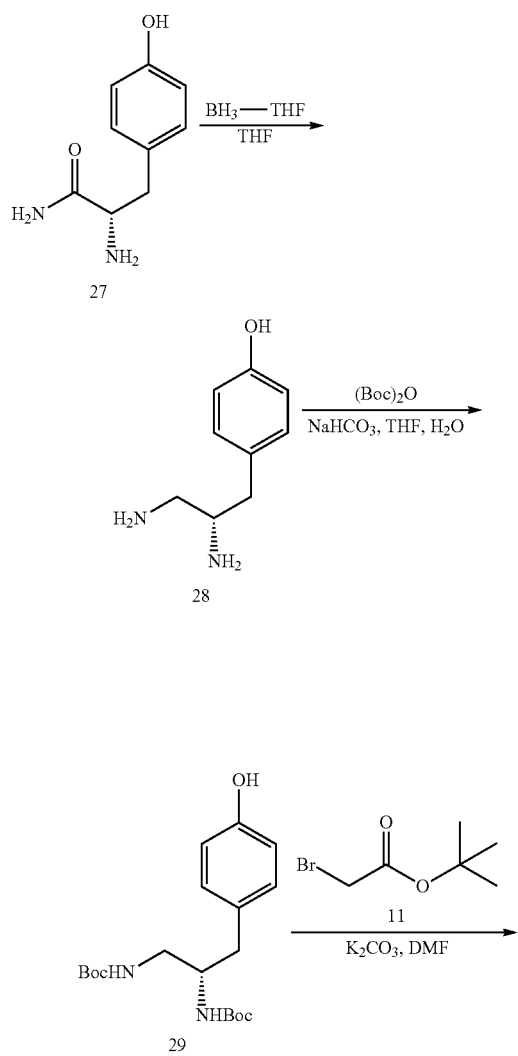

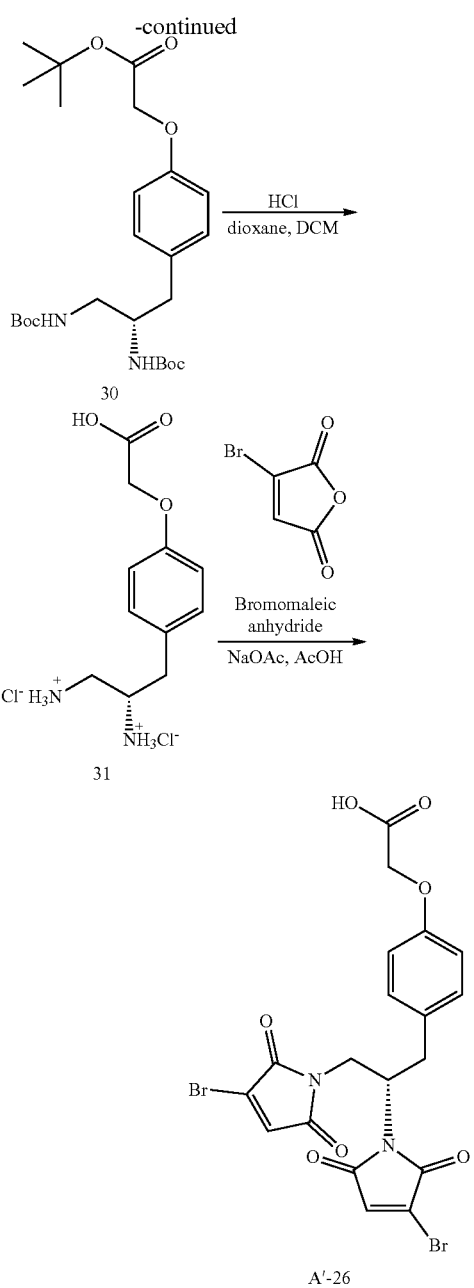

Compound 27 (150 mg, 0.63 mmol, 1.0 eq) was dissolved with 5 mL of anhydrous THF, and then cooled to −5° C. under the protection of Ar, to which was added carefully BH$_3$-THF (1N, 2.5 mL, 2.5 mmol, 4.0 eq), followed by stirring for 10 min, and then stirring at room temperature for 10 min. Thereafter, the solution was steadily heated up to 65° C., and reacted overnight. After the reaction was completed, the reaction solution was cooled down to 0° C., and 5 mL of methanol was slowly added dropwise to the reaction solution, followed by stirring for 30 min, and then stirring at room temperature for 10 min. Thereafter, the reaction solution was heated up to 60° C., stirred for 3 h, and concentrated under reduced pressure, to obtain a crude product of 140 mg of compound 28, as an oily liquid, which, without purification, was directly put into the next step. LC-MS (ESI$^+$) 167.1 [M+H]$^+$.

The crude product of compound 28 (140.0 mg, 0.58 mmol, 1.0 eq) was dissolved in 5 mL of THF, to which was added 3 mL of water, and then added dropwise a solution of Boc₂O (255.5 g, 1.17 mmol, 2.0 eq) in 2.5 mL of THF, followed by stirring at room temperature overnight. After the reaction was completed, the reaction solution was concentrated under reduced pressure. The residue, to which was added 30 mL of EA, was washed, dried, concentrated and purified to obtain 185 mg of compound 29, as a white solid, in a yield of 72%. LC-MS (ESI⁺) 367.1 [M+H]⁺.

Compound 29 (94.0 mg, 0.25 mmol, 1.0 eq) was dissolved in 3 mL of DMF, to which was added K₂CO₃ (71.0 mg, 0.51 mmol, 2.0 eq), and then added dropwise a solution of compound 11 (75.0 mg, 0.38 mmol, 1.5 eq) in 1 mL of DMF, followed by heating up to 55° C. and stirring overnight. After the reaction was completed, 20 mL of EA was added to the reaction solution. The reaction solution was adjusted with 30% citric acid solution to pH=3, extracted, washed, dried and concentrated to obtain 108 mg of compound 30, as an off-white solid, in a yield of 88%. LC-MS (ESI⁺) 481.3 [M+H]⁺.

Compound 30 (108 mg, 0.22 mmol, 1.0 eq) was dissolved in 5 mL of anhydrous DCM, to which was then added a solution (4 M, 1.5 mL, 6.0 mmol, 27.0 eq) of HCl in 1,4-dioxane, followed by stirring at room temperature for 3 h. After the reaction was completed, the reaction solution was concentrated under reduced pressure. The residue was dispersed by ultrasound with 10 mL of methyl tert-butyl ether, centrifuged with the removal of supernatant, and then dispersed with 10 mL of petroleum ether, centrifuged with the removal of supernatant. The solid was distilled under reduced pressure to remove the solvent, to obtain 66.6 mg of compound 31, as a white solid, in a yield of 100%. LC-MS (ESI⁺) 225.1 [M+H]⁺.

According to General procedure A, 66.6 mg of compound 31 was added, while other materials being added in molar ratios. The reaction was carried out at 70° C. overnight. The reaction solution was purified by normal phase column chromatography, to obtain 40 mg of the target compound A'-26, in a yield of 33%. LC-MS (ESI⁺) 540.9 [M+H]⁺.

Example 17 Synthesis of A'-27

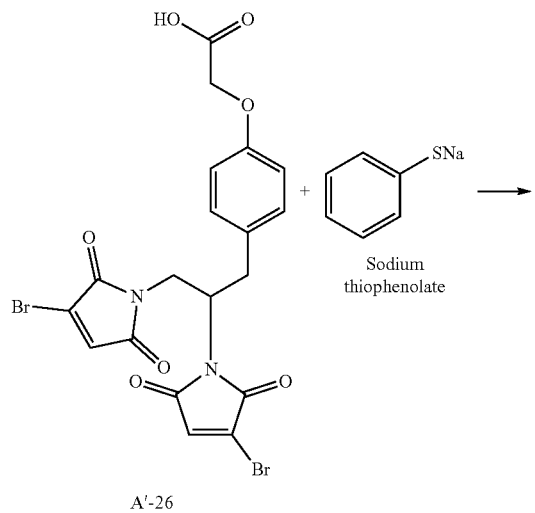

A'-26

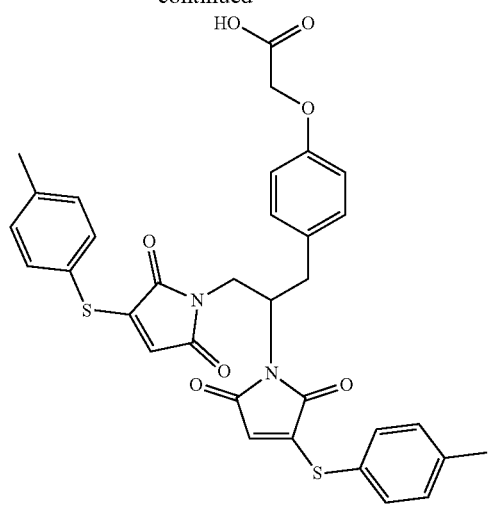

A'-27

Compound A'-26 (40.0 mg, 0.074 mmol, 1.0 eq) was dissolved with 1.0 mL of anhydrous THF, to which was added a solution of TEA (22.5 mg, 0.22 mmol, 3.0 eq) in 500 μL of THF, followed by stirring at room temperature for 5 min. Compound 32 (20.5 mg, 0.16 mmol, 2.2 eq) was dissolved in 500 μL of DMF, and added dropwise to the reaction solution, followed by stirring at room temperature overnight. After the reaction was completed, 15 mL of ethyl acetate was added to the reaction solution. The reaction solution was washed with 15% citric acid solution, washed with water, washed with saturated NaCl solution, dried, concentrated, and purified to obtain 12 mg of compound A'-27, as a white solid, in a yield of 26%. LC-MS (ESI⁺) 629.1 [M+H]⁺.

Example 18 Synthesis of A'-28

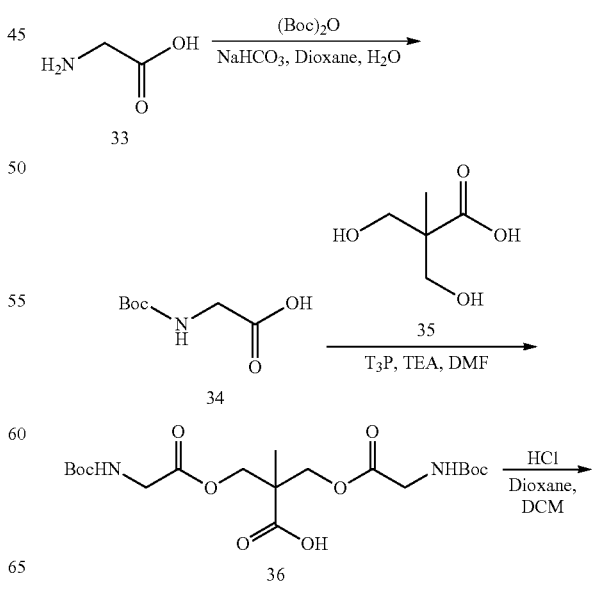

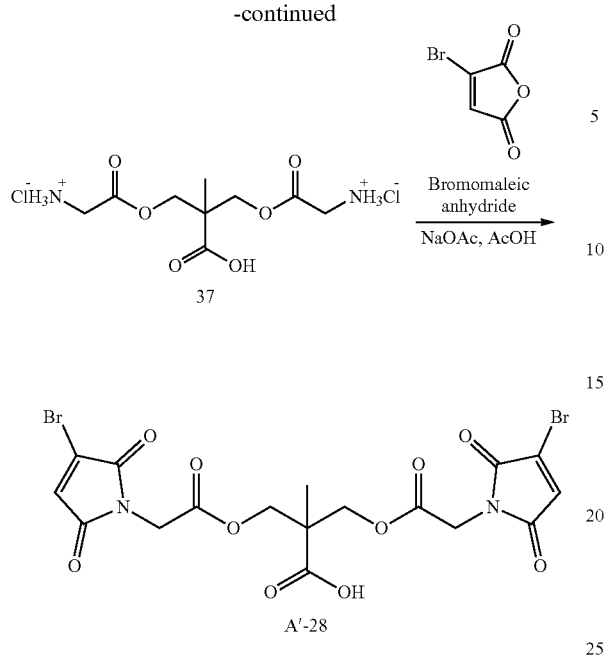

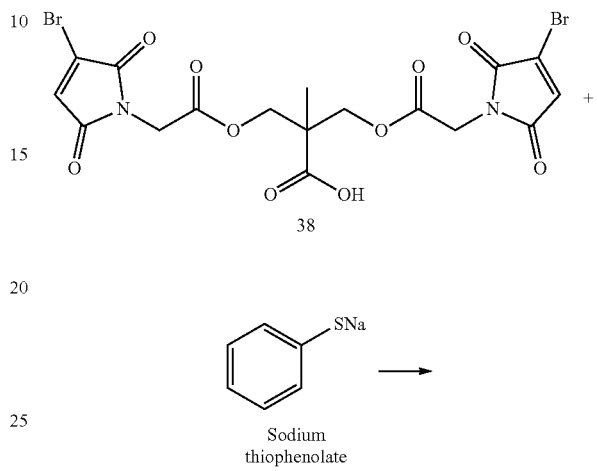

chromatography, to obtain 58 mg of the target compound A'-28, as a light yellow solid, in a yield of 17%. LC-MS (ESI+) 564.9 [M+H]+.

Example 19 Synthesis of A'-29

Compound 33 (150 mg, 2 mmol, 1.0 eq) was dissolved in 5 mL of dioxane, to which was added 3 mL of a saturated sodium bicarbonate aqueous solution, and then added dropwise a solution of Boc$_2$O (523 mg, 2.40 mmol, 1.2 eq) in 2.5 mL of dioxane, followed by stirring at room temperature for 2 h. The reaction solution was concentrated under reduced pressure. The residue, to which was added 30 mL of EA, was adjusted with 30% citric acid to pH=3, extracted, washed, dried, concentrated, dispersed with 15 mL of PE, filtered, and dried to obtain 344 mg of compound 34, in a yield of 62%. LC-MS (ESI+) 176.1 [M+H]+. Compound 34 (350 mg, 2.00 mmol, 1.0 eq) was dissolved in 4 mL of DMF, and cooled down to −15° C. under Ar atmosphere, to which was added a solution of TEA (606.0 mg, 6.00 mmol, 3.0 eq) in 1 mL of DMF, followed by stirring for 5 min, and then added a solution of T3P (700.0 mg, 2.20 mmol, 1.1 eq) in 1 mL of DMF, followed by stirring for 1.5 h. A solution of compound 35 (135.0 mg, 1.00 mmol, 0.5 eq) in 1 mL of DMF was added dropwise to the reaction solution, followed by stirring overnight. The reaction solution, in which was added 30 m$^1$ of EA, was adjusted with 30% citric acid to pH=3, extracted, washed, dried and concentrated to obtain 350 mg of compound 36 as an oily liquid, which, without purification, was directly put into the next step. LC-MS (ESI+) 449.2 [M+H]+.

Compound 36 (350 mg, 0.78 mmol, 1.0 eq) was dissolved with 5 mL of anhydrous DCM with stirring, to which was then added a solution (4 M, 2.0 mL, 8.0 mmol, 10.2 eq) of HCl in 1,4-dioxane, followed by stirring at room temperature for 2 h. The reaction solution was concentrated under reduced pressure. The residue was dispersed by ultrasound with 20 mL of methyl tert-butyl ether, centrifuged with the removal of supernatant, and then dispersed with 20 mL of petroleum ether, centrifuged with the removal of supernatant. The solid was distilled under reduced pressure to remove the solvent, to obtain 254 mg of compound 37, in a yield of 100%. LC-MS (ESI+) 249.1 [M+H]+.

According to General procedure A, 195 mg of compound 37 was added, while other materials being added in molar ratios. The reaction was carried out at 70° C. overnight. The reaction solution was purified by normal phase column

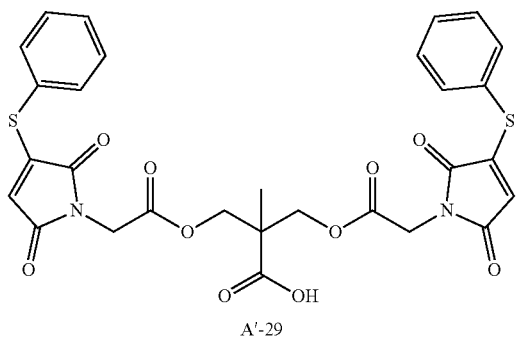

According to General procedure B, 58 mg of compound 38 was added, while other materials being added in molar ratios. The reaction was carried out at room temperature for 0.7 h. The reaction solution was purified by normal phase column chromatography, to obtain 14.1 mg of the target compound A'-29, in a yield of 22%. LC-MS (ESI+) 625.1 [M+H]+.

Example 20 Synthesis of A'-31

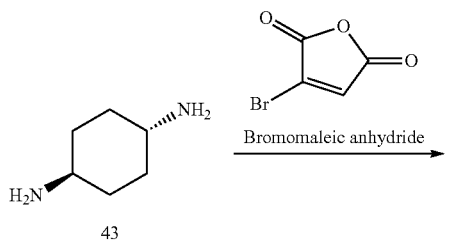

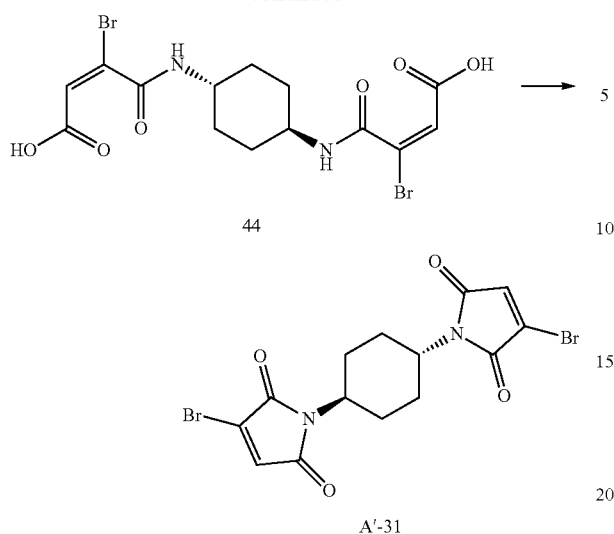

A'-31

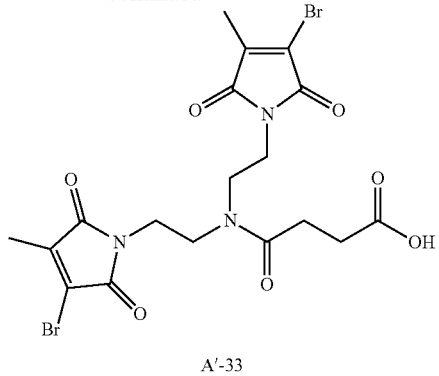

A'-33

According to General procedure A, compound 48 (95 mg, 0.5 mmol) and compound 8 (80.6 mg, 0.2 mmol) were added, to obtain 10.9 mg of compound A'-33, in a yield of 10.1%. LC-MS (ESI$^+$) 548.0 [M+H]$^+$.

Example 22 Synthesis of A'-34

Compound 43 (342.0 mg, 3.00 mmol, 1.0 eq) was dissolved with 15 mL of anhydrous THF, and to which was added dropwise bromomaleic anhydride (1110.0 mg, 6.30 mmol, 2.1 eq), followed by stirring at room temperature overnight. After the reaction was completed, the reaction solution was filtered. The filter cake was washed with DCM, and dried to obtain 1160 mg of compound 44, as a white solid, in a yield of 83%. LC-MS (ESI$^+$) 466.9 [M+H]$^+$.

To compound 45 (300 mg, 0.64 mmol, 1.0 eq) and anhydrous sodium acetate (158.0 mg, 1.93 mmol, 3.0 eq) was added 6 mL of acetic acid, followed by heating up to 85° C. and reacting overnight. The reaction solution was cooled to 45° C., and concentrated under reduced pressure. The residue, in which was added 20 mL of acetonitrile, was filtered. The filtrate was purified by preparative liquid chromatography to obtain 15 mg of a light yellow solid (i.e., compound A'-31), in a yield of 5%. LC-MS (ESI$^+$) 430.9 [M+H]$^+$.

Example 21 Synthesis of A'-33

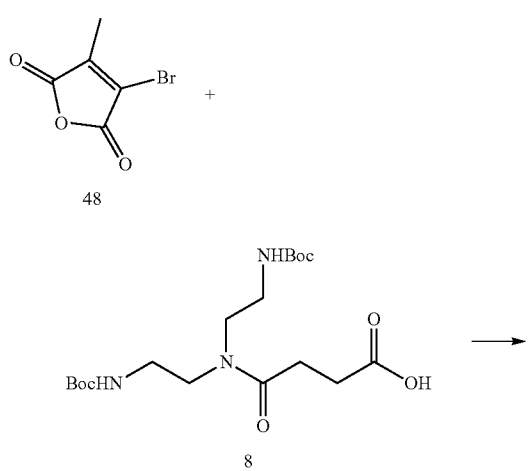

According to General procedure A, compound 49 (2-amino-6-chloroisonicotinic acid, 86 mg, 0.5 mmol) was added, to obtain 21.3 mg of compound A'-34, in a yield of 13%. LC-MS (ESI$^+$) 330.9 [M+H]$^+$.

Example 23 Synthesis of Conjugate (Ab-A) of Antibody (Ab) and First Linker Moiety (A)

The linker (i.e., first linker moiety A) provided by the present invention was mainly used for coupling with antibody in the antibody-drug conjugate. In order to verify the coupling ability of the linker provided by the present invention with antibody, the linker synthesized in the above examples was coupled separately with antibody. The coupling method used was as follows:

1) Preparation of mother liquors of reducing agent and protective agent: mother liquors of reducing agent and protective agent, 1~20 mM TCEP (Tris-2-carboxy-ethyl-phosphine) (reducing agent) and 1~20 mM DTPA (Diethylene triamine pentacetate acid) (protective agent), were respectively prepared with purified water;

2) Reduction reaction of antibody: the DTPA and TCEP mother liquors were added to a monoclonal antibody solution (e.g., 5-30 mg/mL) respectively. The DTPA mother liquor was mixed in the monoclonal antibody solution (e.g., 5-30 mg/mL) according to a certain volume ratio (1~5:10), and the molar ratio of TCEP to monoclonal antibody was 0.5~6.0:1. After the reducing agent and protective agent were added, the reaction was carried out at 25° C. with stirring for 1 h;
3) Preparation of first linker moiety (A) solution: a first linker moiety (A) was dissolved in 25% DMSO (dimethyl sulfoxide) to form a first linker moiety (A) solution in a concentration of 5 mM;
4) Coupling reaction between first linker moiety (A) and antibody: the first linker moiety (A) solution obtained in step 3) was slowly added to the reduced monoclonal antibody solution obtained in step 2), and, according to actual needs, while controlling the molar ratio of first linker moiety (A) to thio group of antibody to be in the range of 0.3~5:1, the reaction was carried out at 25° C. with stirring for 4 h;
5) Purification and detection steps: after the reaction of step 4) was completed, the reaction solution was centrifuged and ultrafiltered 3 times with PBS buffer to purify and remove residual unreacted chemicals and free small molecules such as DMSO, and the coupling result was detected by SDS-PAGE electrophoresis.

The coupling result of antibody-linker conjugate was analyzed by SDS-PAGE electrophoresis. The method used was as follows: for SDS-PAGE detection, a gel plate of NUPAGE 4-12% was used, 1.5 μL of a sample was put in a 1.5 mL EP tube, 2.5 μL of buffer was added, then 1.5 μL of reducing agent was added, and water was added to make the volume to 10 μL. The mixture was mixed on an oscillator, and heated in a microwave oven for 1 min. After the sample was loaded, gel electrophoresis was performed. After the gel electrophoresis was completed, the gel was taken out and put in a fresh-keeping box, to which was added 50 mL of a quick stain, heated in a microwave oven for 5 min, and then dyed on a shaker for 5 min. After the staining solution was poured out, 100 mL of purified water was added, heated in an induction cooker for 5 min, and decolored on a shaker for 1 h. This operation was repeated three times.

The antibody used here was Her2 monoclonal antibody (as for the sequence information of the antibody, please refer to paragraphs 41, 42, 43 of the specification in Chinese Patent Publication No. CN105008398B), and the linkers were:

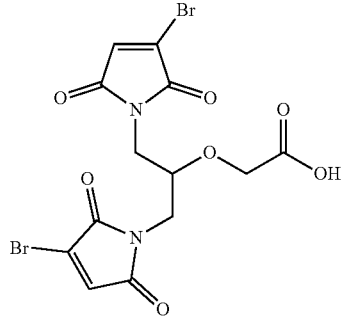

A'-8

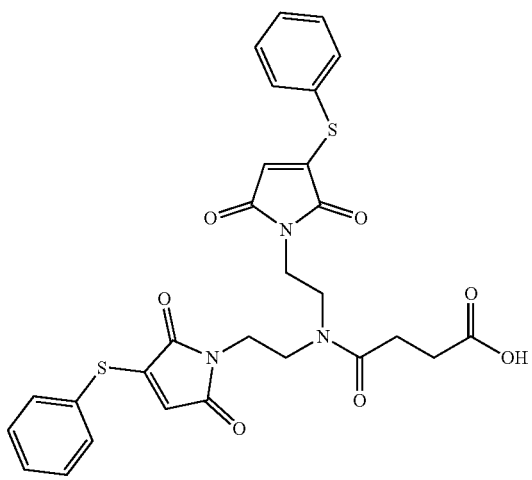

A'-10

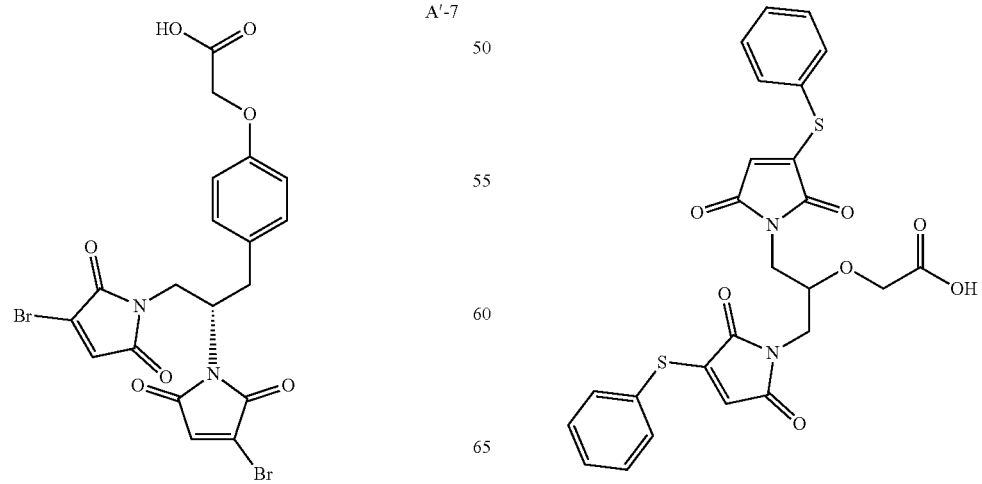

A'-7

A'-11

-continued

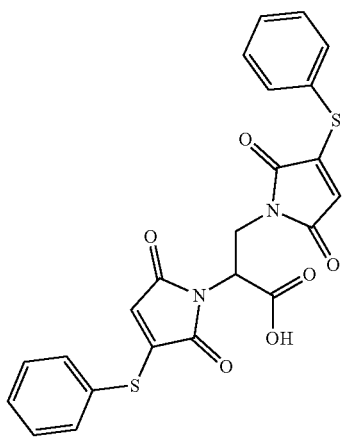
A'-12

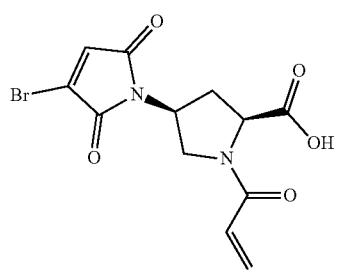
A'-20

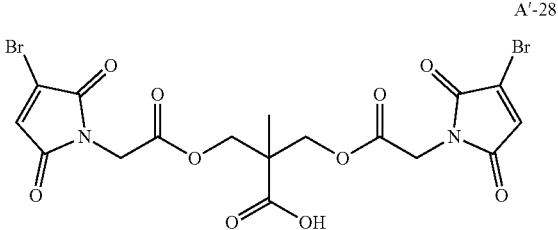
A'-28

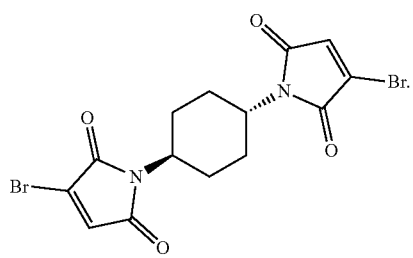
A'-31

Figure 5:
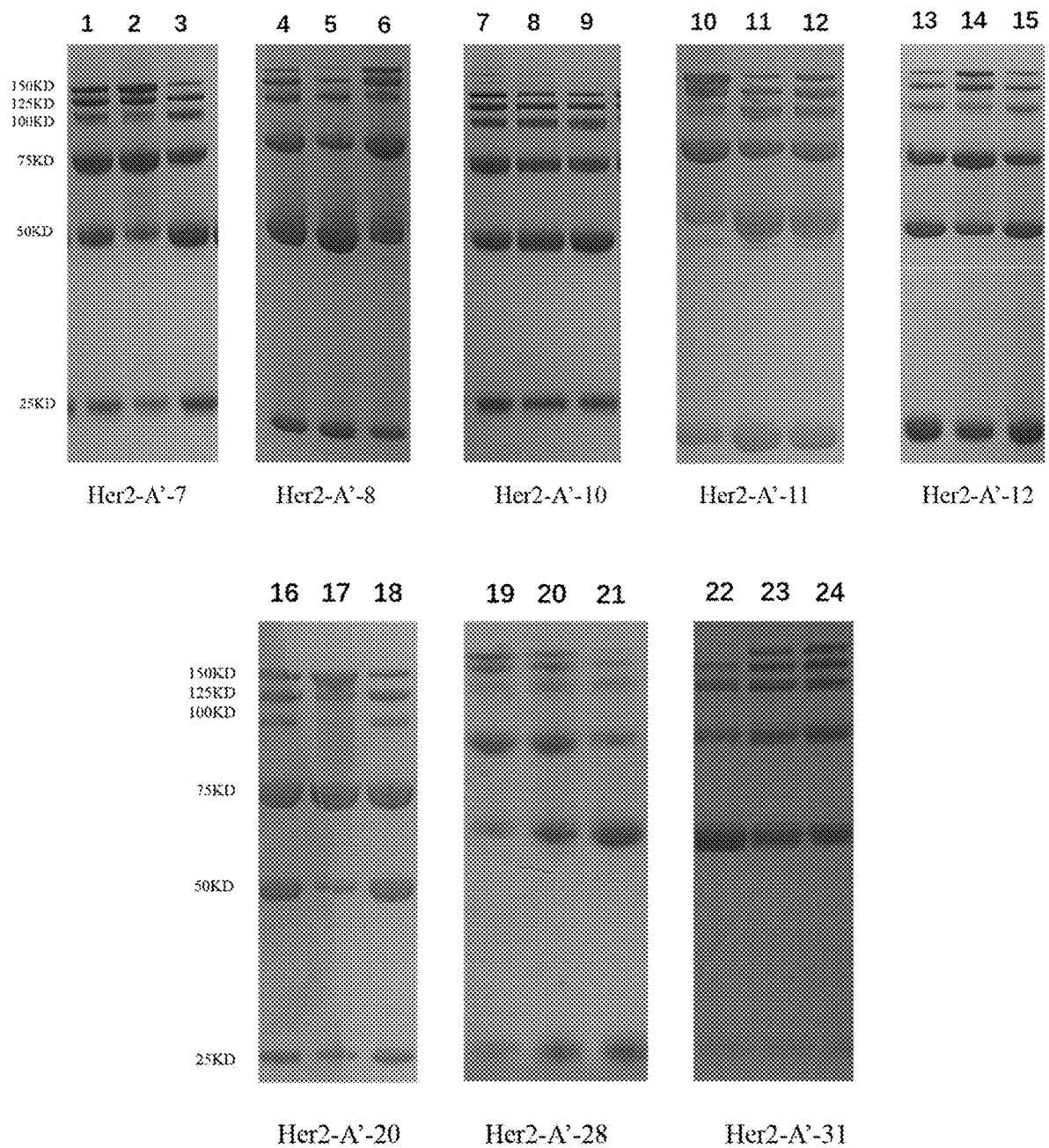
FIG. 5 shows coupling results of conjugates (Ab-A) of antibody (Ab) and first linker moiety (A), wherein Nos. 1, 2, 3 are Her2-A'-7, coupling buffers respectively have pH of 8.5, 9.0, 7.4; Nos. 4, 5, 6 are Her2-A'-8, coupling buffers respectively have pH of 8.5, 7.4, 9.0; Nos. 7, 8, 9 are Her2-A'-10, coupling buffers respectively have pH of 8.5, 9.0, 7.4; Nos. 10, 11, 12 are Her2-A'-11, coupling buffers respectively have pH of 9.0, 7.4, 9.5; Nos. 13, 14, 15 are Her2-A'-12, coupling buffers respectively have pH of 7.4, 9.0, 8.5; Nos. 16, 17, 18 are Her2-A'-20, coupling buffers respectively have pH of 8.5, 9.0, 7.4; Nos. 19, 20, 21 are Her2-A'-28, coupling buffers respectively have pH of 9.0, 8.5, 7.4; Nos. 22, 23, 24 are Her2-A'-31, coupling buffers respectively have pH of 7.4, 8.5, 9.0.

The coupling results were as shown in FIG. 5. In FIG. 5, Nos. 1, 2, 3 were Her2-A'-7, coupling buffers respectively had pH of 8.5, 9.0, 7.4; Nos. 4, 5, 6 were Her2-A'-8, coupling buffers respectively had pH of 8.5, 7.4, 9.0; Nos. 7, 8, 9 were Her2-A'-10, coupling buffers respectively had pH of 8.5, 9.0, 7.4; Nos. 10, 11, 12 were Her2-A'-11, coupling buffers respectively had pH of 9.0, 7.4, 9.5; Nos. 13, 14, 15 were Her2-A'-12, coupling buffers respectively had pH of 7.4, 9.0, 8.5; Nos. 16, 17, 18 were Her2-A'-20, coupling buffers respectively had pH of 8.5, 9.0, 7.4; Nos. 19, 20, 21 were Her2-A'-28, coupling buffers respectively had pH of 9.0, 8.5, 7.4; Nos. 22, 23, 24 were Her2-A'-31, coupling buffers respectively had pH of 7.4, 8.5, 9.0.

Due to the use of reduction electrophoresis, all the thio groups among antibodies were exposed. Therefore, in FIG. 5, 25 KD represented the molecular weight of one light chain of the antibody, 50 KD represented the molecular weight of one heavy chain, and 75 KD represented the molecular weight of one light chain and one heavy chain (i.e., one linker was covalently linked to the thio group between one heavy chain and one light chain), 100 KD represented the molecular weight of two heavy chains (i.e., one linker was covalently linked to the thio group between two heavy chains), 125 KD represented the molecular weight of one light chain and two heavy chains (i.e., one linker was covalently linked to the thio groups among two heavy chains and one light chain), 150 KD represented the molecular weight of two heavy chains and two light chains (i.e., one linker was covalently linked to the thio groups among two heavy chains and two light chains).

The results showed that the above antibody-linker conjugates each had linkers that were simultaneously covalently linked to the thio groups respectively between one heavy chain and one light chain, between two heavy chains, among two heavy chains and one light chain, or among two heavy chains and two light chains. And, there were 150-75 KD bands in most antibody-linker conjugates, which proved that the 4 pairs of disulfide bonds in the antibody were fully or partially bridged, and the bridge coupling effect was better. From FIG. 5, it could also be seen that the coupling result under the condition of buffer pH=9.0 was better than that under the conditions of pH=8.5 and 7.4.

In view of the better bridging coupling effect of the linker provided by the present invention with antibody, A'-7, A'-8, A'-10, A'-11, A'-28 were selected for the preparation of antibody-drug conjugates. The antibody used was Her2 monoclonal antibody (the same as above), and the drugs used were MMAE, MMAF, MMAD, CBI, DM1, DM4.

As for MMAE and MMAD, the preparation of the antibody-drug conjugate involved in the present invention was generally divided into three steps: the first step was to prepare a conjugate L-D of second linker L and drug D; the second step was to prepare a conjugate A-L-D of first linker A and L-D; and the third step was to prepare a conjugate of antibody Ab and A-L-D, i.e., an antibody-drug conjugate Ab-A-L-D.

As for MMAF, CBI, DM1, DM4, the preparation of the antibody-drug conjugate involved in the present invention was generally divided into two steps: the first step was to prepare a conjugate A-D of first linker A and drug D; and the second step was to prepare a conjugate of antibody Ab and A-D, i.e., an antibody-drug conjugate Ab-A-D.

The specific preparation method was shown in Examples 26-29.

Example 24 Synthesis of Conjugate (L-D) of Second Linker Moiety (L) and Drug (D)

General method for the synthesis of L-D: a second linker moiety L was dissolved in a suitable amount of DMF, to which were added, under the protection of nitrogen gas, drug (D), HOBt, DIPEA and pyridine in suitable amounts, followed by stirring at room temperature for 24 hours, while TLC was used to monitor the progress of the reaction. After the reaction was completed, the reaction solution was purified by preparative high performance liquid chromatography, and the preparation solution was lyophilized to obtain a conjugate (L-D) of the second linker moiety and the drug.

Val-Cit-PAB-MMAE was prepared by the general method described above, and the synthetic route was shown below:

Compound 53 (i.e., Fomc-Val-Cit-PAB-PNP, 995.4 mg, 1.3 mmol) and HOBt (67.6 mg, 0.65 mmol) were put in a reaction bottle, and dissolved with 5 mL of anhydrous DMF, to which was added DIPEA (258.5 mg, 2 mmol), followed by stirring at room temperature for 10 min. Compound 54 (i.e., MMAE, 717 mg, 1 mmol) was dissolved in 5 mL of anhydrous DMF, and added dropwise to the reaction solu-

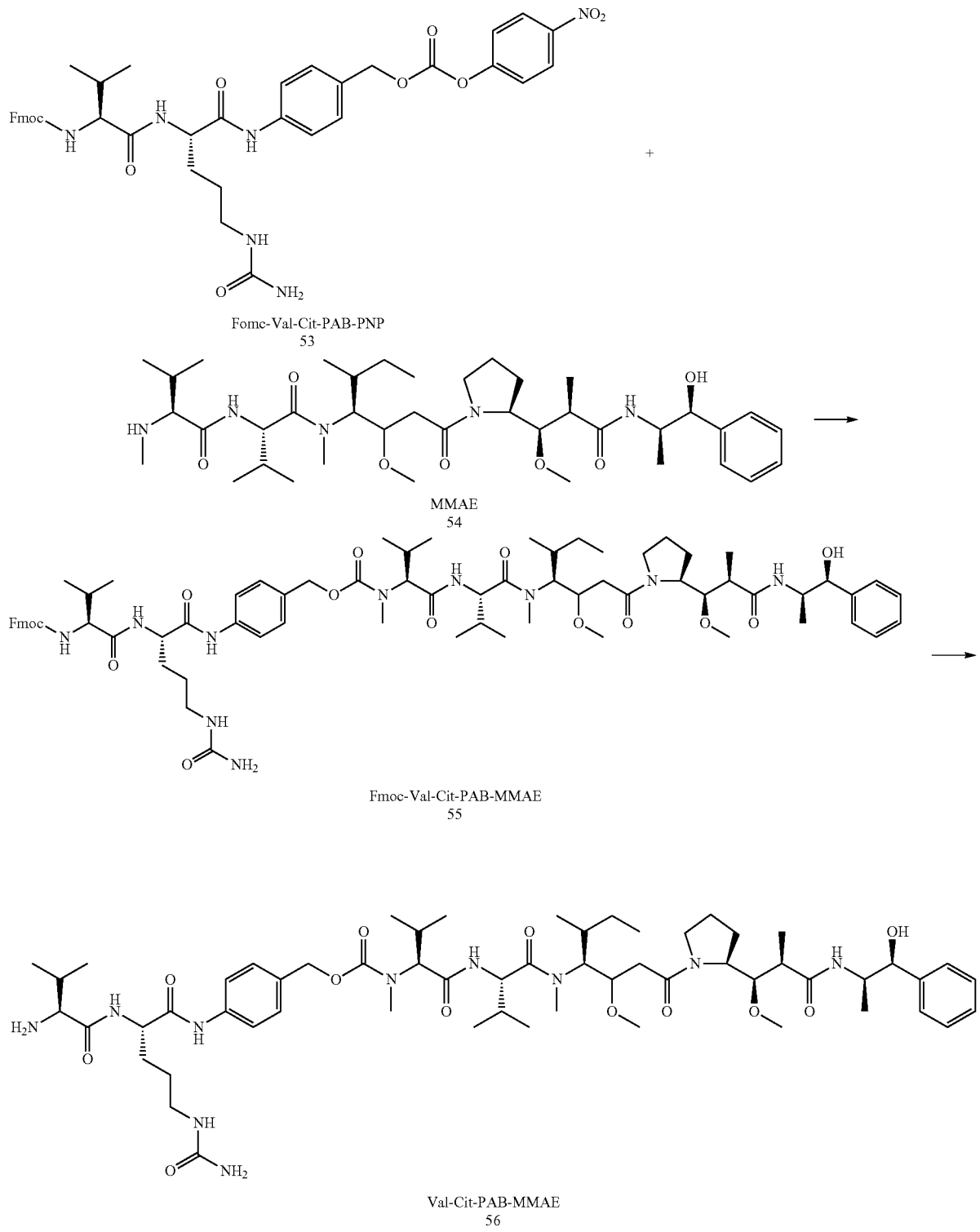

tion, followed by stirring at room temperature overnight. After the reaction was completed, the reaction solution was filtered. The organic phase was concentrated. The residue was separated by preparative liquid chromatography to obtain 636.2 mg of compound 55 (i.e., Fmoc-Val-Cit-PAB-MMAE), as a white solid, in a yield of 47.3%, LC-MS (ESI⁺) 1345.8 [M+H]⁺.

Compound 55 (270 mg, 0.2 mmol) was added to 3 mL of a 20% solution of piperidine in acetonitrile (v/v), followed by stirring at room temperature for 2.5 h, to gradually dissolve the solid. After the reaction was completed, the reaction solution was distilled under reduced pressure to remove the solvent. The residue was separated by preparative liquid chromatography, to obtain 214 mg of compound 62 (i.e., Val-Cit-PAB-MMAE), in a yield of 95%. LC-MS (ESI⁺) 1123.7 [M+H]⁺.

The synthesis with the use of second linker moiety (L) and drug (D) was a general method for the synthesis of other L-D compounds, such as Val-Cit-PAB-MMAD.

Example 25 Synthesis of Conjugate (A-L-D) of First Linker Moiety (A) and Second Linker Moiety-Drug Conjugate (L-D)

General method for the synthesis of A-L-D: first linker moiety, EDCI, HOBt in suitable amounts were dissolved in a suitable amount of anhydrous DMF, and stirred at room temperature for 2 h. A suitable amount of self-made L-D was dissolved in a suitable amount of anhydrous DMF, and slowly added dropwise to the reaction solution, followed by stirring at room temperature for 4 h. After the reaction was completed, the reaction solution was diluted with acetonitrile, and then separated by preparative liquid chromatography. The eluent was lyophilized to obtain a conjugate of first linker moiety (A) and second linker moiety-drug conjugate (L-D).

Conjugate of A'-7 and compound 56 (Val-Cit-PAB-MMAE) was synthesized by using the above general method. The synthetic route was shown below:

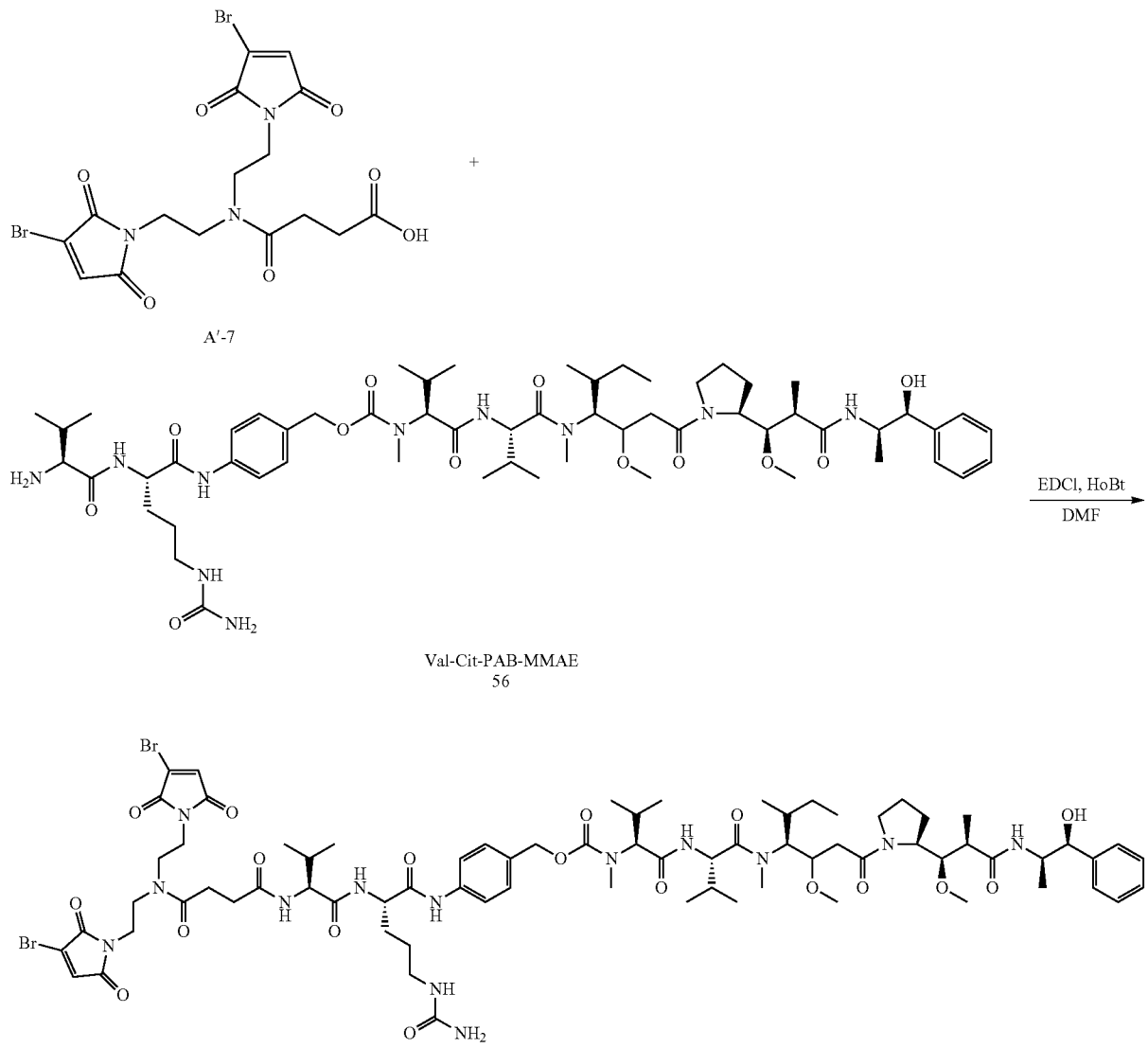

Compound A'-7 (27.8 mg, 0.053 mmol), EDCI (11.2 mg, 0.058 mmol), HOBt (1.4 mg, 0.01 mmol) were dissolved in 0.3 mL of anhydrous DMF, and stirred at room temperature for 2 h. Compound 56 (i.e., Val-Cit-PAB-MMAE, 40 mg, 0.035 mmol) was dissolved in 0.2 mL of anhydrous DMF, and added dropwise to the reaction solution, followed by stirring at room temperature for 4 h. After the reaction was completed, the reaction solution was diluted with 2 mL of acetonitrile, and then separated by preparative liquid chromatography. The eluent was lyophilized to obtain 8.6 mg of compound 57 (i.e., A'-7-Val-Cit-PAB-MMAE), as a light yellow solid, in a yield of 15%. LC-MS (ESI$^+$) 1624.6 [M+H]$^+$.

Other conjugates of first linker moiety and L-D compound were synthesized by using the above general method, such as A'-8-Val-Cit-PAB-MMAE, A'-10-Val-Cit-PAB-MMAE, A'-11-Val-Cit-PAB-MMAE, A'-11-Val-Cit-PAB-MMAD, A'-28-Val-Cit-PAB-MMAE and the like.

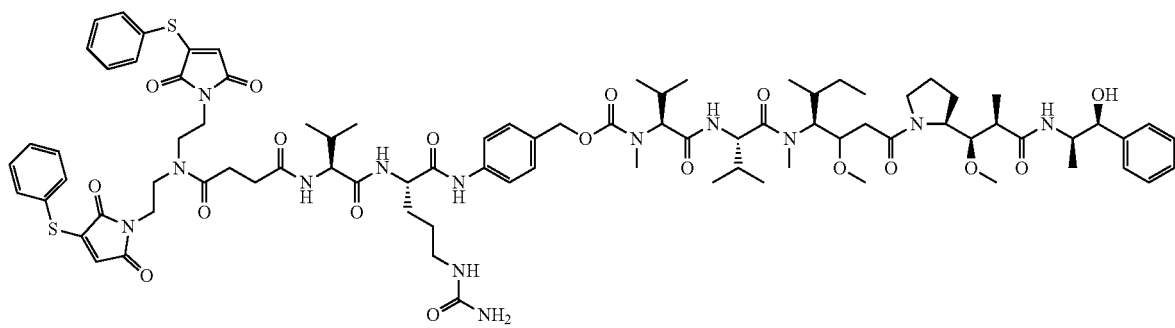

A'-10-Val-Cit-PAB-MMAE

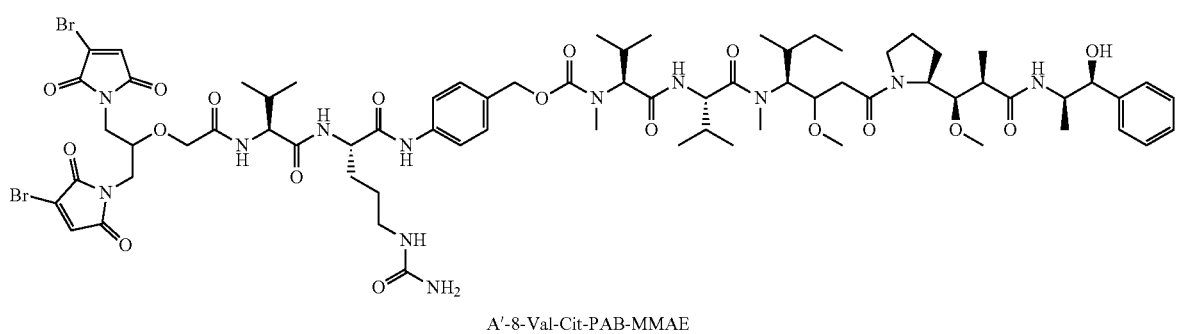

A'-8-Val-Cit-PAB-MMAE

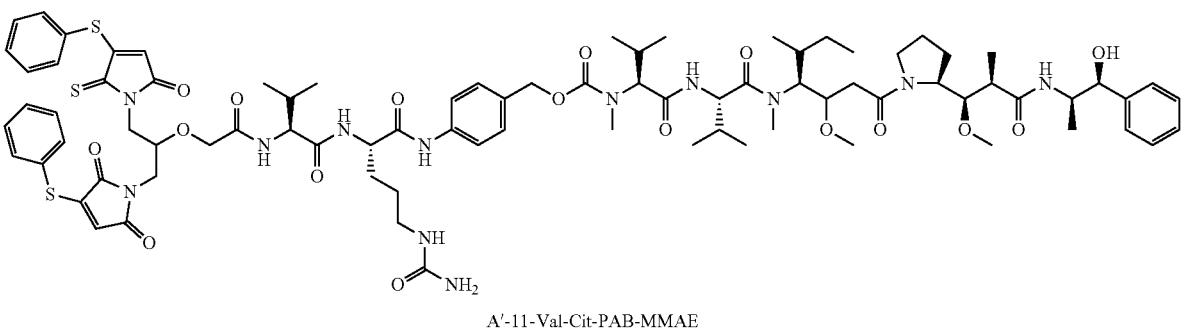

A'-11-Val-Cit-PAB-MMAE

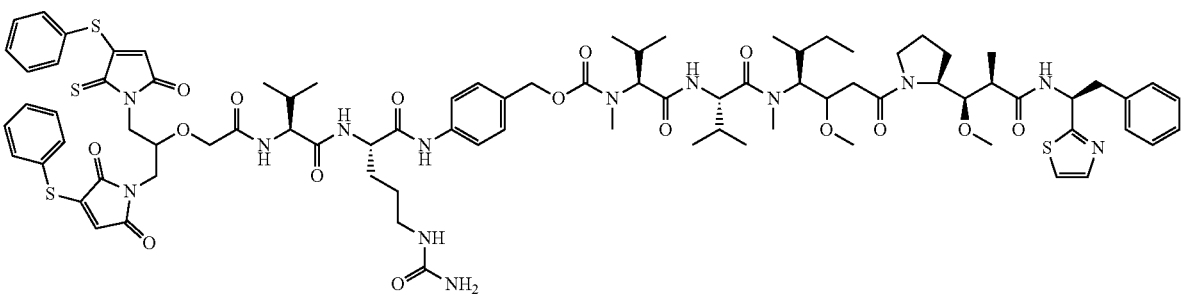

A'-11-Val-Cit-PAB-MMAD

-continued

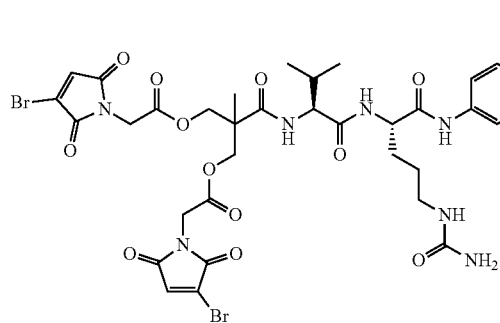
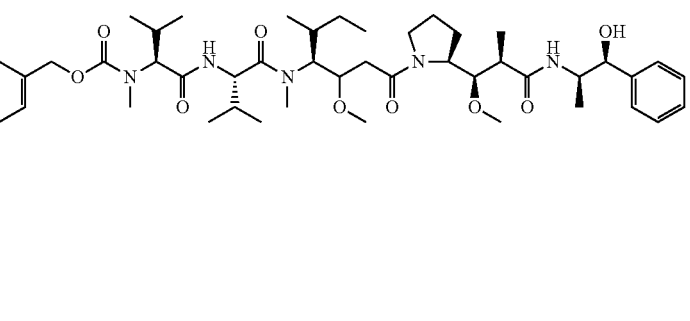

A'-28-Val-Cit-PAB-MMAE

For comparison, a conjugate 575DZ-Val-Cit-PAB-MMAE of compound 6 (this compound is defined herein as 575DZ) disclosed on page 7 of the claims of the Chinese patent No. CN103933575A with second linker moiety (Val-Cit-PAB) and drug moiety (MMAE) was also prepared here.

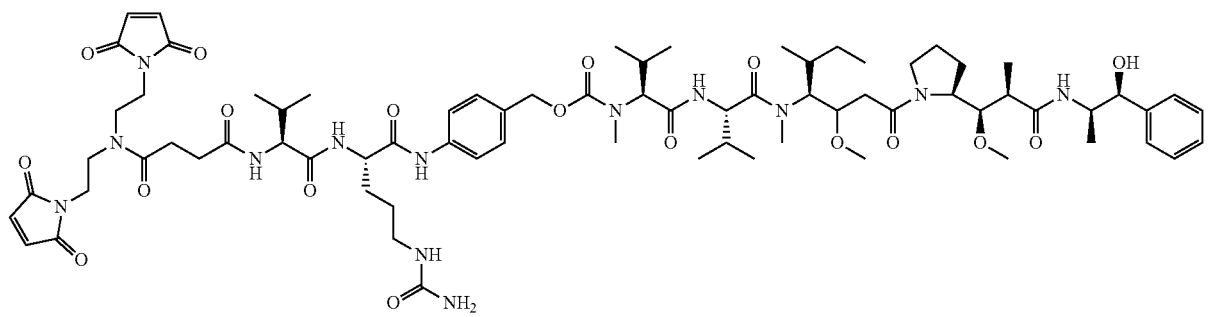

575DZ-Val-Cit-PAB-MMAE

Example 26 Synthesis of Conjugate (A-D) of First Linker Moiety (A) and Drug (D)

(1) Synthesis of A'-7-MMAF

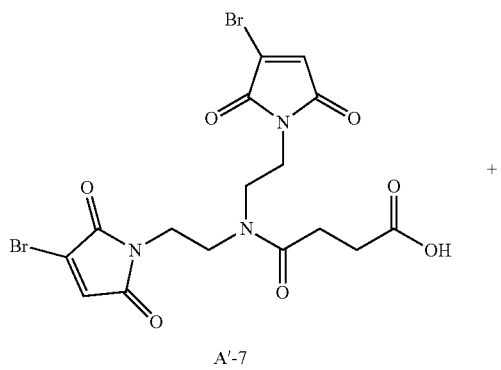

A'-7

-continued

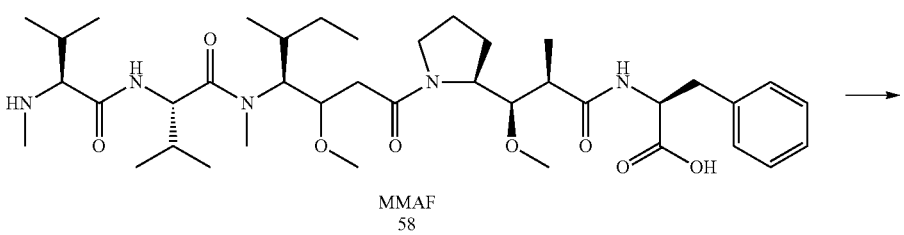

MMAF
58

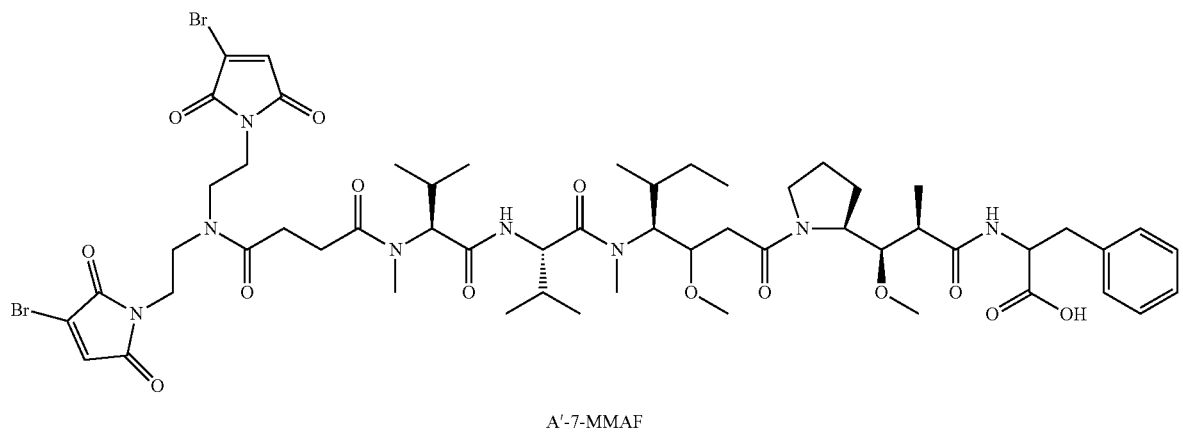

A'-7-MMAF

Compound A'-7 (51.8 mg, 0.1 mmol), EDCI (21.1 mg, 0.11 mmol), HOBt (2.7 mg, 0.01 mmol) were dissolved in 2 mL of anhydrous DMF, and stirred at room temperature for 2 h. Compound 58 (i.e., MMAF, 48.8 mg, 0.066 mmol) was dissolved in 0.8 mL of anhydrous DMF, and added dropwise to the reaction solution, followed by stirring at room temperature for 4 h. After the reaction was completed, the reaction solution was diluted with 4 mL of acetonitrile, and separated by preparative liquid chromatography. The eluent was lyophilized to obtain 25.9 mg of compound A'-7-MMAF, as a light yellow solid, in a yield of 21%. LC-MS (ESI$^+$) 1233.4 [M+H]$^+$.

(2) Synthesis of A'-8-CBI

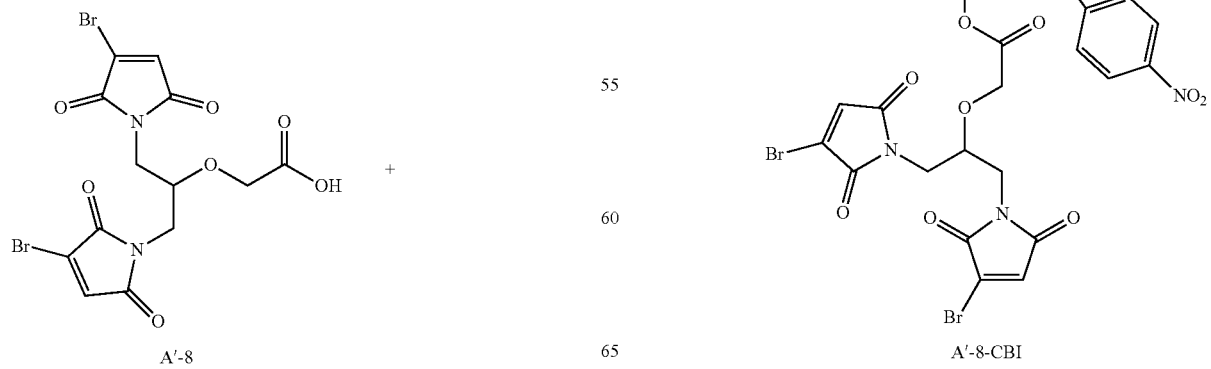

The synthesis method was the same as that of A'-7-MMAF. A'-8 (22.0 mg, 0.047 mmol, 1.0 eq) and compound 59 (i.e., CBI, 14.0 mg, 0.020 mmol, 0.7 eq) were added, to obtain 6.0 mg of a white solid A'-8-CBI, in a yield of 21%. LC-MS (ESI$^+$) 868.0 [M+H]$^+$.
(3) Synthesis of A'-8-DM1
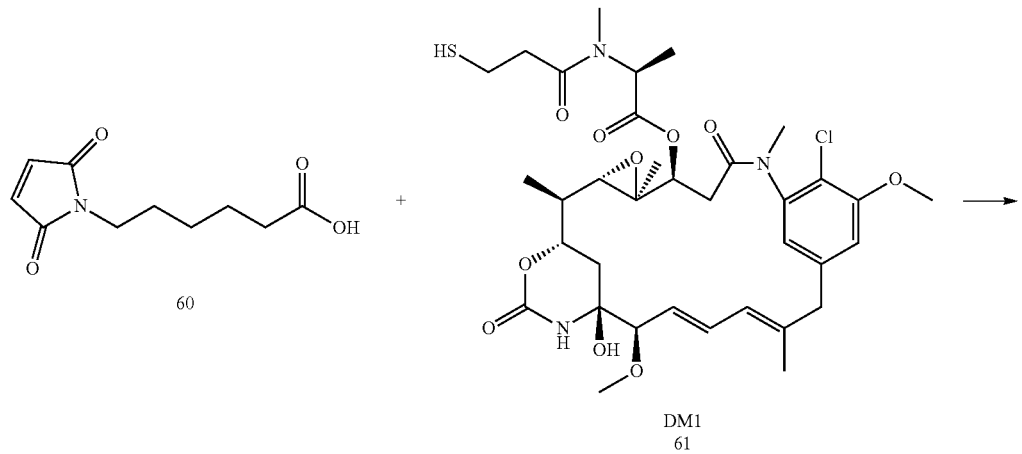
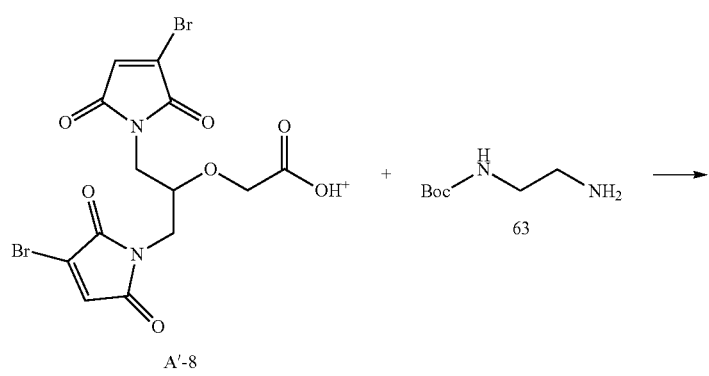

-continued

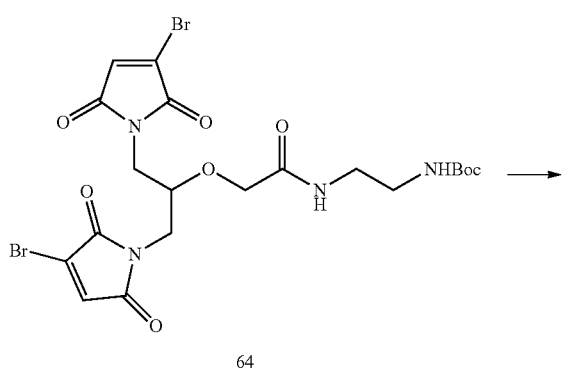

64

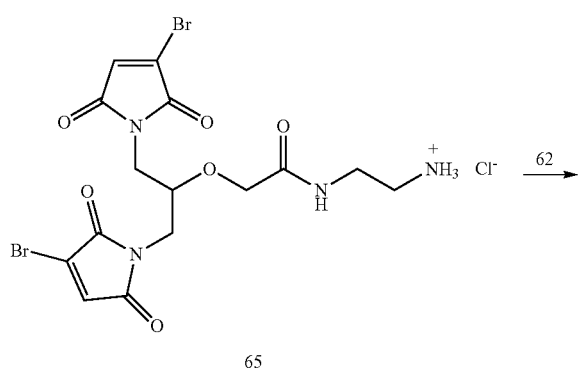

65

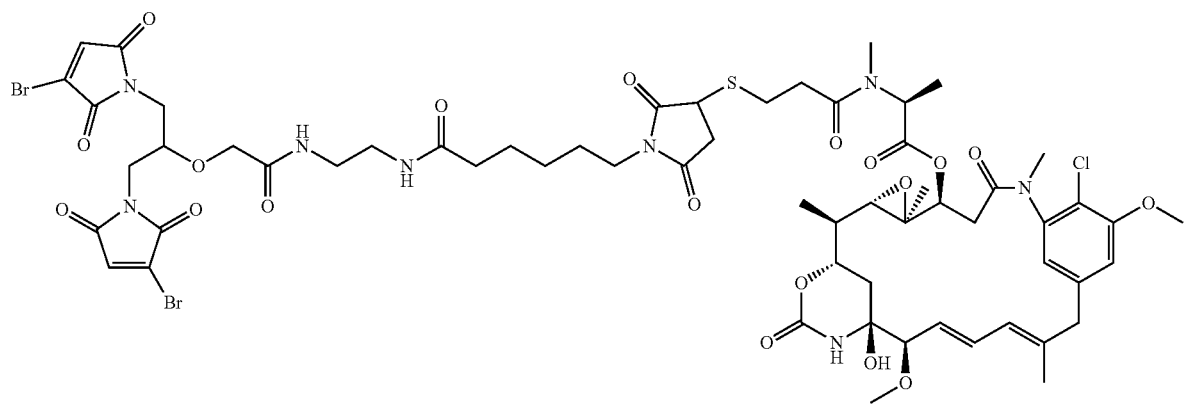

A'-8-DM1

Compound 60 (45.0 mg, 0.21 mmol, 1.0 eq) was dissolved with 2 mL of anhydrous THF, to which was added 1 mL of sat. NaHCO$_3$ aqueous solution, and added dropwise a solution of DM1 (61, 150.0 mg, 0.21 mmol, 1.0 eq) in 1 mL of DMF, followed by stirring at room temperature for 2 h. The reaction solution was diluted with 10 mL of water, and extracted with EA. The aqueous phase was adjusted with 15% citric acid solution to pH=3, extracted with 15 mL of EA, washed with saturated NaCl, dried and concentrated to obtain 165.7 mg of compound 62, as a white solid, in a yield of 85%. LC-MS (ESI$^+$) 949.3 [M+H]$^+$.

A'-8 (150.0 mg, 0.33 mmol, 1.0 eq) was dissolved in 5 mL of DMF, and cooled down to −15° C. under Ar atmosphere, to which was added a solution of TEA (98.0 mg, 0.99 mmol, 3.0 eq) in 1 mL of DMF, followed by stirring for 5 min, and then added a solution of T3P (154.0 mg, 0.48 mmol, 1.5 eq) in 1 mL of DMF, followed by stirring for 1.5 h. A solution of compound 63 (46.0 mg, 0.29 mmol, 0.9 eq) in 1 mL of DMF was added dropwise to the reaction solution, followed by stirring overnight. After the reaction was completed, 30 mL of EA was added, and the reaction solution was adjusted with 30% citric acid to pH=3, extracted, washed, dried, concentrated, and purified by normal phase column chromatography to obtain 90 mg of compound 64, as a white solid, in a yield of 52%. LC-MS (ESI$^+$) 607.1 [M+H]$^+$.

Compound 64 (90 mg, 0.15 mmol, 1.0 eq) was dissolved with 3 mL of anhydrous DCM with stirring, to which was then added a solution (4 M, 1.0 mL, 4 mmol, 26.7 eq) of HCl in 1,4-dioxane, followed by stirring at room temperature for 2 h. The reaction solution was concentrated under reduced pressure. The residue was dispersed by ultrasound with 20 mL of methyl tert-butyl ether, centrifuged with the removal of supernatant, and then dispersed with 20 mL of petroleum ether, centrifuged with the removal of supernatant. The solid was distilled under reduced pressure to remove the solvent, to obtain 82 mg of compound 65, as a white solid, in a yield of 100%. LC-MS (ESI$^+$) 506.9 [M+H]$^+$.

Compound 62 (30.0 mg, 0.03 mmol, 1.0 eq) was dissolved in 2 mL of DMF, and cooled down to −15° C. under Ar atmosphere, to which was added a solution of TEA (11.0 mg, 0.095 mmol, 4.0 eq) in 500 μL of DMF, followed by stirring for 5 min, and then added a solution of T3P (15.0 mg, 0.047 mmol, 1.5 eq) in 500 μL of DMF, followed by stirring for 1.5 h. A solution of compound 65 (19.0 mg, 0.035 mmol, 1.1 eq) in 500 μL of DMF was added dropwise to the reaction solution, followed by stirring overnight. After the reaction was completed, the reaction solution was diluted with 2 mL of acetonitrile, and purified by preparative liquid chromatography, to obtain 9 mg of the product A'-8-DM1, in a yield of 20%. LC-MS (ESI$^+$) 1437.3 [M+H]$^+$.

(4) Synthesis of A'-7-DM4

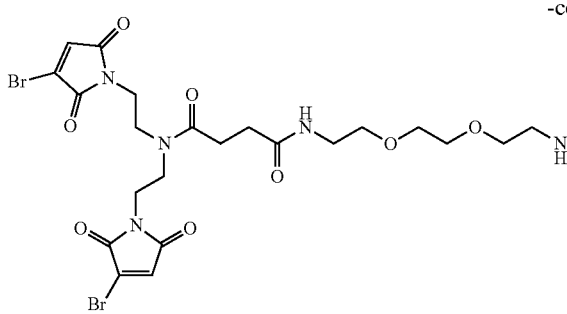
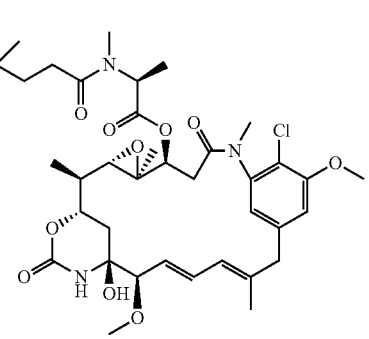

A'-7-DM4

Compound 67 (737.5 mg, 4.03 mmol), EDCI (846.13 mg, 4.43 mmol), HOBt (108.9 mg, 0.806 mmol) were dissolved in 10 mL of DCM, followed by stirring at room temperature for 2 h. Compound 66 (1 g, 4.03 mmol) was dissolved in 5 mL of dichloromethane, and slowly added dropwise in 3 batches to the reaction system, followed by stirring at room temperature overnight. After the reaction was completed, the reaction solution was concentrated under reduced pressure to remove the solvent. The residue was dissolved with 6 mL of acetonitrile/water (1:1), separated by preparative liquid chromatography, and lyophilized to obtain 1.11 g of compound 68, as a colorless oily compound, in a yield of 67%. LC-MS (ESI$^+$) 414.2 [M+H]$^+$.

Compound 68 (1.11 g, 2.7 mmol) was dissolved with 1.1 mL of DMA. 0.1 mL of the obtained solution was dissolved in 1 mL of DMA, to which was added DIPEA (41.3 mg, 0.32 mmol), followed by stirring at room temperature for 2 min, and then added DM4 (69, 202.5 mg, 0.26 mmol), followed by stirring at room temperature for 6 h. The reaction solution was directly separated by preparative liquid chromatography, and lyophilized to obtain 260 mg of compound 70, as a white solid, in a yield of 84%. LC-MS (ESI$^+$) 1193.5 [M+H]$^+$.

The synthesis method of compound 71 was the same as that of compound 65. 119.3 mg of compound 70 was added, to obtain 106 mg of compound 71, as a white solid, in a yield of 96%. LC-MS (ESI+) 1093.5 [M+H]+.

The synthesis method of A'-7-DM4 was the same as that of A'-8-DM1. 52 mg of A'-7 and 54.6 mg of compound 71 were added, to obtain 15 mg of A'-8-DM1, as a white solid, in a yield of 19%. LC-MS (ESI$^+$) 1594.4 [M+H]$^+$.

Example 27 Synthesis of Antibody-Drug Conjugate and Product Uniformity Analysis

General method for the synthesis of antibody-drug conjugate:
1) Preparation of mother liquors of reducing agent and protective agent: mother liquors of reducing agent and protective agent, 1~20 mM TCEP (Tris-2-carboxyethyl-phosphine) (reducing agent) and 1~20 mM DTPA (Diethylene triamine pentacetate acid) (protective agent), were respectively prepared with purified water;
2) Reduction reaction of antibody: the DTPA and TCEP mother liquors were added to a monoclonal antibody solution (e.g., 5-30 mg/mL) respectively. The DTPA mother liquor was mixed with the monoclonal antibody solution (e.g., 5-30 mg/mL) according to a certain volume ratio (1~5:10), and the molar ratio of TCEP to monoclonal antibody was 0.5~6.0:1. After the reducing agent and protective agent were added, the reaction was carried out at 25° C. with stirring for 1 h.
3) Synthesis of A-L-D and preparation of solution: a conjugate (A-L-D) of first linker moiety-second linker moiety-drug moiety was synthesized, and the synthesized A-L-D was dissolved in 25% DMSO (dimethyl sulfoxide) to obtain a A-L-D solution with concentration of 5 mM;
4) Coupling reaction of drug and antibody: the A-L-D solution obtained in step 3) was slowly added to the reduced monoclonal antibody solution obtained in step 1), and, according to actual needs, while controlling the molar ratio of A-L-D to thio group of antibody to be in the range of 0.3~5:1, the reaction was carried out at 25° C. with stirring for 4 h;
5) Purification and detection steps: after the reaction of step 4) was completed, the reaction solution was centrifuged and ultrafiltered 3 times with PBS buffer to purify and remove residual unreacted chemcials and free small molecules such as DMSO, and the coupling result was detected by SDS-PAGE electrophoresis and hydrophobic high performance liquid chromatography (HIC-HPLC).

The coupling result of the antibody-drug conjugate was analyzed by SDS-PAGE electrophoresis and HIC-HPLC. The method used was shown as follows:
1) Polyacrylamide Gel Electrophoresis (SDS-PAGE)

For SDS-PAGE detection, a gel plate of NUPAGE 4-12% was used, 1.5 µL of a sample was put in a 1.5 mL EP tube, 2.5 UL of buffer was added, then 1.5 µL of reducing agent was added, and water was added to make the volume to 10 µL, followed by mixing on an oscillator, and heating in a microwave oven for 1 min. After the sample was loaded, gel electrophoresis was performed. After the gel electrophoresis was completed, the gel was taken out and put in a fresh-keeping box, to which was added 50 mL of a quick stain, and heated in a microwave oven for 5 min, and then dyed on a shaker for 5 min. After the staining solution was poured out, 100 mL of purified water was added, heated in an induction cooker for 5 min, and decolored on a shaker for 1 h. This operation was repeated three times.

2) Hydrophobic High Performance Liquid Chromatography (HIC)

Test conditions: HIC-HPLC: Tosoh TSK Gel Butyl, 4.6 mm×3.5 cm, 10 mm; buffer A: 20 mM sodium phosphate, 1.5 M ammonium sulfate, pH 7.0; buffer B: 20 mM sodium phosphate, 25% (v/v) isopronal, pH 7.0; flow rate: 1 m$^1$/min; gradient: 10% buffer B to 100% buffer B in 15 minutes; 10 μL of sample.

The following 4 antibody-drug conjugates were prepared using the above method: Her2-A'-7-Val-Cit-PAB-MMAE, Her2-A'-11-Val-Cit-PAB-MMAE, Her2-A'-10-Val-Cit-PAB-MMAE, Her2-575DZ-Val-Cit-PAB-MMAE, wherein the antibody is Her2 monoclonal antibody (the same as above). The coupling results of the above 4 antibody-drug conjugates were analyzed by HIC-HPLC and SDS-PAGE electrophoresis, which were shown in Table 1, FIG. 1A, FIG. 1B, FIG. 1C, FIG. 1D and FIG. 2A, FIG. 2B.

In Table 1 and FIG. 1A, FIG. 1B, FIG. 1C, FIG. 1D, D0% represented a proportion of antibody-drug conjugates with 0 drug coupled to one antibody via linker, i.e., a proportion of naked antibody, D1% represented a proportion of antibody-drug conjugates with 1 drug coupled to one antibody via linker, D2% represented a proportion of antibody-drug conjugates with 2 drugs coupled to one antibody via linker, D3% represented a proportion of antibody-drug conjugates with 3 drugs coupled to one antibody via linker, D4% represented a proportion of antibody-drug conjugates with 4 drugs coupled to one antibody via linker, and D5% represented a proportion of antibody-drug conjugates with 5 drugs coupled to one antibody via linker.

The results showed that the average DAR value of Her2-A'-7-Val-Cit-PAB-MMAE was 4.10 (the molar ratio of drug to antibody during coupling was 5:1); the average DAR value of Her2-A'-11-Val-Cit-PAB-MMAE was 2.12 (the molar ratio of drug to antibody was 5:1 during coupling); the average DAR value of Her2-A'-10-Val-Cit-PAB-MMAE was 2.26 (the molar ratio of drug to antibody was 5:1 during coupling); the average DAR value of Her2-575DZ-Val-Cit-PAB-MMAE was 4.10 (the molar ratio of drug to antibody was 5:1 during coupling). The results showed that Her2-A'-7-Val-Cit-PAB-MMAE, Her2-A'-11-Val-Cit-PAB-MMAE, Her2-A'-10-Val-Cit-PAB-MMAE all had good coupling effect (the average DAR value was between 2-4 under ideal conditions), wherein the DAR2 ratios of Her2-A'-11-Val-Cit-PAB-MMAE and Her2-A'-10-Val-Cit-PAB-MMAE were 65.574% and 78.9% respectively, the D4% ratio of Her2-A'-7-Val-Cit-PAB-MMAE was 59.45%, the DAR value distribution was very concentrated, and the product uniformity was very good (all being better than Her2-575DZ-Val-Cit-PAB-MMAE).

TABLE 1

Analytical results of the antibody-drug conjugates by hydrophobic high performance liquid chromatography (HIC-HPLC)

| ADC | D0% | D1% | D2% | D3% | D4% | D5% | DAR |
| --- | --- | --- | --- | --- | --- | --- | --- |
| Her2-A'-7-Val-Cit-PAB-MMAE | 0 | 0.07 | 1.93 | 12.16 | 59.45 | 26.40 | 4.10 |
| Her2-A'-10-Val-Cit-PAB-MMAE | 0 | 9.03 | 78.9 | 11.9 | 0 | 0 | 2.26 |
| Her2-A'-11-Val-Cit-PAB-MMAE | 0 | 11.41 | 65.57 | 23.02 | 0 | 0 | 2.12 |
| Her2-575DZ-Val-Cit-PAB-MMAE | 0 | 0 | 1.99 | 18.46 | 52.94 | 21.17 | 4.10 |

Figure 2A:
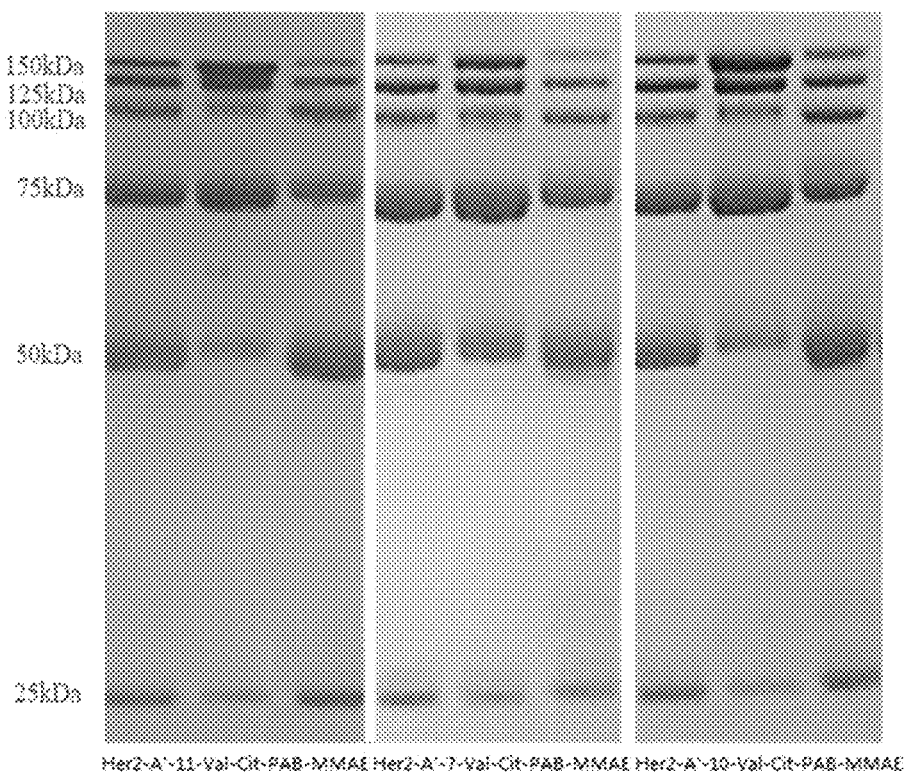
FIG. 2A shows SDS-PAGE electrophoresis patterns of Her2-A'-11-Val-Cit-PAB-MMAE (coupling buffers respectively have pH of 8.5, 9.0, 7.4), Her2-A'-7-Val-Cit-PAB-MMAE (coupling buffers respectively have pH of 8.5, 9.0, 7.4), Her2-A'-10-Val-Cit-PAB-MMAE (coupling buffers respectively have pH of 8.5, 9.0, 7.4) (coupling buffer has pH of 9.0).
Figure 2B:
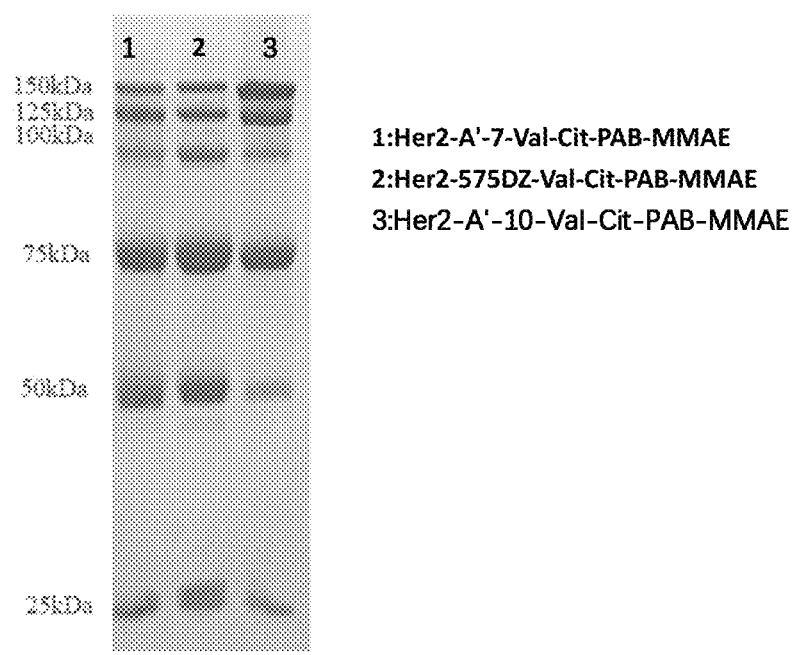
FIG. 2B shows SDS-PAGE electrophoresis patterns of Her2-A'-7-Val-Cit-PAB-MMAE, Her2-575DZ-Val-Cit-PAB-MMAE, Her2-A'-10-Val-Cit-PAB-MMAE (coupling buffer has pH of 9.0).

FIG. 2A, FIG. 2B showed the SDS-PAGE electrophoresis patterns of the above antibody-drug conjugates, wherein FIG. 2A showed the SDS-PAGE electrophoresis patterns of Her2-A'-11-Val-Cit-PAB-MMAE (coupling buffers respectively had pH of 8.5, 9.0, 7.4), Her2-A'-7-Val-Cit-PAB-MMAE (coupling buffers respectively had pH of 8.5, 9.0, 7.4), Her2-A'-10-Val-Cit-PAB-MMAE (coupling buffers respectively had pH of 8.5, 9.0, 7.4), and FIG. 2B showed the SDS-PAGE electrophoresis patterns from left to right of Her2-A'-7-Val-Cit-PAB-MMAE, Her2-575DZ-Val-Cit-PAB-MMAE, Her2-A'-10-Val-Cit-PAB-MMAE (coupling buffer had pH of 9.0).

Due to the use of reduction electrophoresis, all the thio groups among antibodies were exposed. Therefore, 25 KD represented the molecular weight of one light chain of the antibody, 50 KD represented the molecular weight of one heavy chain, and 75 KD represented the molecular weight of one light chain and one heavy chain (i.e., one linker was covalently linked to the thio group between one heavy chain and one light chain), 100 KD represented the molecular weight of two heavy chains (i.e., one linker was covalently linked to the thio group between two heavy chains), 125 KD represented the molecular weight of one light chain and two heavy chains (i.e., one linker was covalently linked to the thio groups among two heavy chains and one light chain), 150 KD represented the molecular weight of two heavy chains and two light chains (i.e., one linker was covalently linked to the thio groups among two heavy chains and two light chains).

FIG. 2A showed that the antibody-drug conjugates (Her2-A'-7-Val-Cit-PAB-MMAE, Her2-A'-10-Val-Cit-PAB-MMAE, Her2-A'-11-Val-Cit-PAB-MMAE) provided in the present examples each had linkers that were simultaneously covalently linked to the thio groups respectively between one heavy chain and one light chain (75 KD), between two heavy chains (100 KD), among two heavy chains and one light chain (125 KD), or among two heavy chains and two light chains (150 KD), which proved that the 4 pairs of disulfide bonds in the antibody were fully or partially bridged, and the bridge coupling effect was better.

FIG. 2B showed the parallel contrast SDS-PAGE electrophoresis patterns of Her2-A'-7-Val-Cit-PAB-MMAE, Her2-575DZ-Val-Cit-PAB-MMAE, Her2-A'-10-Val-Cit-PAB-MMAE (coupling buffer had pH of 9.0). From the Figure, it could be seen that the ratio of 150 KD and 125 KD bands in the conjugates Her2-A'-7-Val-Cit-PAB-MMAE and Her2-A'-10-Val-Cit-PAB-MMAE was significantly higher than the ratio of the corresponding bands in the conjugate Her2-575DZ-Val-Cit-PAB-MMAE. At the same time, the ratio of 50 KD and 25 KD bands was also significantly reduced, which proved that the first linker moiety of the present invention had better coupling efficiency and could result in an antibody-drug conjugate with a higher bridging ratio.

Example 28 Hydrolysis Analysis of Antibody-Drug Conjugate

The hydrolysis result of the antibody-drug conjugate (claudin18.2-A'-7-VC-PAB-MMAE) was characterized by molecular weight analysis and protein isoelectric point analysis.

1) Molecular Weight Analysis (LC-MS)

Test conditions: instrument model: Thermo Q Exactive Plus; mobile phase: 25 mM ammonium acetate solution; flow rate: 0.3 mL/min; injection volume: 1 mg/mL, 20 µL, i.e., 20 µg; detection range: 5000-8000 Da; output range: 140000-160000 Da.

2) Isoelectric Point Distribution Analysis

Instrument Information: Imaging Capillary Isoelectric Focusing Electrophoresis Instrument, model: ICE 3.

Instrument settings: focus time 1: 1500V for 1.00 min; focus time 2: 3000V for 8.00 min.

Naked antibody (claudin18.2 antibody): amphoteric electrolyte carrier: 1% Pharmalyte 5-8, 3% Pharmalyte 8-10.5; low isoelectric point marker: 8.18; high electric point marker: 9.77; protein concentration: 0.25 mg/mL; tray temperature: 15° C.

claudin18.2-A'-7-VC-PAB-MMAE: amphoteric electrolyte carrier: 3% Servalyt 5-9, 1% Servalyt 9-11; low isoelectric point marker: 5.85; high electric point marker: 9.46; protein concentration: 0.50 mg/mL; tray temperature: 15° C.

Figure 6A:
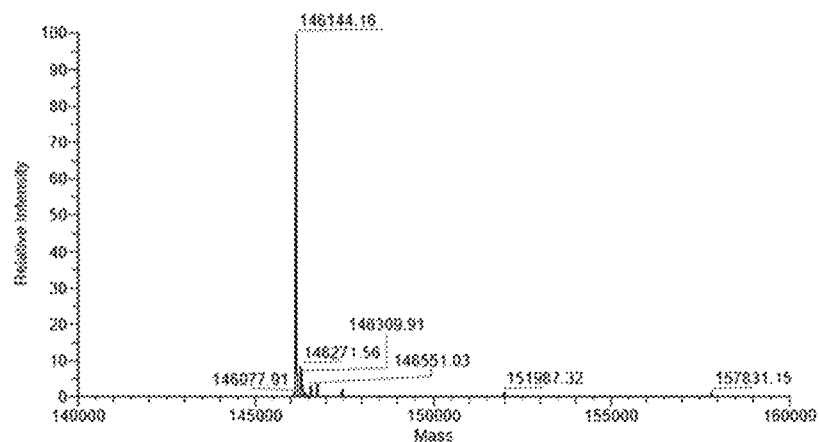
FIG. 6A shows an LC-MS spectrum of naked antibody (claudine 18.2 antibody).
Figure 6B:
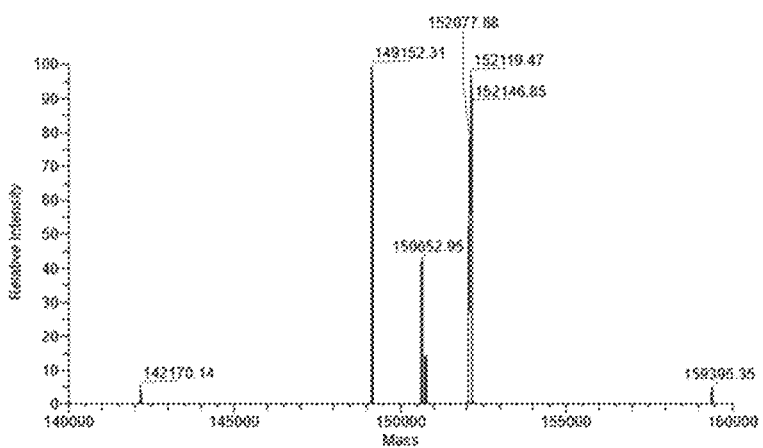
FIG. 6B shows an LC-MS spectrum of claudine 18.2-A'-7-VC-PAB-MMAE.

FIG. 6A showed the molecular weight result of naked antibody, and FIG. 6B showed the molecular weight result of claudin18.2-A'-7-VC-PAB-MMAE. From the Figures, it could be seen that the molecular weight of naked antibody was 145144 Da, and the molecular weights of claudin18.2-A'-7-VC-PAB-MMAE (when the ratio of A'-7-VC-PAB-MMAE to antibody was 4:1) were 152078 Da, 152119 Da, 152147 Da. When one antibody was coupled with 4 A'-7-VC-PAB-MMAE without hydrolysis, its theoretical molecular weight was 151999 Da. The actual determined molecular weights were 152078 Da, 152119 Da, 152147 Da, which had a big deviation from the theoretical molecular weight, exceeding the deviation range (20 Da) of the instrument. When the conjugate claudin18.2-A'-7-VC-PAB-MMAE underwent hydrolysis in which 4, 7, 8 maleimides were hydrolyzed, its theoretical molecular weights were 152071 Da, 152125 Da, 152143 Da. Compared with these theoretical values, the relative deviation of the actual determined values was within the deviation range of the instrument. It was speculated that antibody-A'-7-VC-PAB-MMAE was partially hydrolyzed.

Figure 7A:
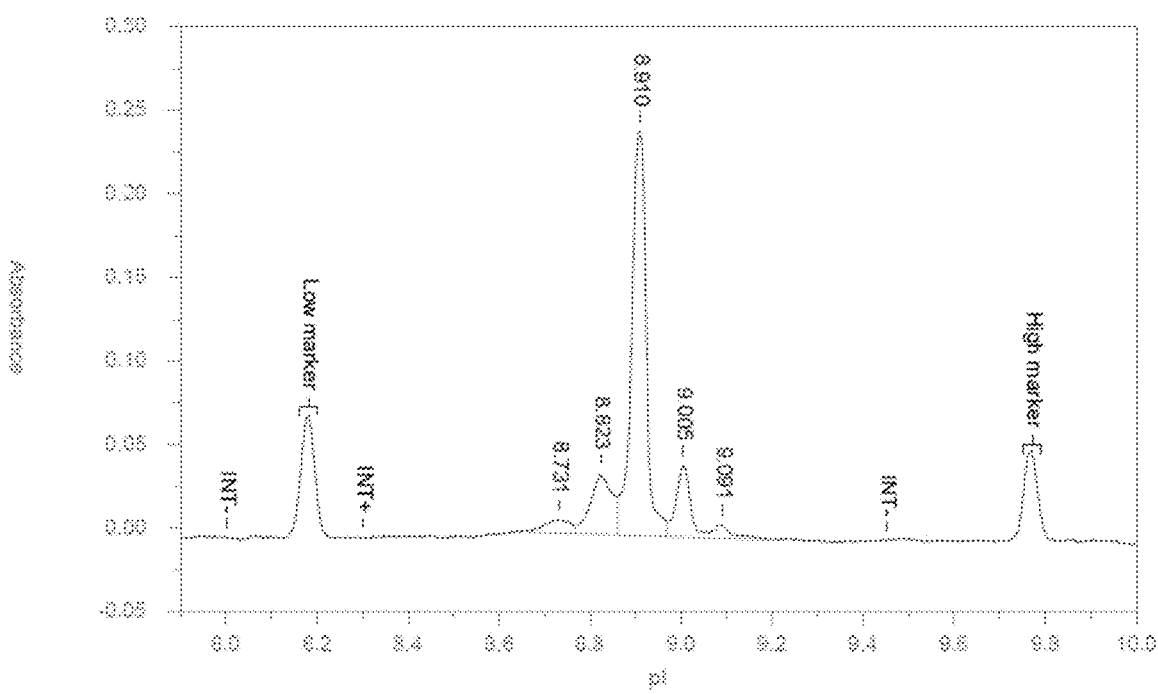
FIG. 7A shows an isoelectric point distribution map of naked antibody (claudine 18.2 antibody).
Figure 7B:
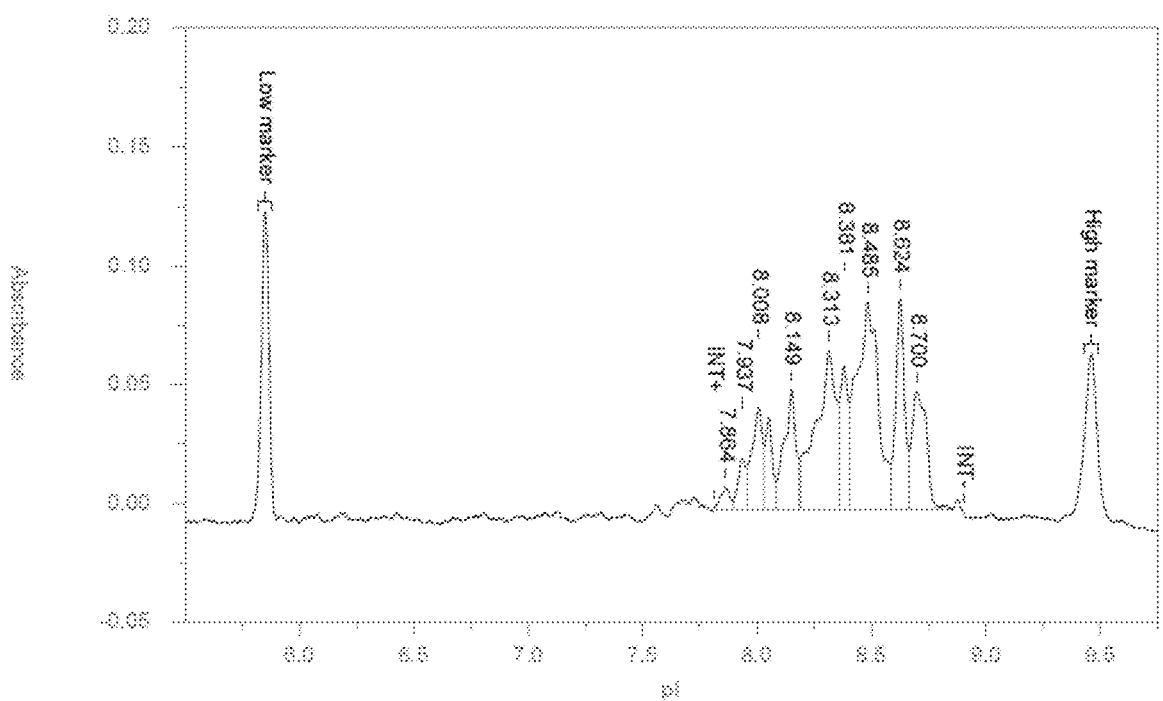
FIG. 7B shows an isoelectric point distribution map of claudine 18.2-A'-7-VC-PAB-MMAE.

Next, the hydrolyzed moiety was studied. FIG. 7A showed the isoelectric point distribution result of naked antibody, and FIG. 7B showed the isoelectric point distribution result of claudin18.2-A'-7-VC-PAB-MMAE. From FIG. 7A, it could be seen that the main peak of isoelectric point of naked antibody was 8.91, and the ratio of acidic peak (isoelectric point <8.91) and alkaline peak (isoelectric point >8.91) was relatively low. From FIG. 7B, it could be seen that the isoelectric point of antibody-A'-7-VC-PAB-MMAE was distributed between 7.86-8.70. Compared with naked antibody, the isoelectric point of antibody-A'-7-VC-PAB-MMAE was significantly decreased, indicating that there were more acidic groups, such as carboxyl groups, on its surface. By combining the structural analysis, it could be seen that the position of hydrolysis was in the maleimide moiety of antibody-A'-7-VC-PAB-MMAE, and, by controlling the synthesis and hydrolysis environment of the antibody-drug conjugate, it was possible to control the degree of hydrolysis of maleimide in the linker of the antibody-drug conjugate, for example, to achieve full hydrolysis or no hydrolysis. In addition, purification means could also be employed to separate products, which were hydrolysed at the same degree, from the synthesized products.

Example 29 Determination of Affinity of Antibody-Drug Conjugates to Antigen (ELISA Method)

Figure 3:
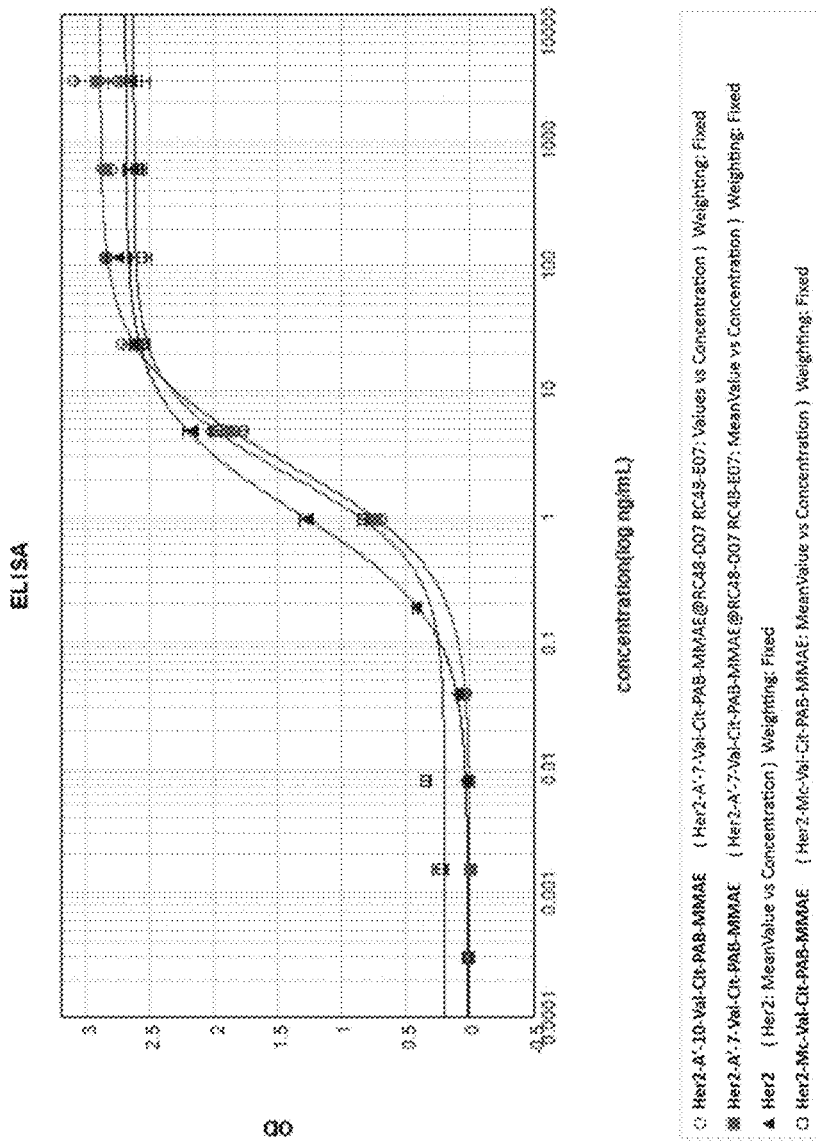
FIG. 3 shows affinity curves to antigen of antibody-drug conjugates (the antibody-drug conjugates being Her2-A'-7-Val-Cit-PAB-MMAE and Her2-A'-10-Val-Cit-PAB- MMAE; Her2 antibody and Her2-Mc-Val-Cit-PAB-MMAE being negative and positive controls) as determined by ELISA method, wherein the abscissa is concentration, and the ordinate is optical density absorption.

General procedure: antigen was diluted with a coating buffer to the required concentration (such as 500 ng/ml, 250 ng/ml, 100 ng/ml, or arranged by oneself according to experimental needs) at 100 µl/well, and set aside at 4° C. overnight; plate washing: a plate was washed 3 times with a PBST washing solution at 350 µl/well, and pat dried; blocking: the plate was blocked with 3% BSA blocking solution at 200 µl/well, and set aside at 4° C. overnight; plate washing: the plate was washed twice with PBST at 300 µl/well, and the solution in the well was blotted; loading of sample: a sample was diluted with a diluent 1% BSA-PBST solution, then the diluted sample was added to the blocked cell culture plate at 100 µl/well, with three replicates, and the diluent as a blank control, and incubated in a incubator at 37° C. for 2 h (the dilution scheme could be changed according to actual situation); plate washing: the plate was washed twice with PBST at 200 µl/well, and the solution in the well was blotted; loading of test antibody: Goat antA-Human IgG-Fc HRP conjugated was diluted at 1:5000 with 1% BSA-PBST at 100 µl/well, and incubated at 37° C. for 1 h (the diluent could be changed according to actual situation); plate washing: the plate was washed 4 times with PBST at 200 µl/well, and the solution in the well was blotted; color development: TMB substrate was added at 100 µl/well, to effect color development for 2 min; termination: 2 M $H_2SO_4$ was added at 50 µl/well to terminate the reaction; reading: the optical density absorbance at 450/655 nm was measured by a microplate reader, and the experimental results were analyzed by prism analysis software, with the concentration as the abscissa, and the optical density absorbance as the ordinate, the values of $EC_{50}$ and the like were automatically calculated by the software. The results were shown in Table 2 and FIG. 3.

Table 2 showed the $EC_{50}$ values of the antibody-drug conjugates (Her2-A'-7-Val-Cit-PAB-MMAE, Her2-A'-10-Val-Cit-PAB-MMAE) against Her2 antigen, wherein Her2 was naked antibody, with Her2-Mc-vc-PAB-MMAE as the control ADC. The results showed that Her2-A'-10-Val-Cit-PAB-MMAE and Her2-A'-7-Val-Cit-PAB-MMAE both had better affinity to the antigen, and the data results showed that the linking method used did not change the original affinity of the antibody.

TABLE 2

Affinity of the antibody-drug conjugates to antigen ($EC_{50}$ value)

| ADC | $EC_{50}$ (ng/ml) | $R^2$ |
|---|---|---|
| Her2 | 1.073 | 0.999 |
| Her2-Mc-vc-PAB-MMAE | 2.132 | 0.994 |
| Her2-A'-10-Val-Cit-PAB-MMAE | 1.725 | 0.999 |
| Her2-A'-7-Val-Cit-PAB-MMAE | 2.692 | 1.000 |

Example 30 In Vitro Efficacy Test

Figure 4A:
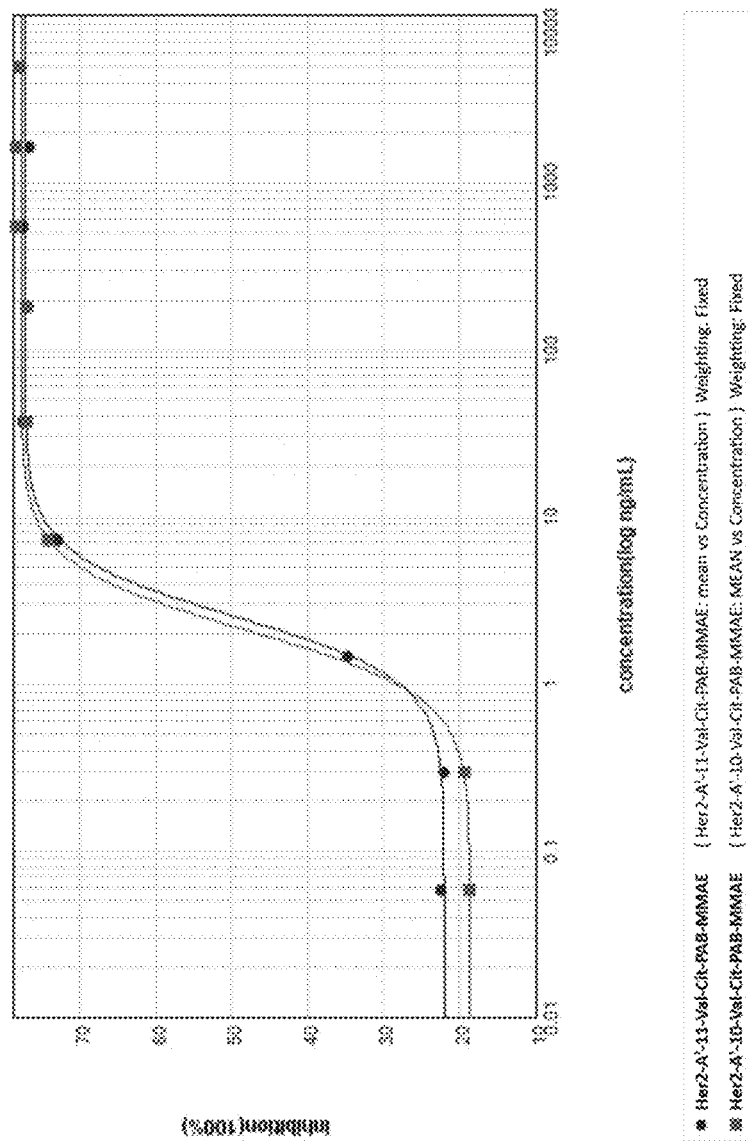
FIG. 4A shows proliferation inhibition rate curves against human breast cancer SK-BR-3 cells of antibody-drug conjugates (Her2-A'-11-Val-Cit-PAB-MMAE, Her2-A'-10-Val-Cit-PAB-MMAE).
Figure 4B:
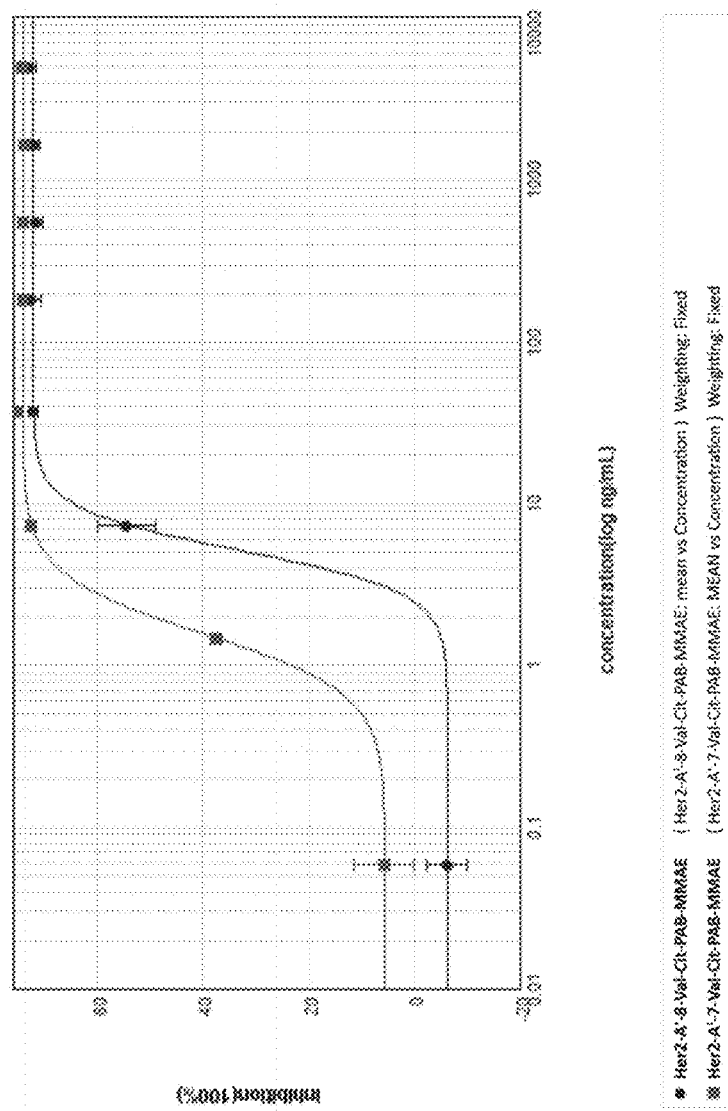
FIG. 4B shows proliferation inhibition rate curves against human breast cancer SK-BR-3 cells of antibody-drug conjugate (Her2-A'-8-Val-Cit-PAB-MMAE, Her2-A'-7-Val-Cit-PAB-MMAE).

A culture dish containing human breast cancer SK-BR-3 cells and culture medium was placed in a 37° C., 5% $CO_2$ incubator for incubation. The cells in good growth condition were taken and the original culture medium was discarded, then the obtained cells were suspended with the culture medium and counted separately. The cell suspension was added to a 96-well plate (5000 cells per well), and incubated in a 37° C., 5% $CO_2$ incubator overnight. Then a drug which had been diluted was added to the cell suspension for incubation. After incubation for 72 h, Cell Counting Kit-8 (abbreviated as CCK-8 kit) was used for active color development, and the 96-well plate after color development was detected by a microplate reader to obtain OD value at 450 nm. $IC_{50}$ value was calculated through the OD value by Prism software. A four parameter curve fitting was performed by using the software with the inhibition rate as y value, and the drug concentration as x value, and the drug concentration value (which was defaulted to be the $IC_{50}$ value by the software) corresponding to the inhibition rate value between the maximum inhibition rate and the minimum inhibition rate was recorded. When the fitted curve was "S curve" and $R^2 \geq 0.95$, the $IC_{50}$ value was valid. The $IC_{50}$ values of the antibody-drug conjugates Her2-A'-8-Val-Cit-PAB-MMAE, Her2-A'-7-Val-Cit-PAB-MMAE, Her2-A'-11-Val-Cit-PAB-MMAE, Her2-A'-10-Val-Cit-PAB-MMAE against human breast cancer SK-BR-3 cells were shown in Table 3, and the inhibition rate curves were shown in FIG. 4A and FIG. 4B.

Table 3 showed the $IC_{50}$ inhibition rates of the antibody-drug conjugates (Her2-A'-8-Val-Cit-PAB-MMAE, Her2-A'-7-Val-Cit-PAB-MMAE, Her2-A'-11-Val-Cit-PAB-MMAE, Her2-A'-10-Val-Cit-PAB-MMAE) against human breast cancer SK-BR-3 cells.

TABLE 3

In vitro efficacy of the antibody-drug conjugates against human breast cancer SK-BR-3 cells

| ADC | $IC_{50}$ (ng/ml) |
|---|---|
| Her2-A'-8-Val-Cit-PAB-MMAE | 5.13 |
| Her2-A'-7-Val-Cit-PAB-MMAE | 1.57 |
| Her2-A'-11-Val-Cit-PAB-MMAE | 2.53 |
| Her2-A'-10-Val-Cit-PAB-MMAE | 2.11 |

The present invention has been exemplified by various specific embodiments. However, those of ordinary skill in the art can understand that the present invention is not limited to each specific embodiment, and those of ordinary skill in the art can make various changes or modifications within the scope of the present invention, and the various technical features mentioned in the present specification can be combined with each other without departing from the spirit and scope of the present invention. Such changes and modifications are all within the scope of the present invention.

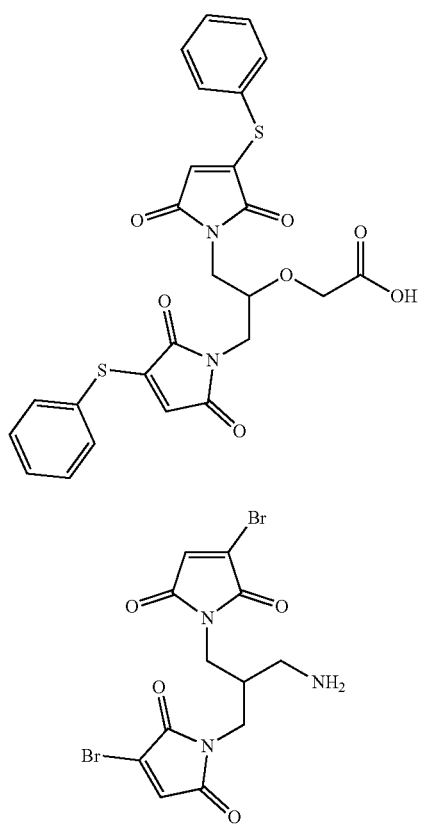
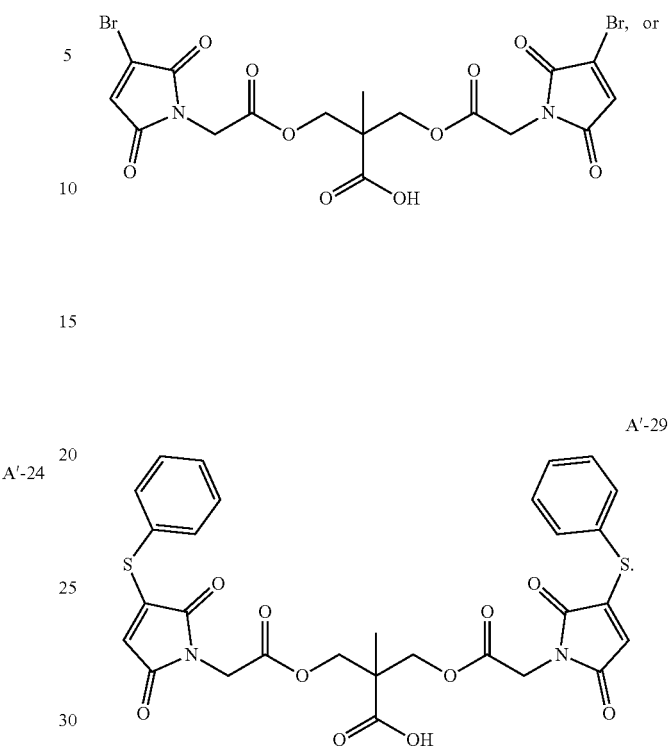

The invention claimed is:

1. A linker having the structure:

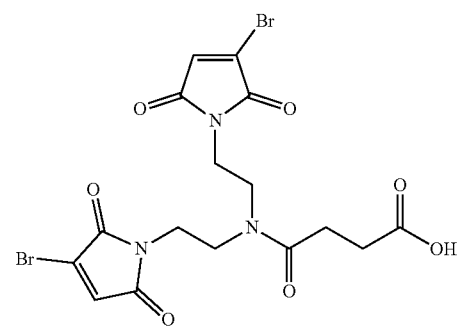

A'-7

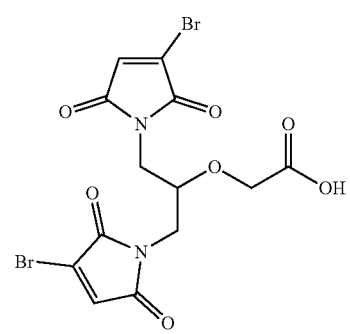

A'-8

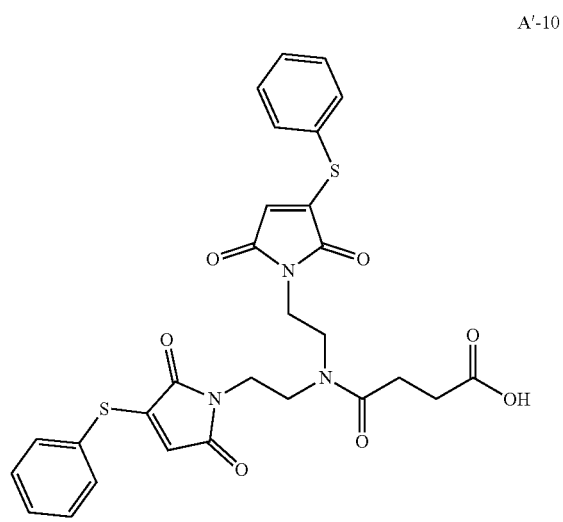

A'-10